US010683307B2

(12) United States Patent
Cui et al.

(10) Patent No.: US 10,683,307 B2
(45) Date of Patent: *Jun. 16, 2020

(54) COMPOUNDS FOR USE IN ANTIBACTERIAL APPLICATIONS

(71) Applicant: GLAXOSMITHKLINE INTELLECTUAL PROPERTY DEVELOPMENT LIMITED, Brentford, Middlesex (GB)

(72) Inventors: Haifeng Cui, King of Prussia, PA (US); Alan Hennessy, Cricklade (GB); Qi Jin, King of Prussia, PA (US); Timothy James Miles, Tres Cantos (ES); Stephen Frederick Moss, Ickleton (GB); Neil David Pearson, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/415,319

(22) Filed: May 17, 2019

(65) Prior Publication Data

US 2019/0270755 A1   Sep. 5, 2019

Related U.S. Application Data

(63) Continuation of application No. 15/752,639, filed as application No. PCT/IB2016/054890 on Aug. 15, 2016, now Pat. No. 10,364,254.

(60) Provisional application No. 62/308,928, filed on Mar. 16, 2016, provisional application No. 62/205,732, filed on Aug. 16, 2015.

(51) Int. Cl.
 *C07D 498/04* (2006.01)
 *C07D 513/04* (2006.01)
 *C07D 519/00* (2006.01)
 *A61P 31/04* (2006.01)

(52) U.S. Cl.
 CPC ............ *C07D 498/04* (2013.01); *A61P 31/04* (2018.01); *C07D 513/04* (2013.01); *C07D 519/00* (2013.01)

(58) Field of Classification Search
 CPC .................... C07D 498/04; C07D 513/04
 See application file for complete search history.

(56) References Cited

U.S. PATENT DOCUMENTS

| 7,498,326 B2 | 3/2009 | Axten et al. |
| 7,605,169 B2 | 10/2009 | Miller et al. |
| 7,622,481 B2 | 11/2009 | Axten et al. |
| 7,875,715 B2 | 1/2011 | Breault et al. |
| 8,044,044 B2 | 10/2011 | Hubschwerlen |
| 8,071,592 B2 | 12/2011 | Ballell et al. |
| 8,124,602 B2 | 2/2012 | Breault et al. |
| 8,211,908 B2 | 7/2012 | Kiyoto et al. |
| 8,329,694 B2 | 12/2012 | Kiyoto et al. |
| 8,367,831 B2 | 2/2013 | Kiyoto et al. |
| 8,524,738 B2 | 9/2013 | Kiyoto et al. |
| 2009/0131444 A1 | 5/2009 | Reck et al. |
| 2009/0270374 A1 | 10/2009 | Ballell et al. |
| 2010/0029623 A1 | 2/2010 | Hubschwerlen et al. |
| 2014/0243302 A1 | 8/2014 | Fukuda et al. |

FOREIGN PATENT DOCUMENTS

| CN | 1535272 A | 10/2004 | |
| JP | S4632671 | 9/1971 | |
| JP | 2009149618 A | 7/2009 | |
| JP | 5620636 B2 | 11/2014 | |
| WO | WO 2004/002490 A1 | 1/2004 | |
| WO | WO 2004/002490 A3 | 1/2004 | |
| WO | WO 2004/002990 A2 | 1/2004 | |
| WO | WO 2004/002992 A1 | 1/2004 | |
| WO | WO 2004/087145 A2 | 10/2004 | |
| WO | WO 2006/0214448 A1 | 3/2006 | |
| WO | WO 2006/081264 A1 | 8/2006 | |
| WO | WO 2007/072151 A1 | 6/2007 | |
| WO | WO 2007/093963 A1 | 8/2007 | |
| WO | WO 2007/138974 A1 | 12/2007 | |
| WO | WO 2008/009700 A1 | 1/2008 | |
| WO | WO 2008/078305 A2 | 7/2008 | |
| WO | WO 2008/128961 A1 | 10/2008 | |
| WO | WO 2010/046388 A1 | 4/2010 | |
| WO | WO-2010045987 A1 * | 4/2010 | ........... C07D 471/04 |
| WO | WO 2010/055348 A1 | 5/2010 | |
| WO | WO 2011/148962 A1 | 12/2011 | |
| WO | WO 2014/170821 A1 | 10/2014 | |
| WO | WO-2017029602 A2 * | 2/2017 | ........... C07D 498/04 |

OTHER PUBLICATIONS

Wermuth, C.G. "Molecular Variations Based on Isosteric Replacements" in "The Practice of Medicinal Chemistry" 1996, Academic Press Limited, pp. 203-237 (Year: 1996).*
Patani et al. Chem. Rev. 1996, 96, 3147-3176 (Year: 1996).*
Sheridan, R.P. J. Chem. Inf. Comput. Sci. 2002, 42, 103-108 (Year: 2002).*
Thalji, Reema K. Abstract, 250th ACS National Meeting & Exposition, Aug. 16-20, 2015, Boston, MA, United States. "Structure-Guided Design and Optimization of Fluoroquinolone-Substituted Bacterial Type IIA DNA Topoisomerase", Abstract Publication date: Aug. 14, 2015.

(Continued)

*Primary Examiner* — Matthew P Coughlin
(74) *Attorney, Agent, or Firm* — Donald Huddler; Duke Fitch; Edward R. Gimmi

(57) ABSTRACT

The present invention relates to novel compounds or pharmaceutically acceptable salts thereof, corresponding pharmaceutical compositions and treatment methods or uses as antibacterials for bacterial infections.

7 Claims, No Drawings

(56) References Cited

OTHER PUBLICATIONS

Reck, et al. "Optimization of Physicochemical Properties and Safety Profile of Novel Bacterial Topoisomerase Type II Inhibitors (NBTIs) with Activity Against Pseudomonas Aeruginosa". Bioorganic & Medicinal Chemistry, 22(19): 5392-5409 (2014).

Thalji, Reema K. "Structure-Guided Design and Optimization of Fluoroquinolone-Substituted Bacterial Type IIA DNA Topoisomerase Inhibitors". Presentation at ACS Fall Meeting, Boston, MA pp. 1-22, Aug. 17, 2015.

* cited by examiner

COMPOUNDS FOR USE IN ANTIBACTERIAL APPLICATIONS

This application is a continuation of U.S. application Ser. No. 15/752,639, filed 14 Feb. 2018, which is a 371 Application of PCT/IB2016/054890, filed 15 Aug. 2016, which claims the priority of U.S. Provisional Application No. 62/308,928, filed 16 Mar. 2016, and U.S. Provisional Application No. 62/205,732, filed 16 Aug. 2015, all of which are incorporated herein in their entireties.

FIELD OF THE PRESENT INVENTION

The present invention relates to novel compounds or pharmaceutically acceptable salts, solvates or N-oxides thereof, corresponding pharmaceutical compositions containing them and treatment methods or uses as antibacterials.

BACKGROUND OF THE PRESENT INVENTION

Over the past several decades, the frequency of antimicrobial resistance and its association with serious infectious diseases has increased at alarming rates. For example, in the United States, the Centers for Disease Control and Prevention estimate that roughly 1.7 million hospital-associated infections, from all types of microorganisms, including bacteria, combined, cause or contribute to 99,000 deaths each year. Nosocomial infections can cause severe pneumonia and infections of the urinary tract, bloodstream and other parts of the body. Many types are difficult to attack with antibiotics, and antibiotic resistance is spreading to bacteria that can infect people outside the hospital (see, Pollack, Andrew. "Rising Threat of Infections Unfazed by Antibiotics" New York Times, Feb. 27, 2010). This high rate of resistance increases the morbidity, mortality, and costs associated with nosocomial infections. There is a perceived need to identify novel lead series with new antibacterial modes of action.

The problem of antibacterial resistance is compounded by the existence of bacterial strains resistant to multiple antibacterials. Drug resistant infections are an increasing threat to public health, especially for seriously ill, hospitalized patients. Infections arising from multidrug resistant MRSA, Pseudomonas aeruginosa and Acinetobacter species as well as drug resistant Klebsiella pneumoniae present formidable challenges for the medical community as few treatment options remain. Unfortunately, while resistance to current therapies continues to spread, new clinical agents to treat these infections are few in number.

WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06017468, WO06020561, WO01/25227, WO02/40474, WO02/07572, WO2004035569, WO2004089947, WO004024712, WO004024713, WO004087647, WO2005016916, WO2005097781, WO006010831, WO004035569, WO004089947, WO06021448, WO06032466, WO06038172, WO06046552, WO06134378 WO006137485 and WO08009700 disclose quinoline, N-ethylquinolone, N-ethyl-azaquinolone, naphthyridine, morpholine, cyclohexane, piperidine and piperazine derivatives having antibacterial activity. Thus there is a need for new antibacterials, particularly antibacterials with novel mechanisms of action.

SUMMARY OF THE PRESENT INVENTION

The present invention relates to novel compounds or pharmaceutically acceptable salts thereof, corresponding pharmaceutical compositions containing them and treatment methods or uses as antibacterials.

In one aspect, the present invention provides a compound of formula (I):

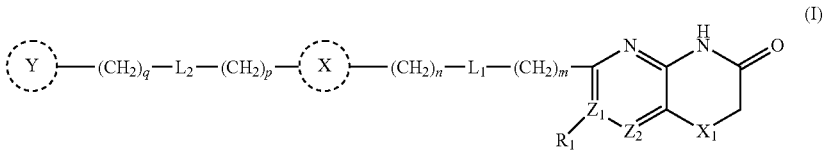

Where:
$Z_1$ is C or N, $Z_2$ is CH or N, and wherein when $Z_1$ is N, $R_1$ is absent;
$R_1$, $R_2$ and $R_3$ are independently selected from —H or $(C_1-C_6)$alkyl;
$X_1$ is selected from O or S;
$L_1$ is selected from a bond, —O—, $(C_1-C_6)$alkyl, —C(=O), —CH(NH$_2$), —NHCH$_2$CH(OH), —NHC(=O) or NR$_2$;
X is selected from $(C_5-C_{14})$aryl, $(C_2-C_9)$heteroaryl, $(C_3-C_{12})$cycloalkyl, or $(C_2-C_9)$heterocycle;
$L_2$ is selected from a bond, —O—, $(C_1-C_6)$alkyl, —C(=O), CH(NH$_2$), —NHCH$_2$CH(OH), —NHC(=O) or NR$_3$; Y is a $(C_5-C_{14})$ heteroaryl containing at least one heteroatom independently selected from O, N, and S;
wherein:
said $(C_5-C_{14})$ heteroaryl is optionally substituted by at least one group independently selected from $(C_1-C_6$ alkyl), $(C_1-C_6$alkoxy), halogen, oxo, $(C_1-C_6$ alkyl)NR$_4$R$_5$, —O—$(C_1-C_6$alkyl)-NR$_4$R$_5$, wherein $R_4$ and $R_5$ are each independently selected from H, $(C_1-C_6)$alkyl, —OH, CH$_2$—CH=N—(R$_6$), wherein $R_6$ is OH, $(C_1-C_6)$alkyl or halogen, or —O—CH—(R$_7$)$_2$;
wherein:
$R_7$ is halogen or —N=N=N;
m is an integer ranging from 0 to 8;
n is an integer ranging from 0 to 8;
p is an integer ranging from 0 to 8; and
q is an integer ranging from 0 to 8; or
a pharmaceutically acceptable salt thereof.

In another aspect, the present invention provides a pharmaceutical composition comprising a compound according to Formula (I) or a pharmaceutically acceptable salt thereof and a pharmaceutically acceptable carrier.

In another aspect, the present invention provides a method of treating a bacterial infection-comprising administrating a compound according to formula (I) or a pharmaceutically acceptable salt, solvate or N-oxide thereof to a subject in need thereof.

In another aspect, the present invention provides a method of treating a bacterial infection-comprising administrating a pharmaceutical composition comprising a compound according to formula (I) or a pharmaceutically acceptable salt thereof to a subject in need thereof.

In another aspect, the present invention provides for uses of compounds or pharmaceutically acceptable salts or corresponding pharmaceutical compositions of the present invention for uses in the manufacture of a medicament in the treatment of bacterial infections.

These and other aspects of the invention are presented herein.

DETAILED DESCRIPTION OF THE PRESENT INVENTION

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

Further, all publications, patents and patent applications cited herein, whether supra or infra, are hereby incorporated by reference in their entirety.

As used herein, the term "optionally substituted" means that a group, such as, which may include, but is not limited to alkyl, aryl, heteroaryl, etc., may be unsubstituted, or the group may be substituted with one or more substituent(s) as defined. In the case where groups may be selected from a number of alternative groups the selected groups may be the same or different.

The term "independently" means that where more than one substituent is selected from a number of possible substituents, those substituents may be the same or different.

Finally, as used in this specification and the appended claims, the singular forms "a", "an", "the" and "one" include plural referents unless the content clearly dictates otherwise.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x$-$C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" or "alkylene" refers to divalent saturated aliphatic hydrocarbyl groups having from 1 to 10 carbon atoms and, in some embodiments, from 1 to 6 carbon atoms. "$(C_u$-$C_v)$alkylene" refers to alkylene groups having from u to v carbon atoms. The alkylene groups include branched and straight chain hydrocarbyl groups. For example, "$(C_1$-$C_6)$alkylene" is meant to include methylene, ethylene, propylene, 2-methypropylene, dimethylethylene, pentylene, and so forth. As such, the term "propylene" could be exemplified by the following structure:

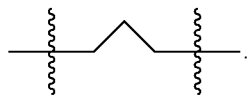

Likewise, the term "dimethylbutylene" could be exemplified by any of the following three structures or more:

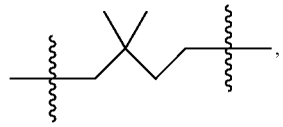 [SMILES: *CCC(C)(C)C*]

p, or

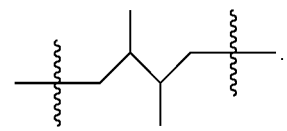 [SMILES: *CC(C)C(C)C*]

Furthermore, the term "$(C_1$-$C_6)$alkylene" is meant to include such branched chain hydrocarbyl groups as cyclopropylmethylene, which could be exemplified by the following structure:

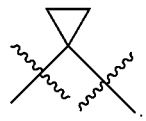 [SMILES: *C1(*)CC1]

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x$-$C_y$)alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, ($C_2$-$C_6$)alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}C(O)$alkyl, —$NR^{20}C(O)$cycloalkyl, —$NR^{20}C(O)$alkenyl, —$NR^{20}C(O)$alkynyl, —$NR^{20}C(O)$aryl, —$NR^{20}C(O)$heteroaryl, and —$NR^{20}C(O)$heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"AUC" refers to the area under the plot of plasma concentration of drug (not logarithm of the concentration) against time after drug administration.

"$EC_{50}$" refers to the concentration of a drug that gives half-maximal response.

"$IC_{50}$" refers to the half-maximal inhibitory concentration of a drug. Sometimes, it is also converted to the $pIC_{50}$ scale (–log $IC_{50}$), in which higher values indicate exponentially greater potency.

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g. 5,6,7,8-tetrahydronaphthalene-5-yl). The term "cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are exemplified and named below:

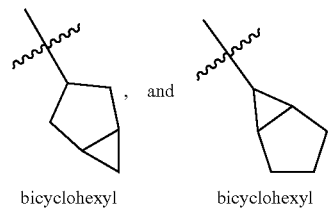

bicyclohexyl     bicyclohexyl

"$(C_u-C_v)$cycloalkyl" refers to cycloalkyl groups having u to v caron atoms.

"Carboxy" or "carboxyl" refers interchangeably to the groups

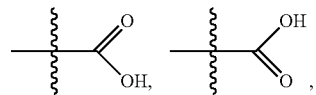

—C(O)O, or —$CO_2$.

"Halo" or "halogen" refers to fluoro, chloro, bromo, and iodo.

"Haloalkyl" refers to substitution of an alkyl group with 1 to 3 halo groups (e.g., bihaloalkyl or trihaloalkyl, bifluoromethyl or trifluoromethyl).

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy, bihaloalkoxy, trihaloalkoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" or "fused heterocycle" refer to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

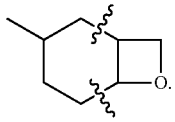

The term "heteroatom" means nitrogen, oxygen, or sulfur and includes any oxidized form of nitrogen, such as N(O) {N+—O⁻} and sulfur such as S(O) and S(O)$_2$, and the quaternized form of any basic nitrogen.

"Oxo" refers to a (=O) group.

"Protein binding" refers to the binding of a drug to proteins in blood plasma, tissue membranes, red blood cells and other components of blood.

"Protein shift" refers to determining a binding shift by comparing the EC$_{50}$ values determined in the absence and presence of human serum.

"Racemates" refers to a mixture of enantiomers. In an embodiment of the invention, the compounds of the invention, or pharmaceutically acceptable salts thereof, are enantiomerically enriched with at least one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical Rx to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

In various embodiments, when a compound of the invention is a base (contain a basic moiety), a desired salt form may be prepared by any suitable method known in the art, including treatment of the free base with an inorganic acid or with an organic acid, such as trifluoroacetic acid, mandelic acid, malonic acid, pyruvic acid, glycolic acid, salicylic acid, pyranosidyl acid, such as glucuronic acid or galacturonic acid, alpha-hydroxy acid, such as citric acid, amino acid, such as aspartic acid or glutamic acid, aromatic acid, such as cinnamic acid. Examples of pharmaceutically acceptable salts include sulfates, pyrosulfates, bisulfates, sulfites, bisulfites, phosphates, iodides, acetates, propionates, decanoates, caprylates, acrylates, formates, isobutyrates, caproates, heptanoates, propiolates, malonates succinates, suberates, sebacates, fumarates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates.

The invention also includes various deuterated forms of the compounds of Formulas (I) to (VII), respectively, or a pharmaceutically acceptable salt thereof. Each available hydrogen atom attached to a carbon atom may be independently replaced with a deuterium atom. A person of ordinary skill in the art will know how to synthesize deuterated forms of the compounds of Formulas (I) to (VII), respectively, or a pharmaceutically acceptable salt thereof of the present invention. For example, deuterated materials, such as alkyl groups may be prepared by conventional techniques (see for example: methyl-$d_3$-amine available from Aldrich Chemical Co., Milwaukee, Wis., Cat. No. 489,689-2).

The subject invention also includes isotopically-labeled compounds which are identical to those recited in Formulas (I) to (VII), respectively, or a pharmaceutically acceptable salt thereof but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

"Patient" or "subject" refers to mammals and includes humans and non-human mammals.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles may represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

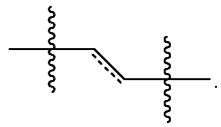

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N— containing heteroaryl ring with one to three double bonds arranged in any position that still depicts the proper valence:

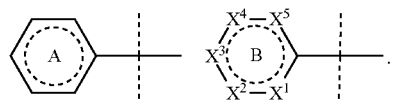

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

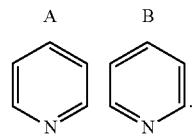

In one aspect, the invention provides a compound of formula (I):

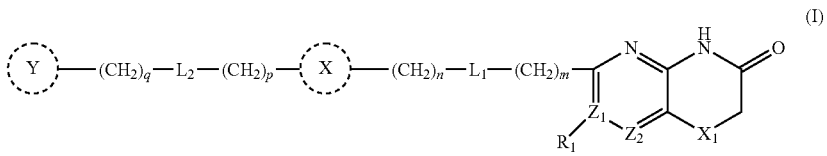

wherein:
$Z_1$ is C or N, $Z_2$ is CH or N, and wherein when $Z_1$ is N, $R_1$ is absent;
$R_1$, $R_2$ and $R_3$ are independently selected from —H or ($C_1$-$C_6$)alkyl;
$X_1$ is selected from O or S;
$L_1$ is selected from a bond, —O—, ($C_1$-$C_6$)alkyl, —C(=O), —CH(NH$_2$), —NHCH$_2$CH(OH), —NHC(=O) or NR$_2$;

X is selected from ($C_5$-$C_{14}$)aryl, ($C_2$-$C_9$)heteroaryl, ($C_3$-$C_{12}$)cycloalkyl, or ($C_2$-$C_9$)heterocycle;

$L_2$ is selected from a bond, —O—, ($C_1$-$C_6$)alkyl, —C(=O), CH(NH$_2$), —NHCH$_2$CH(OH), —NHC(=O) or NR$_3$;

Y is a ($C_5$-$C_{14}$) heteroaryl containing at least one heteroatom independently selected from O, N, and S;
wherein:
said ($C_5$-$C_{14}$) heteroaryl is optionally substituted by at least one group independently selected from ($C_1$-$C_6$ alkyl), ($C_1$-$C_6$alkoxy), halogen, oxo, ($C_1$-$C_6$ alkyl)NR$_4$R$_5$, —O—($C_1$-$C_6$alkyl)-NR$_4$R$_5$;
wherein:
$R_4$ and $R_5$ are each independently selected from H, ($C_1$-$C_6$)alkyl, —OH, —CH$_2$—CH=N—(R$_6$);
wherein:
$R_6$ is OH, ($C_1$-$C_6$)alkyl or halogen, or —O—CH—(R$_7$)$_2$
wherein:
$R_7$ is halogen or —N=N=N;
m is an integer ranging from 0 to 8;
n is an integer ranging from 0 to 8;
p is an integer ranging from 0 to 8;
q is an integer ranging from 0 to 8; or
a pharmaceutically acceptable salts thereof.

Solvates and N-oxides thereof of formula (I) may also be encompassed by the present invention.

In one embodiment, when $Z_1$ is C, $R_1$ is H or ($C_1$-$C_6$)alkyl and $Z_2$ is N. Most preferably in such an embodiment, $R_1$ is H. In one embodiment, when $Z_1$ is N ($R_1$ is absent), $Z_2$ is CH.

In one embodiment, $X_1$ is O. In one embodiment, when $X_1$ is O, $R_1$ is H, $Z_1$ is C and $Z_2$ is N. In another embodiment when $X_1$ is O, $R_1$ is CH$_3$, $Z_1$ is C and $Z_2$ is N. Other values for $Z_1$, $Z_2$ and $R_1$ are encompassed as set forth herein.

In one embodiment, $X_1$ is S. In one embodiment, when $X_1$ is S, $R_1$ is H, $Z_1$ is C and $Z_2$ is N. In another embodiment when $X_1$ is S, $R_1$ is CH$_3$, $Z_1$ is C and $Z_2$ is N. Other values for $Z_1$, $Z_2$ and $R_1$ are encompassed as set forth herein.

In one embodiment, m ranges 0 to 4, n ranges from 0 to 4, p ranges from 0 to 4 and q ranges from 0 to 4. In one embodiment, m ranges 0 to 2, n ranges from 0 to 2, p ranges from 0 to 2 and q ranges from 0 to 2. In another embodiment, m is 1, n is 0, p is 0 and q is 1. In another embodiment, m is 1, n is 0, p is 1 and q is 1. In another embodiment, m is 1, n is 1, p is 0 and q is 1. In another embodiment, m is 1, n is 0, p is 0 and q is 0. In another embodiment, m is 1, n is 1, p is 1 and q is 1. In another embodiment, m is 1, n is 1, p is 0 and q is 0. In another embodiment, m is 1, n is 1, p is 1 and q is 0.

In one embodiment, $L_1$ is NH and $L_2$ is NH. In another embodiment, $L_1$ is NH and $L_2$ is a bond. In another embodiment, $L_1$ is NH and $L_2$ is —CH(NH$_2$)—. In another embodiment, $L_1$ is NH and $L_2$ is —O—. In another embodiment, $L_1$ is NH and $X_3$ is —NH—(C=O)—. In another embodiment, $L_1$ is —NH—(CH$_2$CH—OH)— and $L_2$ is a bond.

In one embodiment, X is ($C_3$-$C_{12}$)cycloalkyl. In another embodiment, X is $C_6$ cycloalkyl. In another embodiment, X is $C_6$heterocycle. In another embodiment, X is $C_5$ cycloalkyl. In another embodiment, X is $C_5$ heterocycle. In another embodiment, X is $C_4$cycloalkyl. In another embodiment, X is $C_6$ aryl. In another embodiment, X is $C_6$heterocycle. In another embodiment, X is $C_5$ heteroaryl.

In one embodiment, X is preferably selected from the group consisting of formulae (i)-(xvii):

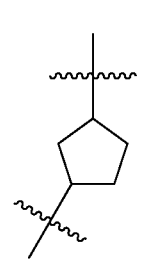 (i)

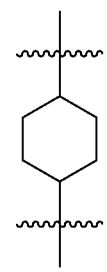 (ii)

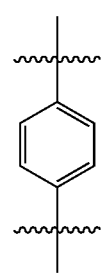 (iii)

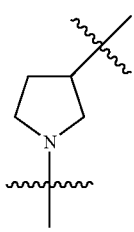 (iv)

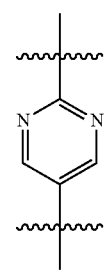 (v)

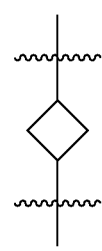 (vi)

(vii) 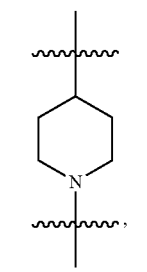

(viii) 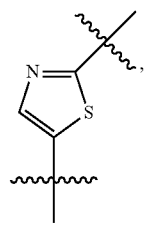

(ix) 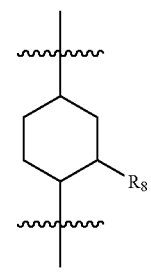

(x) 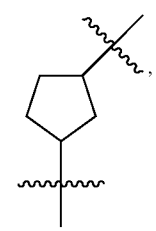

(xi) 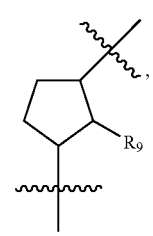

(xii) 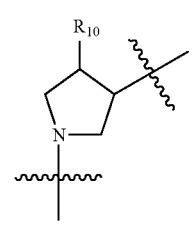

(xiii) 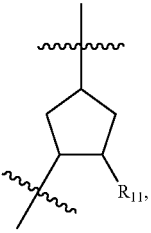

(xiv) 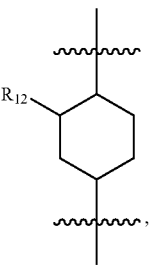

(xv) 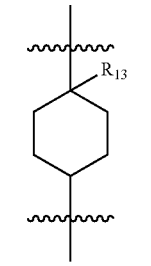

(xvi) 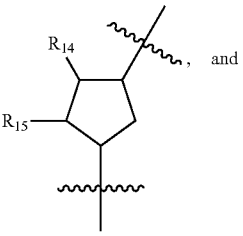, and (xvii) 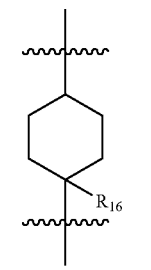

Wherein $R_8$, $R_9$, $R_{10}$, $R_{11}$, $R_{12}$, $R_{13}$ $R_{14}$, $R_{15}$ and $R_{16}$ are each individually selected from the group consisting of H, —$NR_{17}$, wherein $R_{17}$ is H or ($C_1$-$C_6$alkyl), —OH, —$(CH_2)_u$OH wherein u is an integer ranging from 1 to 6, ($C_1$-$C_6$ alkyl), ($C_1$-$C_6$ alkoxy), and halogen. In one embodiment, $R_8$, $R_9$, $R_{10}$, $R_{11}$, $R_{12}$, $R_{13}$ $R_{14}$, $R_{15}$ and $R_{16}$ are each individually selected from the group consisting of H, —OH, —$(CH_2)$OH and F. In one embodiment, $R_8$ is —OH or halogen; more preferably, —OH or F. In one embodiment, $R_9$ is —OH. In one embodiment, $R_{10}$ is —OH. In one embodiment, $R_{11}$ is —OH. In one embodiment, $R_{12}$ is OH or $CH_2$OH. In one embodiment, $R_{13}$ is OH or $CH_2$OH. In one embodiment, $R_{14}$ is —OH. In one embodiment, $R_{15}$ is —OH. In one embodiment, $R_{16}$ is OH, $CH_2OH$ or $NH_2$.
In one embodiment, X may be selected from the group consisting of:
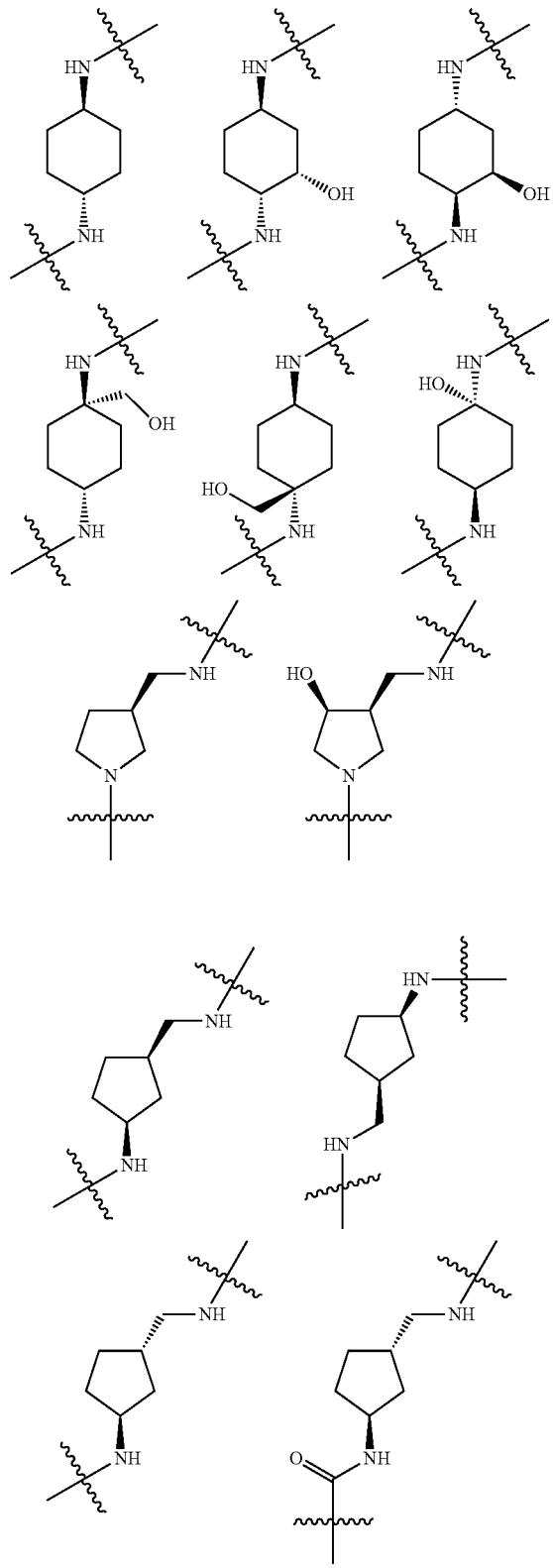
-continued
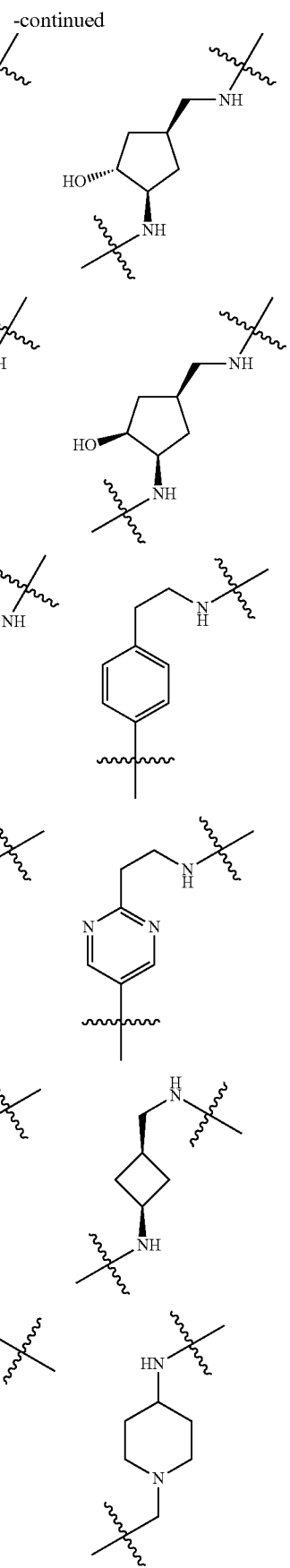

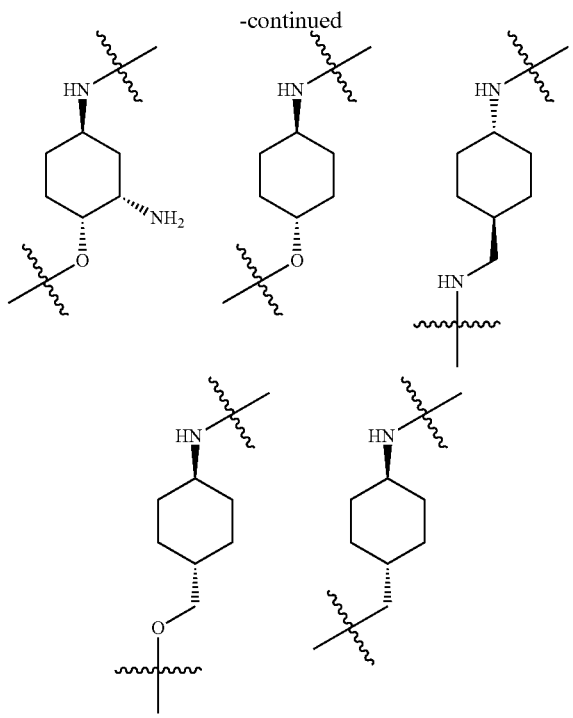

With respect to Y, in one embodiment Y is a ($C_{10}$-$C_{14}$) heteroaryl containing one, two or three heteroatoms independently selected from O, N and S, and wherein said heteroaryl is optionally substituted by one, two or three groups independently selected from the group consisting of $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, or —O—CH—($R_7$)$_2$, wherein $R_7$ is halogen. In one embodiment, Y is a 10, 11, 12, 13 or 14-membered heteroaryl containing at least one heteroatom independently selected from O, N, and S, and wherein said heteroaryl is optionally substituted by one, two or three groups independently selected from the group consisting of $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, or —O—CH—($R_7$)$_2$, wherein $R_7$ is halogen.

In one embodiment, Y may be ($C_{10}$-$C_{14}$) heteroaryl which is a fused structure with two or three rings.

In one embodiment Y is $C_{10}$ heteroaryl containing one, two or three heteroatoms selected from nitrogen, oxygen and sulfur, wherein said heteroaryl is optionally substituted by one, two, or three groups independently selected from $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, or —O—CH—($R_7$)$_2$, wherein $R_7$ is halogen. In one embodiment, Y is a fused structure with two rings.

In one embodiment, Y is $C_{10}$ heteroaryl containing one or two heteroatoms selected from N and O, wherein said heteroaryl is optionally substituted by one, two, or three groups independently selected from the group consisting of OH, $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, or —O—CH—($R_7$)$_2$, wherein $R_7$ is halogen. In such an embodiment, Y is a fused structure with two rings.

In one embodiment, Y is $C_{10}$ heteroaryl containing at least one heteroatom selected from N and O, wherein said heteroaryl is optionally substituted by one, two, or three groups selected from $C_1$-$C_6$ alkyl, $C_1$-$C_6$alkoxy, and halogen, more preferably two or three groups selected from $C_1$ alkoxy, Cl or F.

In one embodiment, Y is represented by the structure (xviii):

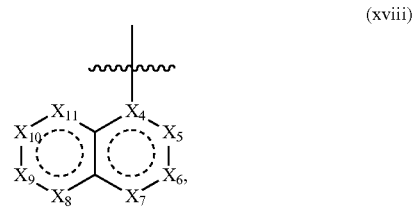

(xviii)

wherein $X_4$, $X_5$, $X_6$, $X_7$, $X_8$, $X_9$, $X_{10}$ and $X_{11}$ are each independently selected from the group consisting of C, CH, $CH_2$, N, NH and S, and wherein the groups may be optionally substituted by one or more groups selected from $C_1$-$C_6$ alkyl, $C_1$-$C_6$alkoxy, oxo, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, —O—CH—($R_7$)$_2$, wherein $R_7$ is halogen, or —N=N=N, In one embodiment, Y may be represented by the structure:

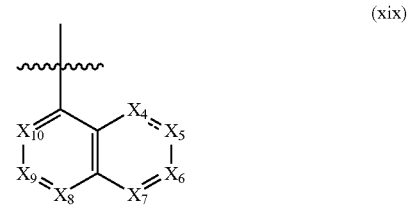

(xix)

wherein $X_6$, $X_7$, $X_8$, $X_9$, $X_{10}$ and $X_{11}$ are each independently selected from the group consisting of C, CH, and N, and wherein C may be substituted by a group selected from OH, $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen and wherein: -------
may be a double or single bond, wherein when a double bond is present, $X_4$ and $X_5$ are independently selected from C, CH, and N, and wherein C may be substituted by a group selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, —O—CH—($R_7$)$_2$, wherein $R_7$ is halogen, or —N=N=N;

and wherein when a single bond is present $X_4$ or $X_5$ are independently selected from C, CH, $CH_2$, N and NH, and wherein said C, CH and N groups may be substituted by one or more groups selected from OH, $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, —O—CH—($R_7$)$_2$, wherein $R_7$ is halogen, and —N=N=N, and wherein when $X_4$ or $X_5$ is C, it may be substituted by oxo.

In a more preferred embodiment, Y is represented by the structure (xx):

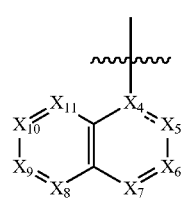
(xx)

wherein $X_6$, $X_7$, $X_8$, $X_9$, $X_{10}$ and $X_{11}$ are each independently selected from the group consisting of C, CH, and N, and wherein C may be substituted by a group selected from OH, $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, —O—CH—($R_7$)$_2$, wherein $R_7$ is halogen or —N=N=N. and wherein:

------- may be a double or single bond, wherein when a double bond is present, $X_4$ is C and $X_5$ is independently selected from C, CH, and N, and wherein C may be substituted by a group selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, —O—CH—($R_7$)$_2$, wherein $R_7$ is halogen, or —N=N=N and wherein when a single bond is present $X_4$ may be C, CH or N and $X_5$ may be C, CH, $CH_2$, N or NH, and wherein said C, CH and N groups may be substituted by one or more groups selected from OH, $C_1$-$C_6$ alkyl, $C_1$-$C_6$alkoxy, halogen, oxo, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, —O—CH—($R_7$)$_2$, wherein $R_7$ is halogen or —N=N=N, and wherein when $X_5$ is C, it may be substituted by oxo.

In another embodiment, A may be a structure selected from the group consisting of:

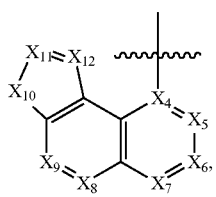
(xxi)

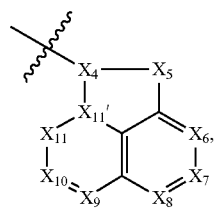
(xxii)

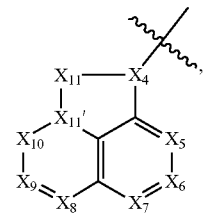
(xxiii)

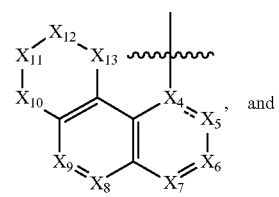
(xxiv)
, and

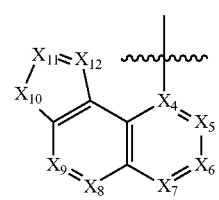
(xxv)

wherein $X_4$, $X_5$, $X_6$, $X_7$, $X_8$, $X_9$, $X_{10}$, $X_{11}$, $X_{11'}$, $X_{12}$, and $X_{13}$, are each independently selected from the group consisting of C, CH, $CH_2$, N, NH, O and S and wherein the groups may be optionally substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —OH, —CH=N—($R_6$), wherein $R_6$ is OH, ($C_1$-$C_6$)alkyl or halogen, or —O—CH—($R_7$)$_2$, wherein $R_7$ is halogen In one embodiment, Y is represented by the formula:

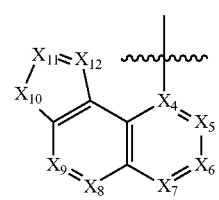
(xxi)

wherein $X_4$ is C, and $X_5$, $X_6$, $X_7$, $X_8$, $X_9$, $X_{11}$ and $X_{12}$ may independently be C, CH, or N, and wherein C is present is substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen; and wherein $X_{10}$ may be selected from C, CH, $CH_2$, N, NH, O or S, and wherein when $X_{10}$ is C, CH or N such group is substituted by one or more OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen, and wherein when $X_{10}$ is C it may be substituted by oxo. In one embodiment, $X_4$ is C, $X_5$ is C-(halogen), $X_6$ is CH, $X_7$ is N, $X_8$ is CH, $X_9$ is CH, $X_{10}$ is O, $X_{11}$ is —C—($C_1$ alkyl) and $X_{12}$ is N. More preferably, $X_4$ is C, $X_5$ is C—($C_1$), $X_6$ is CH, $X_7$ is N, $X_8$ is CH, $X_9$ is CH, $X_{10}$ is O, $X_{11}$ is —C—($C_1$ alkyl) and $X_{12}$ is N.

In one embodiment, Y is represented by the formula:

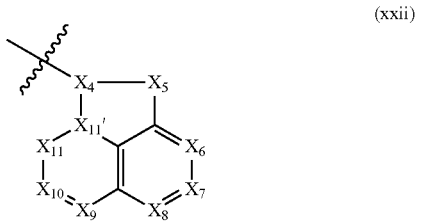

(xxii)

wherein $X_4$, $X_6$, $X_7$, $X_8$, $X_9$, $X_{10}$ and $X_{11'}$ may independently be C, CH or N, and wherein C is present is substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen; wherein $X_5$ and $X_{11}$ may be selected from C, CH, $CH_2$, N, NH, O or S, and wherein when $X_5$ or $X_{11}$ is C, CH or N, such group is substituted by one or more selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen, and wherein when $X_5$ or $X_{11}$ is C it may be substituted by oxo. In a preferred embodiment, $X_4$, $X_7$, $X_8$ and $X_{10}$ are each CH, $X_5$ is $CH_2$, $X_6$ is CF, $X_9$ and $X_{11'}$ are each N and $X_{11}$ is —C(=O).

In one embodiment, Y is represented by the formula:

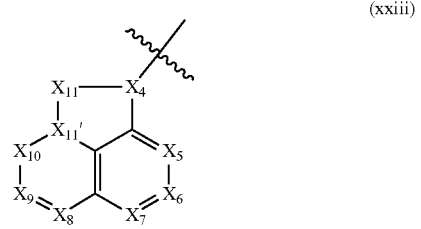

(xxiii)

wherein $X_4$, $X_5$, $X_6$, $X_7$, $X_8$, $X_9$ and $X_{11'}$ may independently be C, CH or N, and wherein C is present is substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen; wherein $X_{10}$ and $X_{11}$ may be selected from C, CH, $CH_2$, N, NH, O or S, and wherein when $X_{10}$ or $X_{11}$ is C, CH or N, such group is substituted by one or more selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen, and wherein when $X_{10}$ or $X_{11}$ is C it may be substituted by oxo. In a preferred embodiment, $X_4$ is CH, $X_5$ is C—(F), $X_6$ is CH, $X_7$ is CH, $X_8$ is N, $X_9$ is CH, $X_{10}$ is C-(oxo), $X_{11}$ is $CH_2$ and $X_{11'}$ is N.

In one embodiment, Y is represented by the formula:

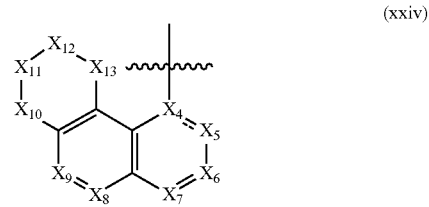

(xxiv)

wherein $X_6$, $X_7$, $X_8$ and $X_9$ may independently be C, CH or N, and wherein C is present is substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$) alkyl, —CH=N—($R_6$), wherein $R_6$ is OH, ($C_1$-$C_6$) alkyl or halogen, or —O—CH—($R_7$)$_2$, wherein $R_7$ is halogen; and wherein $X_{10}$, $X_{11}$, $X_{12}$ and $X_{13}$ may be selected from C, CH, $CH_2$, N, NH, O or S, and wherein when $X_{10}$, $X_{11}$, $X_{12}$ or $X_{13}$ is C, CH or N, such group is substituted by one or more selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen, and wherein when $X_{10}$, $X_{11}$, $X_{12}$ or $X_{13}$ is C it may be substituted by oxo.

wherein: ------- may be a double or single bond, wherein when a double bond is present, $X_4$ is C and $X_5$ is independently selected from C, CH, and N, and wherein C may be substituted by a group selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen;

and wherein when a single bond is present $X_4$ may be C, CH or N and $X_5$ may be C, CH, $CH_2$, N or NH, and wherein said C, CH and N groups may be substituted by one or more groups selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen and wherein when $X_5$ is C, it may be substituted by oxo. In a preferred embodiment, when ------- is present as a double bond, $X_4$ is C, $X_5$ is CH-(halogen), $X_6$ is CH, $X_7$ is CH, $X_8$ is N, $X_9$ is CH, $X_{10}$ is O, $X_{11}$ is $CH_2$, $X_{12}$ is $CH_2$ and $X_{13}$ is O. More preferably, $X_4$ is C, $X_5$ is C—(fluoro), $X_6$ is CH, $X_7$ is CH, $X_8$ is N, $X_9$ is CH, $X_{10}$ is O, $X_{11}$ is $CH_2$, $X_{12}$ is $CH_2$ and $X_{13}$ is O; and when present as a single bond, $X_4$ is N, $X_5$ is C—(=O), $X_6$ is CH, $X_7$ is CH, $X_8$ is N, $X_9$ is CH, $X_{10}$ is O, $X_{11}$ is $CH_2$, $X_{12}$ is $CH_2$ and $X_{13}$ is O.

In one embodiment, Y is represented by the formula:

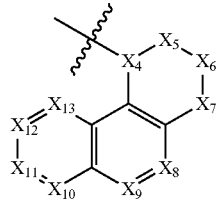

(xxv)

wherein $X_4$, $X_8$, $X_9$, $X_{11}$, $X_{12}$ and $X_{13}$ may independently be C, CH or N, and wherein when C is present is substituted by OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and R are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen; and wherein $X_5$, $X_6$, and $X_7$ may be selected from C, CH, $CH_2$, N, NH, O or S, and wherein when $X_5$, $X_6$ or $X_7$ is C, CH or N, such group is substituted by one or more selected from OH, $C_1$-$C_6$ alkyl, $C_1$-$C_6$alkoxy, halogen, ($C_1$-$C_6$ alkyl)$NR_4R_5$, O—($C_1$-$C_6$alkyl)-$NR_4R_5$, wherein $R_4$ and $R_5$ are each independently selected from H or ($C_1$-$C_6$)alkyl, —CH=N—($R_6$), wherein $R_6$ is OH, ($C_1$-$C_6$)alkyl or halogen, or —O—CH—($R_7$)$_2$, wherein $R_7$ is halogen, and wherein when $X_5$, $X_6$ or $X_7$ is C it may be substituted by oxo.

In a preferred embodiment, $X_4$ is $CH_2$, $X_5$ is $CH_2$, $X_6$ is $CH_2$, $X_7$ is O, $X_8$ is CH, $X_9$ is CH, $X_{10}$ is N, $X_{11}$ is CH, $X_{12}$ is C—($C_1$-$C_6$ alkoxy) and $X_{13}$ is CH. More preferably, $X_{12}$ is —C ($C_1$alkoxy)

In various embodiments, Y may be selected from the group:

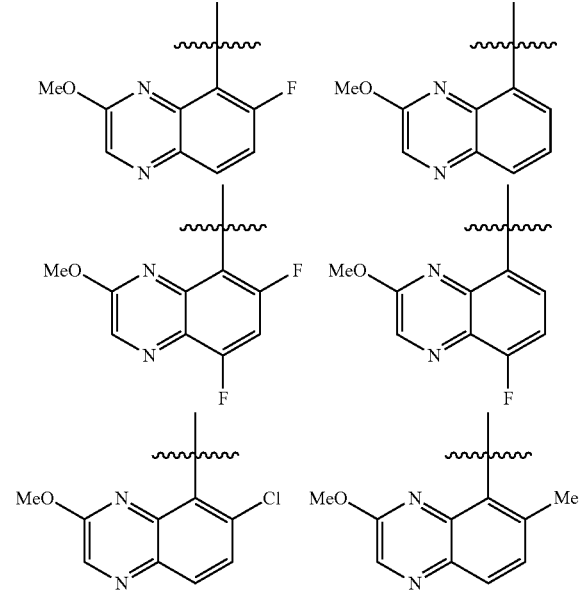

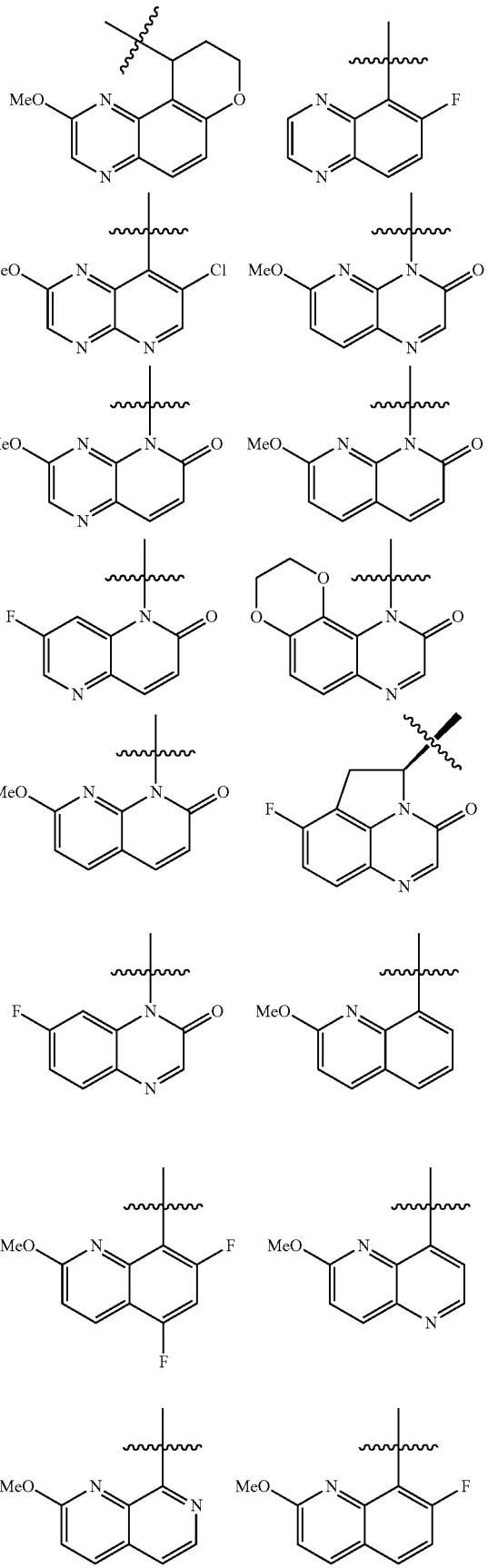

-continued

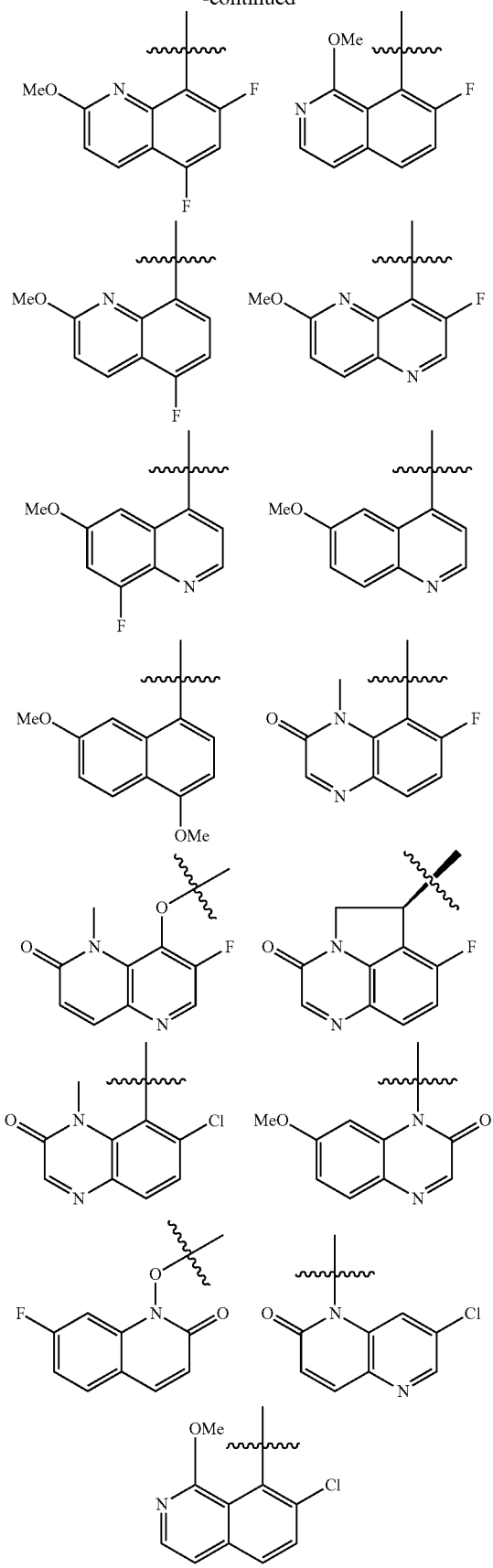

In another aspect, the invention provides a compound of the formula (II):

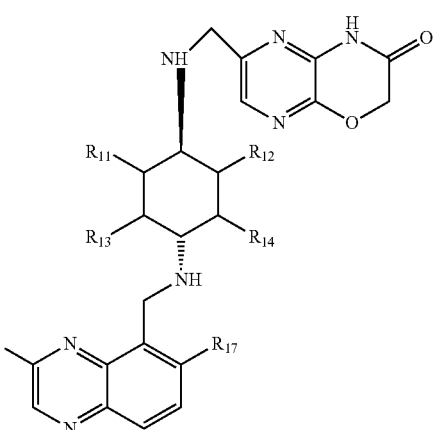

(II)

wherein $R_{29}$ is selected from the group consisting of H, CH=O, and $(C_1$-$C_6)$alkyl;

X is selected from $(C_3$-$C_{12})$cycloalkyl or $(C_2$-$C_9)$heterocycle:

$R_{30}$ is selected from H, CH=O or $(C_1$-$C_6)$alkyl; and

Y is defined as set forth hereinabove, along with pharmaceutically acceptable salts, solvates or N-oxides thereof.

In another aspect, the invention provides a compound of the formula (III):

(III)

wherein $R_{11}$, $R_{12}$, $R_{13}$, $R_{14}$, $R_{16}$ and $R_{17}$ are independently selected from H, $(C_1$-$C_6)$ alkyl, OH, $(C_1$-$C_6)$ alkoxy and halogen, along with pharmaceutically acceptable salts, solvates or N-oxides thereof.

In a preferred embodiment, $R_{11}$, $R_{12}$, $R_{13}$, $R_{14}$, $R_{16}$ and $R_{17}$ are independently selected from H, $C_1$alkyl, OH, $C_1$alkoxy, Cl and F.

In another aspect, the invention provides a compound of the formula (IV):

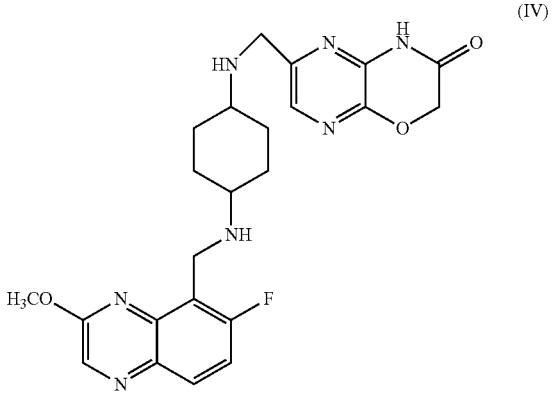 [SMILES: COc1cnc2ccc(F)c(CNC3CCC(NCc4cnc5c(n4)NC(=O)CO5)CC3)c2n1]

(IV)

along with pharmaceutically acceptable salts, solvates, and N-oxides thereof, as well as other forms set forth herein. A particularly preferred salt is the hydrochloride salt.

In another aspect, the invention provides a compound of formula (V):

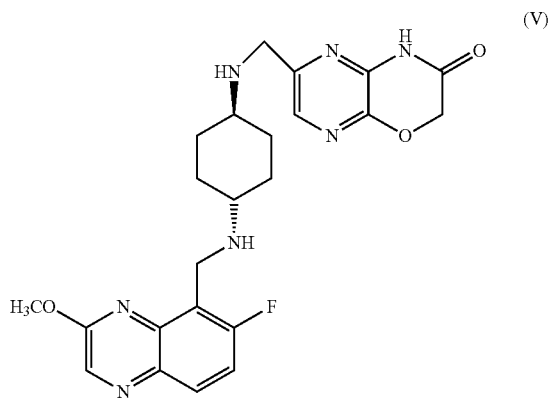

(V)

The compound of formula (V) is 6-((((1R,4R)-4-(((6-fluoro-3-methoxyquinoxalin-5-yl)methyl)amino) cyclohexyl)amino)methyl)-2H-pyrazino[2,3-b][1,4]oxazin-3(4H)-one, along with pharmaceutically acceptable salts, solvates, and N-oxides thereof, as well as other forms set forth herein. A particularly preferred salt is the hydrochloride salt.

In another aspect, the invention provides a compound of formula (VI):

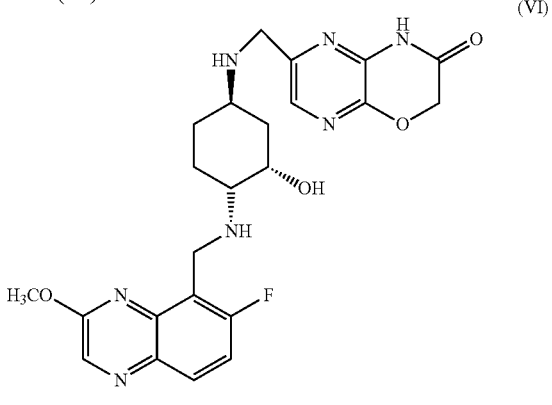

(VI)

The compound of formula (VI) is 6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one, along with pharmaceutically acceptable salts, solvates, and N-oxides thereof, as well as other forms set forth herein. A particularly preferred salt is the hydrochloride salt.

In another aspect, the invention provides a compound of formula (VII):

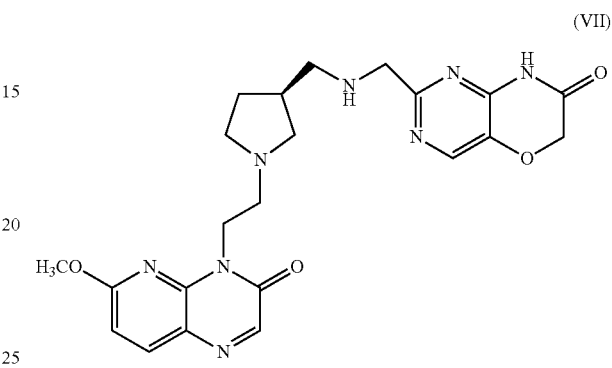

(VII)

The compound of formula (VII) is 2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one, along with pharmaceutically acceptable salts, solvates, and N— oxides thereof, as well as other forms set forth herein. Preferred forms for the compound of formula (VII) are mono tosylate and HBr salts, most preferably each are present in crystalline form.

In another aspect, the compounds of the present invention include the following set forth below. Numbers for the compounds are set forth with each that is listed:

1. 6-((((1R,4R)-4-(((6-fluoro-3-methoxyquinoxalin-5-yl)methyl)amino) cyclohexyl)amino)methyl)-2H-pyrazino[2,3-b][1,4]oxazin-3(4H)-one
2. 6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one
3. 2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one
4. 6-({[(1R,4R)-4-{[(6-methoxy-1,5-naphthyridin-4-yl)methyl]amino}cyclohexyl]amino}methyl)-2H,3H,4H-pyrazino[2,3-b][1,4]thiazin-3-one
5. 6-({[(1R,4R)-4-{[(3-methoxyquinoxalin-5-yl)methyl]amino}cyclohexyl]amino}methyl)-2H,3H,4H-pyrazino[2,3-b][1,4]thiazin-3-one
6. 6-{[(2-{4-[3-(2-aminoethoxy)-6-fluoroquinoxalin-5-yl]phenyl}ethyl)amino]methyl}-2H,3H,4H-pyrazino[2,3-b][1,4]thiazin-3-one
7. 6-({[(1R,4R)-4-{[(6,8-difluoro-3-methoxyquinoxalin-5-yl)methyl]amino}cyclohexyl]amino}methyl)-2H,3H,4H-pyrazino[2,3-b][1,4]thiazin-3-one
8. 6-({[(1R,4R)-4-{[(2-methoxyquinolin-8-yl)methyl]amino}cyclohexyl]amino}methyl)-2H,3H,4H-pyrazino[2,3-b][1,4]thiazin-3-one
9. 6-{[(2-{4-[6-(2-aminoethoxy)-3-fluoro-1,5-naphthyridin-4-yl]phenyl}ethyl)amino]methyl}-2H,3H,4H-pyrazino[2,3-b][1,4]thiazin-3-one 10. 6-({[(1R,4R)-4-{[(6-fluoro-3-methoxyquinoxalin-5-yl)methyl]amino}cyclohexyl]amino}methyl)-2H,3H,4H-pyrazino[2,3-b][1,4]thiazin-3-one
11. 6-({[(1R,4R)-4-{[(5-fluoro-2-methoxyquinolin-8-yl)methyl]amino}cyclohexyl]amino}methyl)-2H,3H,4H-pyrazino[2,3-b][1,4]thiazin-3-one
12. 6-({[(1R,4R)-4-{[(5,7-difluoro-2-methoxyquinolin-8-yl)methyl]amino}cyclohexyl]amino}methyl)-2H,3H,4H-pyrazino[2,3-b][1,4]thiazin-3-one
13. 6-({[(1S,4R)-4-{2-[6-(2-aminoethoxy)-3-fluoro-1,5-naphthyridin-4-yl]ethyl}cyclohexyl]amino}methyl)-2H,3H,4H-pyrazino[2,3-b][1,4]thiazin-3-one
14. 6-({[(1R,4R)-4-[({6-fluoro-3-[(1E)-(hydroxyimino)methyl]quinoxalin-5-yl}methyl)amino]cyclohexyl]amino}methyl)-2H,3H,4H-pyrazino[2,3-b][1,4]thiazin-3-one
15. 6-({[(1R,4R)-4-{[(8-fluoro-3-methoxy quinoxalin-5-yl)methyl]amino}cyclohexyl]amino}methyl)-2H,3H,4H-pyrazino[2,3-b][1,4]thiazin-3-one
16. 6-({[(1R,4R)-4-{[(6-chloro-3-methoxyquinoxalin-5-yl)methyl]amino}cyclohexyl]amino}methyl)-2H,3H,4H-pyrazino[2,3-b][1,4]thiazin-3-one
17. 6-({[(1R,3S,4R)-4-{[(6-fluoro-3-methoxyquinoxalin-5-yl)methyl]amino}-3-hydroxycyclohexyl]amino}methyl)-2H,3H,4H-pyrazino[2,3-b][1,4]thiazin-3-one
18. 6-({[(1R,3S,4R)-3-hydroxy-4-{[(6-methoxy-1,5-naphthyridin-4-yl)methyl]amino}cyclohexyl]amino}methyl)-2H,3H,4H-pyrazino[2,3-b][1,4]thiazin-3-one
19. 6-({[(1S,3R,4S)-3-hydroxy-4-{[(6-methoxy-1,5-naphthyridin-4-yl)methyl]amino}cyclohexyl]amino}methyl)-2H,3H,4H-pyrazino[2,3-b][1,4]thiazin-3-one
20. 6-({[(1R,3S,4R)-3-hydroxy-4-{[(3-methoxy-6-methylquinoxalin-5-yl)methyl]amino}cyclohexyl]amino}methyl)-2H,3H,4H-pyrazino[2,3-b][1,4]thiazin-3-one
21. 6-methoxy-4-{2-[(3S)-3-{[({3-oxo-2H,3H,4H-pyrazino[2,3-b][1,4]thiazin-6-yl}methyl)amino]methyl}pyrrolidin-1-yl]ethyl}-3H,4H-pyrido[2,3-b]pyrazin-3-one
22. 6-({[(1R,4R)-4-({2-methoxy-8H,9H,10H-pyrano[3,2-f]quinoxalin-10-yl}amino)cyclohexyl]amino}methyl)-2H,3H,4H-pyrazino[2,3-b][1,4]thiazin-3-one
23. 1-(2-aminoethyl)-7-fluoro-8-{[(1r,4r)-4-[({3-oxo-2H,3H,4H-pyrazino[2,3-b][1,4]thiazin-6-yl}methyl)amino]cyclohexyl]methoxy}-1,2-dihydroquinoxalin-2-one
24. 6-({[(1R,4R)-4-{[(6-fluoro-3-methoxyquinoxalin-5-yl)methyl]amino}-1-(hydroxymethyl)cyclohexyl]amino}methyl)-2H,3H,4H-pyrazino[2,3-b][1,4]thiazin-3-one
25. 7-methoxy-1-{2-[(3S)-3-{[({3-oxo-2H,3H,4H-pyrazino[2,3-b][1,4]thiazin-6-yl}methyl)amino]methyl}pyrrolidin-1-yl]ethyl]ethy}-1,2-dihydro-1,8-naphthyridin-2-one
26. 1-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-7-methoxy-1,2-dihydro-1,8-naphthyridin-2-one
27. 6-[({2-[5-(6-fluoro-3-methoxy quinoxalin-5-yl)pyrimidin-2-yl]ethyl}amino)methyl]-2H,3H,4H-pyrazino[2,3-b][1,4]thiazin-3-one
28. 3-methoxy-5-{2-[(3S)-3-{[({3-oxo-2H,3H,4H-pyrazino[2,3-b][1,4]thiazin-6-yl}methyl)amino]methyl}pyrrolidin-1-yl]ethyl}-5H,6H-pyrido[2,3-b]pyrazin-6-one
29. 7-fluoro-1-{2-[(3S)-3-{[({3-oxo-2H,3H,4H-pyrazino[2,3-b][1,4]thiazin-6-yl}methyl)amino]methyl}pyrrolidin-1-yl]ethyl}-1,2-dihydro-1,5-naphthyridin-2-one
30. 6-({[(1R,4R)-4-({[3-(2-aminoethoxy)-6-fluoroquinoxalin-5-yl]amino}methyl)cyclohexyl]amino}methyl)-2H,3H,4H-pyrazino[2,3-b][1,4]thiazin-3-one
31. 6-[({[(3S,4S)-4-hydroxy-1-[2-(3-methoxyquinoxalin-5-yl)ethyl]pyrrolidin-3-yl]methyl}amino)methyl]-2H,3H,4H-pyrazino[2,3-b][1,4]thiazin-3-one
32. 6-methoxy-4-{2-[(1R,4R)-4-[({3-oxo-2H,3H,4H-pyrazino[2,3-b][1,4]thiazin-6-yl}methyl)amino]cyclohexyl]ethyl}-3H,4H-pyrido[2,3-b]pyrazin-3-one
33. 6-({[(1R,4R)-4-{[(2-methoxy-1,7-naphthyridin-8-yl)methyl]amino}cyclohexyl]amino}methyl)-2H,3H,4H-pyrazino[2,3-b][1,4]thiazin-3-one
34. 6-({[(1R,4R)-4-{[(3-fluoro-6-methoxy-1,5-naphthyridin-4-yl)methyl]amino}cyclohexyl]amino}methyl)-2H,3H,4H-pyrazino[2,3-b][1,4]thiazin-3-one
35. 6-({[(1R,4R)-4-({[6-(2-aminoethoxy)-3-fluoro-1,5-naphthyridin-4-yl]oxy}methyl)cyclohexyl]amino}methyl)-2H,3H,4H-pyrazino[2,3-b][1,4]thiazin-3-one
36. 6-fluoro-3-methoxy-5-({[(1R,4R)-4-[({3-oxo-2H,3H,4H-pyrazino[2,3-b][1,4]thiazin-6-yl}methyl)amino]cyclohexyl]amino}methyl)-1$\lambda^5$,4-quinoxalin-1-one
37. 6-({[(1R,4R)-4-{[(7-fluoro-2-methoxyquinolin-8-yl)methyl]amino}-1-(hydroxymethyl)cyclohexyl]amino}methyl)-2H,3H,4H-pyrazino[2,3-b][1,4]thiazin-3-one
38. 6-({[(1R,4R)-4-{[(7-fluoro-2-methoxyquinolin-8-yl)methyl]amino}-4-(hydroxymethyl)cyclohexyl]amino}methyl)-2H,3H,4H-pyrazino[2,3-b][1,4]thiazin-3-one
39. 6-methoxy-N-[(1R,4R)-4-[({3-oxo-2H,3H,4H-pyrazino[2,3-b][1,4]thiazin-6-yl}methyl)amino]cyclohexyl]-1,5-naphthyridine-4-carboxamide
40. 6-[({[(1R,3S)-3-{[(6-fluoro-3-methoxyquinoxalin-5-yl)methyl]amino}cyclopentyl]methyl}amino)methyl]-2H,3H,4H-pyrazino[2,3-b][1,4]thiazin-3-one
41. 6-({[(1R,3S)-3-({[(6-fluoro-3-methoxyquinoxalin-5-yl)methyl]amino}methyl)cyclopentyl]amino}methyl)-2H,3H,4H-pyrazino[2,3-b][1,4]thiazin-3-one
42. 6-[({[(3S)-1-(2-{9-oxo-2H,3H,9H,10H-[1,4]dioxino[2,3-f]quinoxalin-10-yl}ethyl)pyrrolidin-3-yl]methyl}amino)methyl]-2H,3H,4H-pyrazino[2,3-b][1,4]thiazin-3-one
43. 6-[({[(3S)-1-[2-(6-fluoro-3-methoxyquinoxalin-5-yl)ethyl]pyrrolidin-3-yl]methyl}amino)methyl]-2H,3H,4H-pyrazino[2,3-b][1,4]thiazin-3-one
44. 6-[({[(1S,3 S)-3-{[(6-fluoro-3-methoxyquinoxalin-5-yl)methyl]amino}cyclopentyl]methyl}amino)methyl]-2H,3H,4H-pyrazino[2,3-b][1,4]thiazin-3-one
45. 6-fluoro-5-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-3-methoxy-1,4-quinoxalin-1-one
46. 6-({[(1R,4R)-4-{[(5,7-difluoro-2-methoxyquinolin-8-yl)methyl]amino}-1-(hydroxymethyl)cyclohexyl]amino}methyl)-2H,3H,4H-pyrazino[2,3-b][1,4]thiazin-3-one
47. 6-({[(1R,2S,4R)-4-{[(6-fluoro-3-methoxyquinoxalin-5-yl)methyl]amino}-2-hydroxycyclohexyl]amino}methyl)-2H,3H,4H-pyrazino[2,3-b][1,4]thiazin-3-one
48. 3-methoxy-5-({[(1R,4R)-4-[({3-oxo-2H,3H,4H-pyrazino[2,3-b][1,4]thiazin-6-yl}methyl)amino]cyclohexyl]amino}methyl)-1$\lambda^5$,4-quinoxalin-1-one
49. 6-({[(1R,4R)-4-{[(10S)-2-methoxy-8H,9H,10H-pyrano[3,2-f]quinoxalin-10-yl]amino}cyclohexyl]amino}methyl)-2H,3H,4H-pyrazino[2,3-b][1,4]thiazin-3-one 50. 6-[({[(1R,3R,4S)-3-{[(3-fluoro-6-methoxy-1,5-naphthyridin-4-yl)methyl]amino}-4-hydroxycyclopentyl]methyl}amino)methyl]-2H,3H,4H-pyrazino[2,3-b][1,4]thiazin-3-one
51. 6-({[(1R,3S,4R)-4-{[(7-fluoro-1-methoxyisoquinolin-8-yl)methyl]amino}-3-hydroxycyclohexyl]amino}methyl)-2H,3H,4H-pyrazino[2,3-b][1,4]thiazin-3-one
52. 7-fluoro-8-({[(1S,2R,4S)-2-hydroxy-4-[({3-oxo-2H,3H,4H-pyrazino[2,3-b][1,4]thiazin-6-yl}methyl)amino]cyclohexyl]amino}methyl)-1-methyl-1,2-dihydroquinoxalin-2-one
53. 6-[({[(1R,3R)-3-{[(6-fluoro-3-methoxyquinoxalin-5-yl)methyl]amino}cyclobutyl]methyl}amino)methyl]-2H,3H,4H-pyrazino[2,3-b][1,4]thiazin-3-one
54. 6-({[(1R,4R)-4-[({3-fluoro-6-[(1E)-(hydroxyimino)methyl]-1,5-naphthyridin-4-yl}methyl)amino]cyclohexyl]amino}methyl)-2H,3H,4H-pyrazino[2,3-b][1,4]thiazin-3-one
55. 6-({[(1R,2S,4R)-4-{[(6-fluoro-3-methoxyquinoxalin-5-yl)methyl]amino}-2-hydroxycyclohexyl]amino}methyl)-2H,3H,4H-pyrazino[2,3-b][1,4]thiazin-3-one
56. 6-[({[(1S,3R,4S)-3-{[(3-fluoro-6-methoxy-1,5-naphthyridin-4-yl)methyl]amino}-4-hydroxycyclopentyl]methyl}amino)methyl]-2H,3H,4H-pyrazino[2,3-b][1,4]thiazin-3-one
57. 6-[({[(1R,2S,3R,4R)-2,3-dihydroxy-4-({2-methoxy-8H,9H,10H-pyrano[3,2-f]quinoxalin-10-yl}amino)cyclopentyl]methyl}amino)methyl]-2H,3H,4H-pyrazino[2,3-b][1,4]thiazin-3-one
58. 4-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-6-methoxy-3H,4H-pyrido[2,3-b]pyrazin-3-one
59. (2S)-5-fluoro-2-({4-[({3-oxo-2H,3H,4H-pyrazino[2,3-b][1,4]thiazin-6-yl}methyl)amino]piperidin-1-yl}methyl)-1,9-diazatricyclo[6.3.1.0,$^{4,12}$]dodeca-4(12),5,7,9-tetraen-11-one
60. 6-({[(1R,4R)-4-{[(6-fluoro-3-methoxyquinoxalin-5-yl)methyl]amino}-1-(hydroxymethyl)cyclohexyl]amino}methyl)-2H,3H,4H-pyrazino[2,3-b][1,4]thiazin-3-one
61. 7-fluoro-1-methyl-8-{[(1R,4R)-4-[({3-oxo-2H,3H,4H-pyrazino[2,3-b][1,4]thiazin-6-yl}methyl)amino]cyclohexyl]methoxy}-1,2-dihydro-1,5-naphthyridin-2-one
62. 6-[({[(3 S)-1-(2-{6-[2-(dimethylamino)ethoxy]-3-fluoro-1,5-naphthyridin-4-yl}ethyl)pyrrolidin-3-yl]methyl}amino)methyl]-2H,3H,4H-pyrazino[2,3-b][1,4]thiazin-3-one
63. 6-[({[(3 S)-1-(2-{6-[2-(dimethylamino)ethoxy]-3-fluoro-1,5-naphthyridin-4-yl}ethyl)pyrrolidin-3-yl]methyl}amino)methyl]-2H,3H,4H-pyrazino[2,3-b][1,4]thiazin-3-one
64. 6-({[(1R,4R)-4-{[(6-fluoro-3-methoxyquinoxalin-5-yl)methyl]amino}-4-(hydroxymethyl)cyclohexyl]amino}methyl)-2H,3H,4H-pyrazino[2,3-b][1,4]thiazin-3-one
65. 6-({[(1R,4R)-4-{[(6-methoxy quinolin-4-yl)methyl]amino}cyclohexyl]amino}methyl)-2H,3H,4H-pyrazino[2,3-b][1,4]thiazin-3-one
66. 7-fluoro-1-{2-[(3S)-3-{[({3-oxo-2H,3H,4H-pyrazino[2,3-b][1,4]thiazin-6-yl}methyl)amino]methyl}pyrrolidin-1-yl]ethyl}-1,2-dihydroquinoxalin-2-one
67. 6-({[(1R,4R)-4-{[(8-fluoro-6-methoxyquinolin-4-yl)methyl]amino}cyclohexyl]amino}methyl)-2H,3H,4H-pyrazino[2,3-b][1,4]thiazin-3-one
68. 6-({[(1R,4R)-4-{[(3-fluoro-6-methoxy-1,5-naphthyridin-4-yl)methyl]amino}-1-(hydroxymethyl)cyclohexyl]amino}methyl)-2H,3H,4H-pyrazino[2,3-b][1,4]thiazin-3-one
69. 6-[({2-[5-(6-fluoro-3-methoxyquinoxalin-5-yl)-1,3-thiazol-2-yl]ethyl}amino)methyl]-2H,3H,4H-pyrazino[2,3-b][1,4]thiazin-3-one
70. 7-methoxy-1-{2-[(3S)-3-{[({3-oxo-2H,3H,4H-pyrazino[2,3-b][1,4]thiazin-6-yl}methyl)amino]methyl}pyrrolidin-1-yl]ethyl}-1,2-dihydroquinoxalin-2-one
71. 6-[({[(3S)-1-[2-(3-methoxyquinoxalin-5-yl)ethyl]pyrrolidin-3-yl]methyl}amino)methyl]-2H,3H,4H-pyrazino[2,3-b][1,4]thiazin-3-one
72. 6-({[(1R,4R)-4-{[(3-fluoro-6-methoxy-1,5-naphthyridin-4-yl)methyl]amino}-4-(hydroxymethyl)cyclohexyl]amino}methyl)-2H,3H,4H-pyrazino[2,3-b][1,4]thiazin-3-one
73. 6-({[(1R,4R)-1-(hydroxymethyl)-4-({2-methoxy-8H,9H,10H-pyrano[3,2-f]quinoxalin-10-yl}amino)cyclohexyl]amino}methyl)-2H,3H,4H-pyrazino[2,3-b][1,4]thiazin-3-one
74. (3R)-5-fluoro-3-({4-[({3-oxo-2H,3H,4H-pyrazino[2,3-b][1,4]thiazin-6-yl}methyl)amino]piperidin-1-yl}methyl)-1,9-diazatricyclo[6.3.1.0,$^{4,12}$]dodeca-4,6,8(12),9-tetraen-11-one
75. 6-[({2-[4-(6-fluoro-3-methoxyquinoxalin-5-yl)phenyl]-2-hydroxyethyl}amino)methyl]-2H,3H,4H-pyrazino[2,3-b][1,4]thiazin-3-one
76. 6-[({[(3S,4S)-1-(2-{2-[2-(dimethylamino)ethoxy]-7-fluoroquinolin-8-yl}ethyl)-4-hydroxypyrrolidin-3-yl]methyl}amino)methyl]-2H,3H,4H-pyrazino[2,3-b][1,4]thiazin-3-one
77. 3-fluoro-6-methoxy-4-({[(1R,4R)-4-[({3-oxo-2H,3H,4H-pyrazino[2,3-b][1,4]thiazin-6-yl}methyl)amino]cyclohexyl]amino}methyl)-1$\lambda^5$,5-1,5-naphthyridin-1-one
78. 3-fluoro-6-methoxy-4-{2-[(3S)-3-{[({3-oxo-2H,3H,4H-pyrazino[2,3-b][1,4]thiazin-6-yl}methyl)amino]methyl}pyrrolidin-1-yl]ethyl}-1$\lambda^5$,5-1,5-naphthyridin-1-one
79. 6-({[(1R,4R)-4-{[(4,7-dimethoxynaphthalen-1-yl)methyl]amino}cyclohexyl]amino}methyl)-2H,3H,4H-pyrazino[2,3-b][1,4]thiazin-3-one
80. 6-fluoro-3-methoxy-5-{2-[(3S)-3-{[({3-oxo-2H,3H,4H-pyrazino[2,3-b][1,4]thiazin-6-yl}methyl)amino]methyl}pyrrolidin-1-yl]ethyl}-1$\lambda^5$,4-quinoxalin-1-one
81. 7-methoxy-1-(2-{4-[({3-oxo-2H,3H,4H-pyrazino[2,3-b][1,4]thiazin-6-yl}methyl)amino]piperidin-1-yl}ethyl)-1,2-dihydro-1,8-naphthyridin-2-one
82. 7-fluoro-1-(2-{4-[({3-oxo-2H,3H,4H-pyrazino[2,3-b][1,4]thiazin-6-yl}methyl)amino]piperidin-1-yl}ethyl)-1,2-dihydroquinoxalin-2-one
83. 6-({[(1S,3S)-3-({[(6-fluoro-3-methoxyquinoxalin-5-yl)methyl]amino}methyl)cyclopentyl]amino}methyl)-2H,3H,4H-pyrazino[2,3-b][1,4]thiazin-3-one
84. 6-({[1-(2-{6-fluoro-3-[(hydroxyimino)methyl]quinoxalin-5-yl}ethyl)piperidin-4-yl]amino}methyl)-2H,3H,4H-pyrazino[2,3-b][1,4]thiazin-3-one
85. 7-fluoro-1-methyl-8-({[(1R,4R)-4-[({3-oxo-2H,3H,4H-pyrazino[2,3-b][1,4]thiazin-6-yl}methyl)amino]cyclohexyl]amino}methyl)-1,2-dihydroquinoxalin-2-one
86. 2-methoxy-10-{[(1R,4R)-4-({[{3-oxo-2H,3H,4H-pyrazino[2,3-b][1,4]thiazin-6-yl}methyl)amino]cyclohexyl]amino}-8H,9H,10H-7,1,4$\lambda^5$-pyrano[3,2-f]quinoxalin-4-one 87. 3-chloro-6-methoxy-4-{2-[(3 S)-3-{[({3-oxo-2H,3H,4H-pyrazino[2,3-b][1,4]thiazin-6-yl}methyl)amino]methyl}pyrrolidin-1-yl]ethyl}-1λ⁵,5-1,5-naphthyridin-1-one 88. 7-chloro-1-{2-[(3S)-3-{[({3-oxo-2H,3H,4H-pyrazino[2,3-b][1,4]thiazin-6-yl}methyl)amino]methyl}pyrrolidin-1-yl]ethyl}-1,2-dihydro-1,5-naphthyridin-2-one 89. 1-methyl-8-({[(1R,4R)-4-[({3-oxo-2H,3H,4H-pyrazino[2,3-b][1,4]thiazin-6-yl}methyl)amino]cyclohexyl]amino}methyl)-1,2-dihydroquinoxalin-2-one 90. 6-({[(1R,4R)-4-{[(6,8-difluoro-3-methoxyquinoxalin-5-yl)methyl]amino}-1-(hydroxymethyl)cyclohexyl]amino}methyl)-2H,3H,4H-pyrazino[2,3-b][1,4]thiazin-3-one 91. 6-({[(1R,4R)-4-{[(6,8-difluoro-3-methoxyquinoxalin-5-yl)methyl]amino}-4-(hydroxymethyl)cyclohexyl]amino}methyl)-2H,3H,4H-pyrazino[2,3-b][1,4]thiazin-3-one 92. 6-({[(1R,4R)-4-{[(5,7-difluoro-2-methoxyquinolin-8-yl)methyl]amino}-4-(hydroxymethyl)cyclohexyl]amino}methyl)-2H,3H,4H-pyrazino[2,3-b][1,4]thiazin-3-one 93. 3-methoxy-N-[(1R,3R)-3-{[({3-oxo-2H,3H,4H-pyrazino[2,3-b][1,4]thiazin-6-yl}methyl)amino]methyl}cyclopentyl]quinoxaline-5-carboxamide 94. 6-({[(1r,4r)-4-{[(10S)-2-methoxy-8H,9H,10H-pyrano[3,2-f]quinoxalin-10-yl]amino}cyclohexyl]amino}methyl)-2H,3H,4H-pyrazino[2,3-b][1,4]thiazin-3-one 95. 6-[({[(1R,3R,4S)-3-{[(3-fluoro-6-methoxy-1,5-naphthyridin-4-yl)methyl]amino}-4-hydroxycyclopentyl]methyl}amino)methyl]-2H,3H,4H-pyrazino[2,3-b][1,4]thiazin-3-one 96. 6-[({[(1R,3R,4S)-3-{[(3-fluoro-6-methoxy-1,5-naphthyridin-4-yl)methyl]amino}-4-hydroxycyclopentyl]methyl}amino)methyl]-2H,3H,4H-pyrazino[2,3-b][1,4]thiazin-3-one 97. 6-({[(1R,4R)-4-{[(7-fluoro-1-methoxyisoquinolin-8-yl)methyl]amino}cyclohexyl]amino}methyl)-2H,3H,4H-pyrazino[2,3-b][1,4]thiazin-3-one 98. 6-[({[(3S,4S)-1-[2-(3-chloro-5-methoxy-1,6-naphthyridin-4-yl)ethyl]-4-hydroxypyrrolidin-3-yl]methyl}amino)methyl]-2H,3H,4H-pyrazino[2,3-b][1,4]thiazin-3-one 99. 6-[({[(1S,3 S)-3-{[(6-fluoro-3-methoxyquinoxalin-5-yl)methyl]amino}cyclobutyl]methyl}amino)methyl]-2H,3H,4H-pyrazino[2,3-b][1,4]thiazin-3-one 100. 6-({[(1R,4R)-4-{[(6-fluoroquinoxalin-5-yl)methyl]amino}cyclohexyl]amino}methyl)-2H,3H,4H-pyrazino[2,3-b][1,4]thiazin-3-one 101. 6-[({[(1S,2S,3S)-3-{[(3-fluoro-6-methoxy-1,5-naphthyridin-4-yl)methyl]amino}-2-hydroxycyclopentyl]methyl}amino)methyl]-2H,3H,4H-pyrazino[2,3-b][1,4]thiazin-3-one 102. 7-fluoro-1-methyl-8-[({[(1S,3S)-3-[({3-oxo-2H,3H,4H-pyrazino[2,3-b][1,4]thiazin-6-yl}methyl)amino]cyclopentyl]methyl}amino)methyl]-1,2-dihydroquinoxalin-2-one 103. 7-fluoro-1-methyl-8-({[(1S,3R)-3-{[({3-oxo-2H,3H,4H-pyrazino[2,3-b][1,4]thiazin-6-yl}methyl)amino]methyl}cyclopentyl]amino}methyl)-1,2-dihydroquinoxalin-2-one 104. 6-fluoro-5-({[(1R,2S,4R)-2-hydroxy-4-[({3-oxo-2H,3H,4H-pyrazino[2,3-b][1,4]thiazin-6-yl}methyl)amino]cyclohexyl]amino}methyl)-3-methoxy-1λ⁵,4-quinoxalin-1-one 105. 6-({[(1S,3R,4S)-4-[({8-chloro-2-methyl-[1,3]oxazolo[4,5-f]quinolin-9-yl}methyl)amino]-3-hydroxycyclohexyl]amino}methyl)-2H,3H,4H-pyrazino[2,3-b][1,4]thiazin-3-one 106. 6-({[(1S,3R,4S)-3-hydroxy-4-[({2-methyl-[1,3]oxazolo[4,5-f]quinolin-9-yl}methyl)amino]cyclohexyl]amino}methyl)-2H,3H,4H-pyrazino[2,3-b][1,4]thiazin-3-one 107. 6-({[(1R,4R)-4-[({2-methyl-[1,3]oxazolo[4,5-f]quinolin-9-yl}methyl)amino]cyclohexyl]amino}methyl)-2H,3H,4H-pyrazino[2,3-b][1,4]thiazin-3-one 108. 6-({[(1R,3S,4R)-3-amino-4-[(6-fluoro-3-methoxyquinoxalin-5-yl)methoxy]cyclohexyl]amino}methyl)-2H,3H,4H-pyrazino[2,3-b][1,4]thiazin-3-one 109. 6-[({[(1R,3S,4R)-3-{[(3-fluoro-6-methoxy-1,5-naphthyridin-4-yl)methyl]amino}-4-hydroxycyclopentyl]methyl}amino)methyl-2H,3H,4H-pyrazino[2,3-b][1,4]thiazin-3-one 110. 6-({[(1R,4R)-4-[({7-chloro-2-methoxypyrido[2,3-b]pyrazin-8-yl}methyl)amino]cyclohexyl]amino}methyl)-2H,3H,4H-pyrazino[2,3-b][1,4]thiazin-3-one 111. 6-({[(1R,2S,4R)-4-{[(3-fluoro-6-methoxy-1,5-naphthyridin-4-yl)methyl]amino}-2-hydroxycyclohexyl]amino}methyl)-2H,3H,4H-pyrazino[2,3-b][1,4]thiazin-3-one 112. 6-({[(1S,3R,4S)-3-amino-4-[(6-fluoro-3-methoxyquinoxalin-5-yl)methoxy]cyclohexyl]amino}methyl)-2H,3H,4H-pyrazino[2,3-b][1,4]thiazin-3-one 113. 7-chloro-8-({[(1R,2S,4R)-2-hydroxy-4-[({3-oxo-2H,3H,4H-pyrazino[2,3-b][1,4]thiazin-6-yl}methyl)amino]cyclohexyl]amino}methyl)-1-methyl-1,2-dihydroquinoxalin-2-one 114. 7-fluoro-1-methyl-8-({[(1R,4R)-4-[({3-oxo-2H,3H,4H-pyrazino[2,3-b][1,4]thiazin-6-yl}methyl)amino]cyclohexyl]oxy}methyl)-1,2-dihydroquinoxalin-2-one, 115. 7-fluoro-1-{[(1R,4R)-4-[({3-oxo-2H,3H,4H-pyrazino[2,3-b][1,4]thiazin-6-yl}methyl)amino]cyclohexyl]methoxy}-1,2-dihydroquinolin-2-one, or 116. 3-methoxy-N-[(1R,4R)-4-[({3-oxo-2H,3H,4H-pyrazino[2,3-b][1,4]thiazin-6-yl}methyl)amino]cyclohexyl]quinoxaline-5-carboxamide 117. 6-({[(1R,3S,4R)-4-{[(7-fluoro-2-methoxyquinolin-8-yl)methyl]amino}-3-hydroxycyclohexyl]amino}methyl)-2H,3H,4H-pyrazino[2,3-b][1,4]oxazin-3-one 118. 6-({[(1R,3S,4R)-4-{[(7-chloro-2-methoxyquinolin-8-yl)methyl]amino}-3-hydroxycyclohexyl]amino}methyl)-2H,3H,4H-pyrazino[2,3-b][1,4]oxazin-3-one 119. 6-({[(1R,3S,4R)-4-{[(7-fluoro-2-methoxyquinolin-8-yl)methyl]amino}-3-hydroxycyclohexyl]amino}methyl)-2H,3H,4H-pyrazino[2,3-b][1,4]oxazin-3-one 120. 6-({[(1S,3R,4S)-4-{[(7-chloro-2-methoxyquinolin-8-yl)methyl]amino}-3-hydroxycyclohexyl]amino}methyl)-2H,3H,4H-pyrazino[2,3-b][1,4]oxazin-3-one 121. 6-[({[(1R,2S,3R)-3-{[(7-fluoro-2-methoxyquinolin-8-yl)methyl]amino}-2-hydroxycyclopentyl]methyl}amino)methyl]-2H,3H,4H-pyrazino[2,3-b][1,4]oxazin-3-one 122. 6-({[(1S,4R)-4-{2-[6-(2-aminoethoxy)-3-fluoro-1,5-naphthyridin-4-yl]ethyl}cyclohexyl]amino}methyl)-2H,3H,4H-pyrazino[2,3-b][1,4]oxazin-3-one 123. 6-({[(1S,3R,4S)-4-{[(6-chloro-3-methoxyquinoxalin-5-yl)methyl]amino}-3-hydroxycyclohexyl]amino}methyl)-2H,3H,4H-pyrazino[2,3-b][1,4]oxazin-3-one 124. 6-({[(1R,3S,4R)-4-{[(6-chloro-3-methoxyquinoxalin-5-yl)methyl]amino}-3-hydroxycyclohexyl]amino}methyl)-2H,3H,4H-pyrazino[2,3-b][1,4]oxazin-3-one 125. 6-({[(1S,3R,4S)-4-{[(7-fluoro-2-methoxyquinolin-8-yl)methyl]amino}-3-hydroxycyclohexyl]amino}methyl)-2H,3H,4H-pyrazino[2,3-b][1,4]oxazin-3-one
126. 6-[({[(1R,2S,3R)-3-{[(7-fluoro-2-methoxyquinolin-8-yl)methyl]amino}-2-hydroxycyclopentyl]methyl}amino)methyl]-2H,3H,4H-pyrazino[2,3-b][1,4]oxazin-3-one
127. 6-({[(1S,3R,4S)-4-{[(6-fluoro-3-methoxyquinoxalin-5-yl)methyl]amino}-3-hydroxycyclohexyl]amino}methyl)-2H,3H,4H-pyrazino[2,3-b][1,4]oxazin-3-one
128. 6-({[(1R,3S,4R)-4-{[(7-chloro-5-fluoro-2-methoxyquinolin-8-yl)methyl]amino}-3-hydroxycyclohexyl]amino}methyl)-2H,3H,4H-pyrazino[2,3-b][1,4]oxazin-3-one
129. 6-({[(1S,3R,4S)-4-{[(7-chloro-5-fluoro-2-methoxyquinolin-8-yl)methyl]amino}-3-hydroxycyclohexyl]amino}methyl)-2H,3H,4H-pyrazino[2,3-b][1,4]oxazin-3-one
130. 6-[({[(1R,2S,3R)-3-{[(3-fluoro-6-methoxy-1,5-naphthyridin-4-yl)methyl]amino}-2-hydroxycyclopentyl]methyl}amino)methyl]-2H,3H,4H-pyrazino[2,3-b][1,4]oxazin-3-one
131. 6-({[(1R,4R)-4-{[(8-azido-6-fluoro-3-methoxy quinoxalin-5-yl)methyl]amino}cyclohexyl]amino}methyl)-2H,3H,4H-pyrazino[2,3-b][1,4]oxazin-3-one
132. 6-({[(1R,3S,4R)-4-{[(5,7-difluoro-2-methoxyquinolin-8-yl)methyl]amino}-3-hydroxycyclohexyl]amino}methyl)-2H,3H,4H-pyrazino[2,3-b][1,4]oxazin-3-one
133. 6-methoxy-4-{2-[(3 S)-3-{[({3-oxo-2H,3H,4H-pyrazino[2,3-b][1,4]oxazin-6-yl}methyl)amino]methyl}pyrrolidin-1-yl]ethyl}-3H,4H-pyrido[2,3-b]pyrazin-3-one
134. 6-({[(1R,4R)-4-{[(7-fluoro-2-methoxyquinolin-8-yl)methyl]amino}cyclohexyl]amino}methyl)-2H,3H,4H-pyrazino[2,3-b][1,4]oxazin-3-one
135. 3-methoxy-5-{2-[(3 S)-3-{[({3-oxo-2H,3H,4H-pyrazino[2,3-b][1,4]oxazin-6-yl}methyl)amino]methyl}pyrrolidin-1-yl]ethyl}-5H,6H-pyrido[2,3-b]pyrazin-6-one
136. 6-methoxy-4-(2-{4-[({3-oxo-2H,3H,4H-pyrazino[2,3-b][1,4]oxazin-6-yl}methyl)amino]piperidin-1-yl}ethyl)-3H,4H-pyrido[2,3-b]pyrazin-3-one
137. 6-({[(1R,4R)-4-{[(3-fluoro-6-methoxy-1,5-naphthyridin-4-yl)methyl]amino}cyclohexyl]amino}methyl)-2H,3H,4H-pyrazino[2,3-b][1,4]oxazin-3-one
138. (3R)-5-fluoro-3-{[(3S)-3-{[({3-oxo-2H,3H,4H-pyrazino[2,3-b][1,4]oxazin-6-yl}methyl)amino]methyl}pyrrolidin-1-yl]methyl}-1,9-diazatricyclo[6.3.1.0$^{4,12}$]dodeca-4,6,8(12),9-tetraen-11-one
139. 6-({[(1R,4R)-4-{[(6,8-difluoro-3-methoxyquinoxalin-5-yl)methyl]amino}cyclohexyl]amino}methyl)-2H,3H,4H-pyrazino[2,3-b][1,4]oxazin-3-one
140. 6-[({[(3S,4S)-1-[2-(3-fluoro-6-methoxy-1,5-naphthyridin-4-yl)ethyl]-4-hydroxypyrrolidin-3-yl]methyl}amino)methyl]-2H,3H,4H-pyrazino[2,3-b][1,4]oxazin-3-one
141. 6-({[(1R,4R)-4-{[(5-fluoro-2-methoxyquinolin-8-yl)methyl]amino}cyclohexyl]amino}methyl)-2H,3H,4H-pyrazino[2,3-b][1,4]oxazin-3-one
142. 6-({[(1R,4R)-4-{[(5,7-difluoro-2-methoxyquinolin-8-yl)methyl]amino}cyclohexyl]amino}methyl)-2H,3H,4H-pyrazino[2,3-b][1,4]oxazin-3-one
143. 6-[({[(3 S)-1-[2-(6-fluoro-3-methoxyquinoxalin-5-yl)ethyl]pyrrolidin-3-yl]methyl}amino)methyl]-2H,3H,4H-pyrazino[2,3-b][1,4]oxazin-3-one
144. 6-[({[(3S,4S)-1-[2-(3-fluoro-6-methoxy-1,5-naphthyridin-4-yl)ethyl]-4-hydroxypyrrolidin-3-yl]methyl}amino)methyl]-7-methyl-2H,3H,4H-pyrazino[2,3-b][1,4]oxazin-3-one
145. 6-[({[(1R,3 S)-3-{[(6-fluoro-3-methoxyquinoxalin-5-yl)methyl]amino}cyclopentyl]methyl}amino)methyl]-2H,3H,4H-pyrazino[2,3-b][1,4]oxazin-3-one
146. 7-methyl-6-({[(1R,4R)-4-{[(7-fluoro-2-methoxyquinolin-8-yl)methyl]amino}cyclohexyl]amino}methyl)-2H,3H,4H-pyrazino[2,3-b][1,4]oxazin-3-one
147. 6-({[(1R,4R)-4-{[(6-chloro-3-methoxyquinoxalin-5-yl)methyl]amino}cyclohexyl]amino}methyl)-2H,3H,4H-pyrazino[2,3-b][1,4]oxazin-3-one
148. 6-[({[(1R,3 S)-3-{[(3-fluoro-6-methoxy-1,5-naphthyridin-4-yl)methyl]amino}cyclopentyl]methyl}amino)methyl]-2H,3H,4H-pyrazino[2,3-b][1,4]oxazin-3-one
149. 6-({[(1R,3S,4R)-4-{[(3-chloro-6-methoxy-1,5-naphthyridin-4-yl)methyl]amino}-3-hydroxycyclohexyl]amino}methyl)-2H,3H,4H-pyrazino[2,3-b][1,4]oxazin-3-one
150. 6-[({[(1R,2S,3R)-3-{[(3-fluoro-6-methoxy-1,5-naphthyridin-4-yl)methyl]amino}-2-hydroxycyclopentyl]methyl}amino)methyl]-2H,3H,4H-pyrazino[2,3-b][1,4]oxazin-3-one
151. 6-({[(1R,4R)-4-[1-amino-2-(7-fluoro-2-methoxyquinolin-8-yl)ethyl]cyclohexyl]amino}methyl)-2H,3H,4H-pyrazino[2,3-b][1,4]oxazin-3-one
152. 6-({[(1R,4R)-4-{[(3-chloro-6-methoxy-1,5-naphthyridin-4-yl)methyl]amino}cyclohexyl]amino}methyl)-2H,3H,4H-pyrazino[2,3-b][1,4]oxazin-3-one
153. 6-[({[(3 S)-1-(2-{8-chloro-2-methyl-[1,3]oxazolo[4,5-f]quinolin-9-yl}ethyl)pyrrolidin-3-yl]methyl}amino)methyl]-2H,3H,4H-pyrazino[2,3-b][1,4]oxazin-3-one
154. 6-[({[(3S,4S)-1-(2-{8-chloro-2-methyl-[1,3]oxazolo[4,5-f]quinolin-9-yl}ethyl)-4-hydroxypyrrolidin-3-yl]methyl}amino)methyl]-2H,3H,4H-pyrazino[2,3-b][1,4]oxazin-3-one
155. 6-({[(1R,2S,4R)-4-{[(7-chloro-5-fluoro-2-methoxyquinolin-8-yl)methyl]amino}-2-hydroxycyclohexyl]amino}methyl)-2H,3H,4H-pyrazino[2,3-b][1,4]oxazin-3-one
156. 6-({[(1S,3R,4S)-4-{[(5,7-difluoro-2-methoxyquinolin-8-yl)methyl]amino}-3-hydroxycyclohexyl]amino}methyl)-2H,3H,4H-pyrazino[2,3-b][1,4]oxazin-3-one
157. 6-(difluoromethoxy)-4-{2-[(3S)-3-{[({3-oxo-2H,3H,4H-pyrazino[2,3-b][1,4]oxazin-6-yl}methyl)amino]methyl}pyrrolidin-1-yl]ethyl}-3H,4H-pyrido[2,3-b]pyrazin-3-one
158. 6-({[(1R,4R)-4-({[3-(difluoromethoxy)-6-fluoroquinoxalin-5-yl]methyl}amino)cyclohexyl]amino}methyl)-2H,3H,4H-pyrazino[2,3-b][1,4]oxazin-3-one
159. 6-({[(1R,4R)-4-({2-methoxy-8H,9H,1 OH-pyrano[3,2-f]quinolin-10-yl}amino)cyclohexyl]amino}methyl)-2H,3H,4H-pyrazino[2,3-b][1,4]oxazin-3-one
160. 6-[({2-[5-(6-fluoro-3-methoxyquinoxalin-5-yl)pyrimidin-2-yl]ethyl}amino)methyl]-2H,3H,4H-pyrazino[2,3-b][1,4]oxazin-3-one
161. 6-[({[(3 S)-1-(2-{6-methoxy-3-oxo-3H,4H-pyrido[2,3-b]pyrazin-4-yl}ethyl)pyrrolidin-3-yl]methyl}amino)methyl]-7-methyl-2H,3H,4H-pyrazino[2,3-b][1,4]oxazin-3-one
162. (2S)-5-fluoro-2-({4-[({3-oxo-2H,3H,4H-pyrazino[2,3-b][1,4]oxazin-6-yl}methyl)amino]piperidin-1-yl}methyl)-1,9-diazatricyclo[6.3.1.0$^{4,12}$]dodeca-4,6,8(12),9-tetraen-11-one 163. 7-methyl-6-({[(1R,4R)-4-{[(6-fluoro-3-methoxyqui-noxalin-5-yl)methyl]amino}cyclohexyl]amino}methyl)-2H,3H,4H-pyrazino[2,3-b][1,4]oxazin-3-one
164. (3R)-5-fluoro-3-({4-[({3-oxo-2H,3H,4H-pyrazino[2,3-b][1,4]oxazin-6-yl}methyl)amino]piperidin-1-yl}methyl)-1,9-diazatricyclo[6.3.1.0⁴,¹²]dodeca-4,6,8(12),9-tetraen-11-one
165. 7-fluoro-1-(2-{4-[({3-oxo-2H,3H,4H-pyrazino[2,3-b][1,4]oxazin-6-yl}methyl)amino]piperidin-1-yl}ethyl)-1,2-dihydroquinoxalin-2-one
166. 6-fluoro-3-methoxy-5-{2-[(3S)-3-{[({3-oxo-2H,3H,4H-pyrazino[2,3-b][1,4]oxazin-6-yl}methyl)amino]methyl}pyrrolidin-1-yl]ethyl}-1,4-quinoxalin-1-one
167. 7-methyl-6-({[(1R,4R)-4-{[(3-fluoro-6-methoxy-1,5-naphthyridin-4-yl)methyl]amino}cyclohexyl]amino}methyl)-2H,3H,4H-pyrazino[2,3-b][1,4]oxazin-3-one
168. 7-fluoro-1-{2-[(3S)-3-{[({3-oxo-2H,3H,4H-pyrazino[2,3-b][1,4]oxazin-6-yl}methyl)amino]methyl}pyrrolidin-1-yl]ethyl}-1,2-dihydroquinolin-2-one
169. 6-[({[(3S)-1-(2-{9-fluoro-2H,3H-[1,4]dioxino[2,3-f]quinolin-10-yl}ethyl)pyrrolidin-3-yl]methyl}amino)methyl]-2H,3H,4H-pyrazino[2,3-b][1,4]oxazin-3-one
170. 6-chloro-3-methoxy-5-({[(1R,4R)-4-[({3-oxo-2H,3H,4H-pyrazino[2,3-b][1,4]oxazin-6-yl}methyl)amino]cyclohexyl]amino}methyl)-1²⁵,4-quinoxalin-1-one
171. 7-methyl-6-({[(1R,4R)-4-{[(6-chloro-3-methoxyqui-noxalin-5-yl)methyl]amino}cyclohexyl]amino}methyl)-2H,3H,4H-pyrazino[2,3-b][1,4]oxazin-3-one
172. 6-({[(1R,3S,4R)-3-fluoro-4-{[(6-fluoro-3-methoxyqui-noxalin-5-yl)methyl]amino}cyclohexyl]amino}methyl)-2H,3H,4H-pyrazino[2,3-b][1,4]oxazin-3-one
173. 6-({[(1S,3R,4S)-4-{[(3-chloro-6-methoxy-1,5-naph-thyridin-4-yl)methyl]amino}-3-hydroxycyclohexyl]amino}methyl)-2H,3H,4H-pyrazino[2,3-b][1,4]oxazin-3-one
174. 6-({[(1S,3R,4S)-4-{[(7-fluoro-2,5-dimethoxyquinolin-8-yl)methyl]amino}-3-hydroxycyclohexyl]amino}methyl)-2H,3H,4H-pyrazino[2,3-b][1,4]oxazin-3-one
175. 6-[({[(1R,3S)-3-[({8-chloro-2-methyl-[1,3]oxazolo[4,5-f]quinolin-9-yl}methyl)amino]cyclopentyl]methyl}amino)methyl]-2H,3H,4H-pyrazino[2,3-b][1,4]oxazin-3-one
176. 6-({[(1R,3S,4R)-4-{[(6-chloro-3-methoxyquinolin-5-yl)methyl]amino}-3-hydroxycyclohexyl]amino}methyl)-2H,3H,4H-pyrazino[2,3-b][1,4]oxazin-3-one, or
177. 6-({[(1S,3R,4S)-4-{[(6-chloro-3-methoxyquinolin-5-yl)methyl]amino}-3-hydroxycyclohexyl]amino}methyl)-2H,3H,4H-pyrazino[2,3-b][1,4]oxazin-3-one as well as pharmaceutically acceptable salts, solvates and N-oxides thereof. For compounds other that those whose synthesis is provided by specific example, the above compounds may be made utilizing the teachings set forth herein.

In another aspect, the invention also provides a compound selected from the group consisting of:

6-((((1R,4R)-4-(((6-fluoro-3-methoxyquinoxalin-5-yl)methyl)amino) cyclohexyl)amino)methyl)-2H-pyrazino[2,3-b][1,4]oxazin-3 (4H)-one;

6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one; or pharmaceutically acceptable salts, solvates and N-oxides thereof.

In another aspect the invention provides a compound selected from the group consisting of:

6-((((1R,4R)-4-(((6-fluoro-3-methoxyquinoxalin-5-yl)methyl)amino) cyclohexyl)amino)methyl)-2H-pyrazino[2,3-b][1,4]oxazin-3 (4H)-one;

6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3 (4H)-one;

2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one; and pharmaceutically acceptable salts, solvates and N-oxides thereof.

The compounds of the invention may be made by various techniques. As an example, the compounds can be made according to the general schemes I, II and III. All variables defined in the schemes are those which are defined herein, unless otherwise noted.

Scheme I

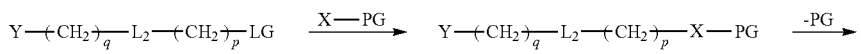
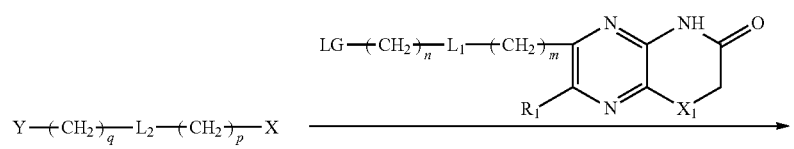
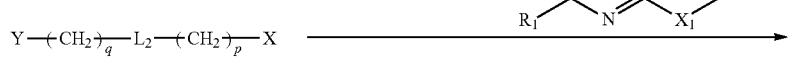
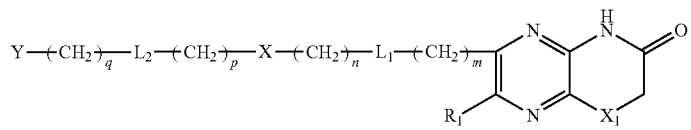

LG: leaving group
PG: protecting group

Scheme II

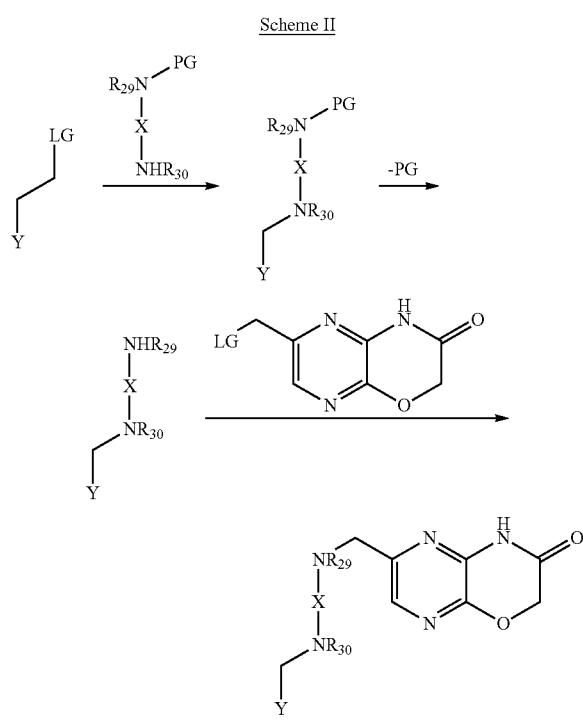

LG: leaving group
PG: protecting group

Scheme III

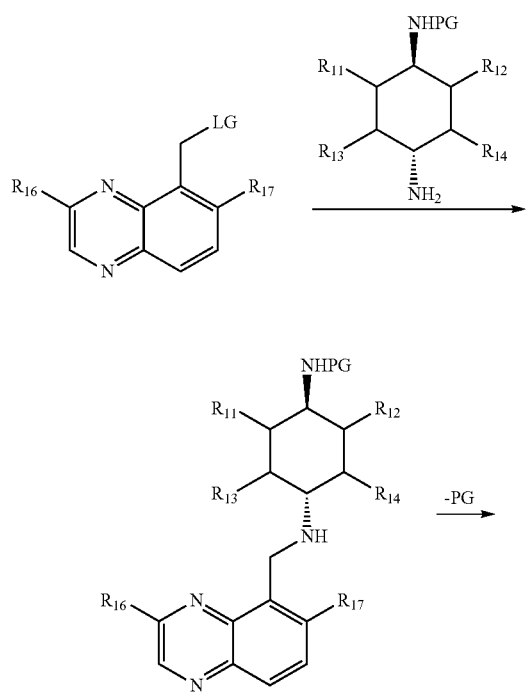

LG: leaving group  PG: protecting group

This invention also provides a method of treatment of bacterial infections in mammals, particularly in a human, which method comprises the administration to a mammal in need of such treatment an effective amount of a compound of the invention of formulae (I), (II), (III), (IV), (V), (VI) or (VII) as well as compounds numbered 1-177, or a pharmaceutically acceptable salt, solvate or N-oxide thereof.

The invention also provides the use of compounds of the invention of formulae (I), (II), (III), (IV), (V), (VI) or (VII) as well as compounds numbered 1-177, pharmaceutically acceptable salts, solvates or N-oxides thereof in the manufacture of a medicament for use in the treatment of bacterial infections in mammals, e.g., humans.

The invention also provides a compound of the present invention of formulae (I), (II), (III), (IV), (V), (VI) or (VII) as well as compounds numbered 1-177, or a pharmaceutically acceptable salt thereof, solvate or N-oxide thereof, for use in the treatment of bacterial infections in mammals, e.g., humans.

The invention also provides a pharmaceutical composition comprising compounds of the present invention, of formulae (I), (II), (III), (IV), (V), (VI) or (VII) as well as compounds numbered 1-177 or pharmaceutically acceptable salts thereof, and pharmaceutically acceptable carriers. For the purposes of the invention, the term "pharmaceutical composition" may encompass pharmaceutical formulations.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation. Crystalline forms of the compounds are encompassed by the present invention.

Furthermore, it will be understood that phrases such as "a compound of the invention or pharmaceutically acceptable salts" are intended to encompass the compounds set forth herein, a pharmaceutically acceptable salt of the compounds, a solvate of the compounds, or any pharmaceutically acceptable combination of these. Thus by way of non-limiting example used here for illustrative purpose, "a compound of or pharmaceutically acceptable salts solvates, or N-oxides thereof" may include pharmaceutically acceptable salts of these compounds that are further present as solvates or N-oxides.

Since the compounds of the invention are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of the compounds, or pharmaceutically acceptable salts, solvates or N— oxides thereof.

Pharmaceutically acceptable salts of the above-mentioned compounds of the invention include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. The invention extends to all such derivatives.

Certain of the compounds of the invention may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Certain compounds of the invention may also exist in polymorphic forms and the invention includes such polymorphic forms.

The antibacterial compounds according to the invention may be formulated for administration in any convenient way for use in human or veterinary medicine, by analogy with other antibacterials.

The pharmaceutical compositions of the invention may be formulated for administration by any route and include those in a form adapted for oral, topical or parenteral use and may be used for the treatment of bacterial infection in mammals including humans.

The compositions may be in the form of tablets, capsules, powders, granules, lozenges, suppositories, creams or liquid preparations, such as oral or sterile parenteral solutions, powders or suspensions, as well as being present as inhalation compositions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

In one embodiment, the compounds of the invention of formulae (I), (II), (III), (IV), (V), (VI) or (VII), and compounds numbered 1-177 along with pharmaceutically acceptable salts, solvates and N-oxides thereof can be used in a liposomal pharmaceutical formulation. In another aspect, the invention includes a liposome comprising a lipid bilayer membrane encapsulating an aqueous interior region therein. The aqueous region comprises one of the compounds of the present invention such that the compound(s) is/are entrapped within the interior region, or in certain embodiments the compounds may be present in the lipid itself. As an example, in one embodiment, the compound of formula (VII), pharmaceutically acceptable salts (including those exemplified herein), solvates and N-oxides thereof, may reside in the aqueous interior region. As another example, in another embodiment, the compounds of formulae (IV) and (V), pharmaceutically acceptable salts (including those exemplified herein), solvates and N-oxides thereof, may reside in the aqueous interior region or in the lipid itself.

Liposomes of the present invention incorporate a surface active agent into a bilayer composed primarily of a relatively water-insoluble molecule, such as a dichain phospholipid, according to techniques know to one of ordinary skill in the art. Preferred phospholipids include, without limitation, dipalmitoylphosphatidylcholine (DPPC), 1,2-Distearoyl-sn-glycero-3-phosphocholine (DSPC), hydrogenated soy phosphatidyl choline (HSPC), egg sphingomyelin (ESM), as well as others. Examples of surface active agents that can be used in the liposomes of the present invention include, without limitation, palmitoyl alcohols, stearoyl alcohols, myristoyl surfactants, stearoyl surfactants, palmitoyl surfactants polyethylene glycol, glyceryl monopalmitate, glyceryl monooleate, ceramides, and PEG-ceramides. A particularly preferred surface active agent includes, as an example, cholesterol. Other lysolipids can also be used and include, but are not limited to, monoacylphosphatydlcholines where the head group can be phosphatdyl glycerols, inositols, ethanolamines, or ceramides, and the single acyl chain can be for example $C_8$-$C_{22}$, with one or more C=C double bonds in the chain. Exemplary lysolipids include, but are not limited to, monopalmitoylphosphatidylcholine (MPPC). monolaurylphosphatidylcholine (MLPC), monomyristoyl-phosphatidylcholine (MMPC), monostearoylphosphatidylcholine (MSPC), and mixtures thereof.

Other suitable surface active agents may include, for example, a dichain phospholipid having chains preferably of no greater than $C_{10}$, glycolipids, and bile salts that are quite surface active but will enter a bilayer without dissolving it at concentrations less than their CMC, which can be as high as tens of milliMolar. Suitable surface-active agents are those that are compatible with the primary lipid of the bilayer, and that desorb when the lipid melts to the liquid phase. It should also be appreciated that other surface-active agents that are not completely compatible with the primary lipid may also be employed. Additional suitable surface-active agents for use in phospholipid bilayers include, but are not limited to, palmitoyl alcohols, stearoyl alcohols, myristoyl surfactants, stearoyl surfactants, palmitoyl surfactants polyethylene glycol, glyceryl monopalmitate, glyceryl monooleate, ceramides, PEG-ceramides, and therapeutic lipids. As a example of liposomal formulations, such may include two or more phospholipids and a surface active agent, along with a compound of the invention, for example 6-((((1r,4r)-4-(((6-fluoro-3-methoxyquinoxalin-5-yl) methyl)amino) cyclohexyl)amino)methyl)-2H-pyrazino[2,3-b][1,4]oxazin-3(4H)-one, along with pharmaceutically acceptable salts, solvates, and N— oxides thereof, most preferably the hydrochloride salt of this compound.

Examples of exemplary liposomal compositions of the invention include the following, preferably encompassing 6-((((1R,4R)-4-(((6-fluoro-3-methoxyquinoxalin-5-yl) methyl)amino) cyclohexyl)amino)methyl)-2H-pyrazino[2,3-b][1,4]oxazin-3(4H)-one or a pharmaceutically acceptable salt, solvate, or N-oxide thereof, more preferably the hydrochloride salt thereof although all other compounds of the invention may be incorporated therein:

HSPC:cholesterol:DSPG. present in amounts (mole percent): 64:33:3

DSPC:cholesterol:DSPG: present in amounts (mole percent): 55:25:20 (API concentration approx 10 mg/ml; total lipid concentration approx. 40 mg/ml, size approx 100 nm)

The above specified formulations are based on the total liposomal contents (without active compound)

The above formulations may include the compounds of formulae IV or V (e.g., hydrochloric acid form) in an amount ranging from 20-25 mole percent based on the total composition (liposomal materials and active compound).

In addition to those compounds of the present invention, liposomal compositions that include 6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one, along with pharmaceutically acceptable salts, solvates, and N-oxides thereof are encompassed, and in particular the hydrochloride salt of this particular compound.

In general, liposomes according to the present invention may be prepared by techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993 as well as U.S. Pat. No. 5,882,679. In one embodiment, a composition may include a liposome with an interior aqueous space. The liposome having a gel-phase lipid bilayer membrane comprising phospholipid and lysolipid, wherein phospholipid and lysolipid are contained in the bilayer membrane.

In one embodiment, compositions may be present as inhaled compositions. As an example, in one embodiment, such may be present in the form of dry powder compositions administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in DISKUS™, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in TURBUHALER™, see EP 69715, or in the devices described in U.S. Pat. No. 6,321,747). An example of a unit-dose device is ROTAHALER™ (see GB 2064336). In one embodiment, the DISKUS™ inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additives taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in another embodiment, the ELLIPTA™ inhalation device, which permits separate containment of two different components of the composition. Thus, for example, these components are administrable simultaneously but are stored separately, e.g. in separate pharmaceutical compositions, for example as described in WO 03/061743 A1 WO 2007/012871 A1 and/or WO2007/068896. In one embodiment, the ELLIPTA™ inhalation device has two peelable blister strips, each strip containing pre-metered doses in blister pockets arranged along its length, e.g., multiple containers within each blister strip. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUO-HALER™ of Innovata. In addition, various structures of inhalation devices provide for the sequential or separate delivery of the pharmaceutical composition(s) from the device, in addition to simultaneous delivery.

Such dry powder inhaled compositions may include a compound of the present invention as well as other inert agents. Inert ingredients are broadly defined to include excipients, carriers, additives that improve stability performance, and the like. Examples of excipients include monosaccharides, such as mannitol, arabinose, xylitol and dextrose and monohydrates thereof, disaccharides, such as lactose, maltose and sucrose, and polysaccharides such as starches, dextrins or dextrans. More preferred excipients comprise particulate crystalline sugars such as glucose, fructose, mannitol, sucrose and lactose. Especially preferred excipients are anhydrous lactose and lactose monohydrate. Stability performance additives include, without limitation, e.g., magnesium stearate or calcium stearate.

Particles that may be used in dry powder inhalation compositions also include particles fabricated through the PRINT® Technology (Liquidia Technologies, Inc.). In particular the particles are made by molding the materials intended to make up the particles in mold cavities. The molds can be polymer-based molds and the mold cavities can be formed into a desired shape and dimensions. Uniquely, as the particles are formed in the cavities of the mold, the particles are highly uniform with respect to shape, size and composition. The methods and materials for fabricating the particles of the present invention are further described and disclosed in the applicant's issued patents and co-pending patent applications, each of which are incorporated herein by reference in their entirety: U.S. Pat. Nos. 8,465,775; 8,263,129; 8,158,728; 8,128,393; 8,465,775; 7,976,759; 8,444,907; and U.S. Pat. Application Publications Nos. 2013-0249138; US 2012-0114554; and US 2009-0250588.

The composite particles are generally non-spherical, having an engineered shape corresponding to a mold in which the particles are formed. The composite particles are therefore substantially uniform in shape, substantially equal size, or substantially uniform in shape and substantially equal size. The uniformity is advantageously monodisperse in comparison with other milled, or spray dried materials which will possess a variety of aerodynamically sized particles. A further attribute of the composite particles is that in their physical structure, they may be generally homogeneously solid throughout. Thus, they lack hollow cavities or large porous structures which may be created in droplet creation and liquid phase evaporative processes, for example spray drying. This homogeneity allows for densification of the materials within the particles, which may provide such benefits such as compositional rigor, increased drug loading per composite particle, and the like.

In one or more embodiments of this aspect of the invention, the composite particles may be substantially non-porous. Molding potentially allows the composite particles to be formed in a wide variety of shapes, including but not limited to: those having two substantially parallel surfaces; two substantially parallel surfaces with each substantially parallel surface having substantially equal linear dimensions; two substantially parallel surfaces and one or more substantially non-parallel surfaces. Other shapes include those with one or more angle, edge, arc, vertex, and/or point, and any combination thereof, including, but not limited to, such shapes as a trapezoid, cone, rectangle, and/or arrow, and the like. Other shapes when viewed in 2-dimensions, particular orientation, may include triangles, quadrilaterals, polygons, circles, and the like. In 3-dimensions, the shapes may include cones, polygons, pyramids, and cylinders, whether right, truncated, frustum, or oblique.

The compounds of the invention may also be administered via inhaled aerosol formulations. Aerosols may be formed by suspending or dissolving a compound of invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art. The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of the present invention or pharmaceutically acceptable salts thereof and a fluorocarbon or hydrogen-containing chlorofluorocarbon as propellant, optionally in combination with a surfactant and/or a cosolvent. According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof. Formulations suitable for nebulized delivery are also encompassed by the invention, including the compounds of the invention. In one preferred embodiment, the invention includes an inhaled formulation comprising a compound of formula (VI), pharmaceutically acceptable salts, solvates, and N-oxides thereof (e.g., a hydrochloride salt), as a dry powder formulation, an aerosol formulation or a nebulized formulation.

With respect to dose for any suitable formulation set forth herein above, the compositions may contain from 0.1% by weight, preferably from 10-60% by weight, of a compound, depending on the method of administration. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Such a dosage corresponds to about 1.5 to about 50 mg/kg per day. Suitably the dosage is from 5 to 30 mg/kg per day.

The compound of the invention may be the sole therapeutic agent in the compositions of the invention or a combination with other antibacterials. If the other antibacterial is a ß-lactam then a ß-lactamase inhibitor may also be employed. Compounds of the invention may be used in the treatment of bacterial infections caused by a wide range of Gram-negative (e.g., *Haemophilus influenza, Moraxella catarrhalis, Acinetobacter baumannii, Escherichia coli, Pseudomonas aeruginosa, Proteus mirabilis, Legionella pneumophila, Enterobacter cloacae, Enterobacter aerogenes, Klebsiella pneumonia, stenotrophomonas maltophilla, citrobacter* spp, *Burkholderia cepacia, Serratia marcescens*, and *Providencia rettgeri*) and Gram-positive organisms (e.g., *Staphylococcus aureus, Streptococcus pneumoniae, Streptococcus pyogenes, Enterococcus faecalis, Streptococcus agalactiae, viridans* group *Streptococcus, Enterococcus faecium* and methicillin resistant *Staphylococcus aureus* (MRSA)) including bioterrorism organisms and anaerobic bacteria (e.g., *Bacteroides fragilis, Bacteroides caccae, Bacteroides ovatus* and *Bacteroides thetaiotamicron*), upper and/or lower respiratory tract infections, skin and soft tissue infections and/or urinary tract infections. Compounds of the invention may be also used in the treatment of tuberculosis caused by *Mycobacterium tuberculosis*. The antibacterial activity of compounds of the invention may be determined by the methods described herein.

In various embodiments, the compounds of the invention, pharmaceutically acceptable salts and N-oxides thereof may also be used to treat bacterial infections associated with one or more biothreat or bioterrorism organisms such as, without limitation, *Yersinia pestis, Bacillus anthracis, Francisella tularensis, Burkholderia mallei, Burkholderia pseudomallei, Brucella suis, Brucella Melitensis*, or *Brucella abortus*. Accordingly, the invention provides a method of treating a bacterial infection associated with one or more organisms selected from the group consisting of *Yersinia pestis, Bacillus anthracis, Francisella tularensis, Burkholderia mallei, Burkholderia pseudomallei, Brucella suis, Brucella Melitensis*, and *Brucella abortus*, the method comprising administering to a subject a compound of the present invention of formulae (I), (II), (III), (IV), (V), (VI) or (VII) including compounds numbered 1 to 177, a pharmaceutically acceptable salt or an N-oxide thereof. The invention also provides a method of treating a bacterial infection associated with one or more organisms selected from the group consisting of *Yersinia pestis, Bacillus anthracis, Francisella tularensis, Burkholderia mallei, Burkholderia pseudomallei, Brucella suis, Brucella Melitensis*, and *Brucella abortus*, the method comprising administering to a subject a pharmaceutical formulation comprising a compound of the present invention including compounds of the present invention of formulae (I), (II), (III), (IV), (V), (VI) or (VII) including compounds numbered 1 to 177, a pharmaceutically acceptable salt or an N-oxide thereof and a pharmaceutically acceptable carrier. Preferred compounds, pharmaceutically acceptable salts or N-oxides thereof administered according to these above methods include those of formulae (IV), (V), (VI) or (VII), and exemplary compounds, pharmaceutically acceptable salts (e.g., hydrochloride salts), or N-oxides thereof are of formulae (IV) and (V). Preferred pharmaceutical formulations that may be administered according to these methods include all of those formulations set forth herein, including liposomal formulations both generally and specifically disclosed herein, and inhaled formulations.

Additionally, the compounds of the invention, including compounds of the present invention of formulae (I), (II), (III), (IV), (V), (VI) or (VII) including compounds numbered 1 to 177, particularly when administered via the inhaled route, may be used for prophylaxis, treatment (e.g., early treatment) and chronic management of bacterial infection in cystic fibrosis patients; of bacterial exacerbations in (1) chronic obstructive pulmonary disease ("COPD"); (2) non-CF ("cystic fibrosis") bronchiectasis and (3) ("hospital-acquired pneumonia"/"ventilator-associated pneumonia") HAP/VAP. For such inhaled-related indications, the invention encompasses the use of a compound in the manufacture of a medicament for use in the treatment for such indications in mammals, e.g., humans. The invention also encompasses a compound of the invention for use in the treatment of for such indications in mammals, e.g., humans. Exemplary compounds for use in these methods are those of formulae (I), (II), (III), (IV), (V), (VI) and (VII) as well as compounds numbered 1-177, including preferred salt forms set forth herein, as well as pharmaceutically acceptable salts, solvates and N-oxides thereof.

As used hereinabove, "treat" or "treatment" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder. For the purposes of the present invention,"treat" or "Treatment" of a disorder may include prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

In one embodiment, the invention includes a method of treatment of bacterial infections in mammals, particularly in man, which method comprises the administration to a mammal (e.g., human) in need of such treatment an effective amount of the compound of the invention, more preferably for example, one selected from the group:

6-((((1R,4R)-4-(((6-fluoro-3-methoxyquinoxalin-5-yl) methyl)amino) cyclohexyl)amino)methyl)-2H-pyrazino [2,3-b][1,4]oxazin-3 (4H)-one;

6-((((1R,3S,4R)-4-(((6-fluoro-3-methoxyquinoxalin-5-yl) methyl)amino)-3-hydroxycyclohexyl)amino)methyl)-2H-pyrazino[2,3-b][1,4]oxazin-3 (4H)-one;

2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one; or a pharmaceutically acceptable salt, solvate, or N-oxide thereof, including all preferred forms set forth herein.

In one embodiment, the invention includes the use of the compound of the invention, more preferably for example, one selected from the group:

6-((((1R,4R)-4-(((6-fluoro-3-methoxyquinoxalin-5-yl) methyl)amino) cyclohexyl)amino)methyl)-2H-pyrazino [2,3-b][1,4]oxazin-3 (4H)-one;

6-((((1R,3S,4R)-4-(((6-fluoro-3-methoxyquinoxalin-5-yl) methyl)amino)-3-hydroxycyclohexyl)amino)methyl)-2H-pyrazino[2,3-b][1,4]oxazin-3 (4H)-one;

2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one; or a pharmaceutically acceptable salt, solvate, or N-oxide thereof, including all preferred forms set forth herein, for use in the treatment of bacterial infections in a mammal (e.g., human), In one embodiment, the invention includes a compound of the invention, more preferably for example, one selected from the group:

6-((((1R,4R)-4-(((6-fluoro-3-methoxyquinoxalin-5-yl)methyl)amino) cyclohexyl)amino)methyl)-2H-pyrazino[2,3-b][1,4]oxazin-3 (4H)-one;

6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one;

2-({[((3S)-1-{2-[6-(methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one;

or a pharmaceutically acceptable salt, solvate, or N-oxide thereof, including all preferred forms set forth herein, for use in the treatment of bacterial infections in a mammal (e.g., human).

The invention also encompasses a compound which is:

The following examples illustrate the preparation of certain compounds of the invention and intermediates for making the same.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Examples and Experimental

General

Abbreviations in the examples:
MS=mass spectrum
ES=Electrospray mass spectroscopy
LCMS=Liquid chromatography mass spectroscopy
HPLC=high performance liquid chromatography
rt=room temperature
TFA=trifluoroacetic acid
THF=tetrahydrofuran
Pd/C=palladium on carbon
DCM=dichloromethane
MeOH=methanol
EtOH=ethanol
i-PrOH=isopropanol Et₂O or ether=diethyl ether
DMF=N,N-dimethylformamide
EA or EtOAc=ethyl acetate
NaBH(OAc)₃=sodium triacetoxyborohydride
Pd₂(dba)₃=tris(dibenzylideneacetone)dipalladium (0)
XPhos=dicyclohexyl[2',4',6'-tris(1-methylethyl)-2-biphenylyl]phosphane
LAH=lithium aluminium hydride
DIBAL-H=di-isobutylaluminium hydride
K₂CO₃=potassium carbonate
NaIO₄=sodium periodate
OsO₄=osmium tetroxide
ppm=parts per million
¹H NMR=proton nuclear magnetic resonance
TMS=tetramethylsilane
CDCl₃=deuteriochloroform
MeOH-d₄=tetradeuteriomethanol
DMSO-d₆=hexadeuteriodimethylsulfoxide
MLV—Multi-lamellar vesicles
LUV—Large unilamellar vesicles
CF—Clarifying Filtration
SF—Sterile Filtration
DSPC—1,2-distearoyl-sn-glycero-3-phosphocholine
DSPG—1,2-distearoyl-sn-glycero-3-phospho-(1'-rac-glycerol)
CHOL—Cholesterol
API—Active Pharmaceutical Ingredient
DF—Diafiltration
UF—Ultrafiltration
SEC—Size Exclusion Chromatography
UPLC—Ultra Performance Liquid Chromatography
MWCO—Molecular Weight Cut Off
DLS—Dynamic Light Scattering
PC filters—Polycarbonate filters
mPES—modified Polyethersulfone
HFC—Hollow Fiber Cartridge ¹H NMR spectra were recorded at 400 or 250 MHz, and chemical shifts are reported in ppm downfield from the internal standard TMS. Abbreviations for NMR data are as follows: s=singlet, d=doublet, t=triplet, q=quartet, m=multiplet, dd=doublet of doublets, dt=doublet of triplets, td=triplet of doublets, app=apparent, br=broad. J indicates the NMR coupling constant measured in Hertz. Mass spectra were obtained using ES ionization techniques. All temperatures are reported in degrees Celsius. Celite® is a filter aid composed of acid-washed diatomaceous silica, and is a trademark of Manville Corp., Denver, Colo.

As will be understood by the skilled chemist, references to preparations carried out in a similar manner to, or by the general method of, other preparations, may encompass variations in routine parameters such as time, temperature, workup conditions, minor changes in reagent amounts, etc. Reactions involving palladium catalysts and metal hydrides including sodium triacetoxyborohydride were carried out under nitrogen or other inert gas.

Preparation A: 3-Oxo-3,4-dihydro-2H-pyrazino[2,3-b][1,4]thiazine-6-carbaldehyde

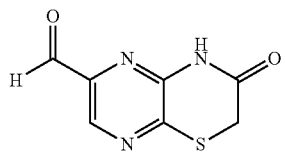

(a) 3-Bromo-6-chloro-2-pyrazinamine

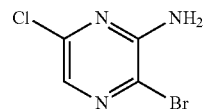

A mixture of 6-chloropyrazin-2-amine (120 g, 0.93 mmol) in CHCl₃ (1 L) was stirred at r.t. for 0.5 h. Then NBS (247 g, 1.39 mmol) was added in portions. The reaction mixture was stirred at rt for 2 h and heated to reflux for 3 h. The reaction mixture was cooled to rt and treated with water (1 L). The mixture was extracted with CH₂C₁₂ (5×300 mL). The combined organic layers were washed with brine (200 mL), dried over Na₂SO₄ and evaporated in vacuo. The resulting residue was purified by column chromatography on silica gel (PE:DCM=5:1) to afford the crude product, which was recrystallized in DCM:PE (1:5) to afford the product (21.7 g, 11%), as a yellowish solid.
1H NMR (400 MHz, CDCl3): δ 7.68 (s, 1H), 5.32 (s, 2H).

(b) 6-Chloro-2H-pyrazino[2,3-b][1,4]thiazin-3(4H)-one

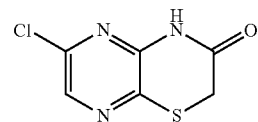 [SMILES: O=C1CSc2ncc(Cl)nc2N1]

The mixture of NaH (28.8 mg, 60%, 0.72 mmol) in DMF (5 mL) was stirred at 0° C. for 15 min, and then ethyl mercaptoacetate (86.5 mg, 0.72 mmol) was added dropwise at 0° C. The reaction mixture was stirred at 0° C. for 1 h. 3-Bromo-6-chloro-2-pyrazinamine (100 mg, 0.48 mmol) was added in portions. The reaction mixture was stirred at rt overnight. The reaction mixture was poured into ice-water (100 mL). The mixture was extracted with EtOAc (3×10 mL). The combined organic layers were dried over Na₂SO₄ and purified by pre-TLC (PE:EA 3:1) to afford the product (30 mg, 31%), as a white solid. 1H NMR (400 MHz, DMSO): δ 11.51 (s, 1H), 8.23 (s, 1H), 3.81 (s, 2H).

(c) 6-[(E)-2-phenylethenyl]-2H-pyrazino[2,3-b][1,4]thiazin-3(4H)-one

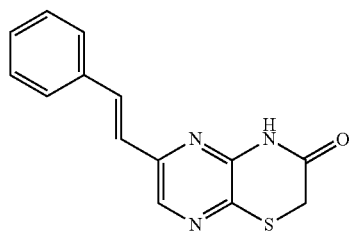 [SMILES: O=C1CSc2ncc(/C=C/c3ccccc3)nc2N1]

A mixture of 6-chloro-2H-pyrazino[2,3-b][1,4]thiazin-3 (4H)-one (500 mg, 2.48 mmol), [(E)-2-phenylethenyl]boronic acid (733 mg, 4.96 mmol), Pd(dppf)Cl₂ (181 mg, 0.25 mg) and K₂CO₃ (1.7 g, 12.40 mmol) in 1,4-dioxane (6 mL)

containing 2 mL of water was stirred at 110° C. overnight under N$_2$. 50 mL of water was added. The reaction mixture was extracted with EtOAc (5×5 mL). The combined organic layers were dried over Na$_2$SO$_4$ and purified by column chromatography on silica gel (PE:EA=20:1-7:1) to afford the product (180 mg, 27%) as a yellow solid.

$^1$H NMR (400 MHz, CDCl$_3$): δ 8.17 (s, 1H), 8.10 (s, 1H), 7.64 (d, J=16, 1H), 7.55 (d, J=18, 2H), 7.41-7.31 (m, 3H), 7.03 d, J=16, 1H), 3.71 (s, 2H).

(d) 3-Oxo-3,4-dihydro-2H-pyrazino[2,3-b][1,4]thiazine-6-carbaldehyde

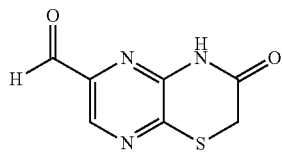

A mixture of 6-[(E)-2-phenylethenyl]-2H-pyrazino[2,3-b][1,4]thiazin-3(4H)-one (20 mg, 0.074 mmol), OsO$_4$ (1.3 mg, 0.005 mmol) and NaIO$_4$ (24 mg, 0.11 mmol) in 1,4-dioxane (2 mL) containing 0.1 mL of water was stirred at rt overnight. The solvent was removed in vacuo. The resulting residue was poured to 20 mL of EtOAc. The mixture was stirred at rt for 1 h and filtered. The filtrate was concentrated in vacuo to afford the product (7 mg, 49%), as a grey solid.

1H NMR (400 MHz, DMSO): δ 11.60 (s, 1H), 9.89 (s, 1H), 8.56 (s, 1H), 3.90 (s, 2H).

Alternative Preparation A (a) Methyl 7-bromo-3-oxo-3,4-dihydro-2H-pyrazino[2,3-b][1,4]thiazine-6-carboxylate

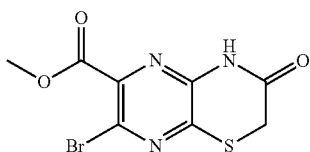 [SMILES: COC(=O)c1nc2c(nc1Br)SCC(=O)N2]

A solution of methyl 6-amino-3,5-dibromo-2-pyrazinecarboxylate (see alternative preparation B (c)) (1000 g, 3.24 mol, 1 equiv) K$_2$CO$_3$ (893 g, 6.47 mol, 2.0 equiv) in DMF (10 L) was placed in a 20 L 4-necked round-bottom flask. Ethyl 2-mercaptoacetate (349 g, 2.91 mol, 0.9 equiv) was added dropwise to above the solution while maintaining the temperature at −10-0° C. (about 1 hours added completion). The resulting solution was allowed to react for 2 h while maintaining the temperature at 70° C. The reaction progress was monitored by LCMS until the starting material was consumed completely. The reaction mixture was cooled to room temperature. The reaction was then quenched by 20 L water. The pH value of the solution was adjusted to 3-4 with 6M hydrogen chloride. The resulting solution was extracted with ethyl acetate (3×10 L) and the organic layers were combined. The organic phase was dried over anhydrous sodium sulfate. The organic phase was concentrated under vacuum. The residue product was purified by chromatogram on silica gel with DCM/EA (1:1) to give the desired product (350 g, 95% purity, 35% yield) as a light yellow solid 1H-NMR (300 MHz, DMSO-d6) δ: 12.03 (1H, s), 5.76 (2H, s), 3.86 (3H, s).

(b) Methyl 3-oxo-3,4-dihydro-2H-pyrazino[2,3-b][1,4]thiazine-6-carboxylate

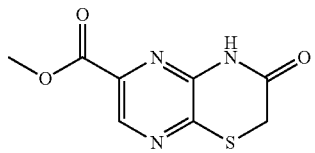

A solution of NaOAc (870 g, 10.6 mol, 2.0 equiv), Pd/C (10%, 800 g), methyl 7-bromo-3-oxo-3,4-dihydro-2H-pyrazino[2,3-b][1,4]thiazine-6-carboxylate (1.6 kg, 5.28 mol, 1 equiv) in MeOH (32 L) and THF (32 L) was placed in a 100 L pressure tank reactor (30 atm). The resulting solution was stirred for 24 h at 50° C. The reaction progress was monitored by LCMS until the starting material was consumed completely. The reaction mixture was hot to 60° C. for 1 h. A filtration was performed to remove Pd/C. The resulting mixture was washed with THF (20 L×2). The resulting mixture was concentrated (to 1 L) under vacuum. The solids were collected by filtration and added in 2 L water. The pH value of the solution was adjusted to 3-4 with 3M hydrogen chloride. The solids were collected by filtration and dried to give the product (0.95 kg, 98% purity, 80% yield) as a yellow solid.

1H-NMR (300 MHz, DMSO-d6) δ: 11.61 (1H, s), 8.64 (1H, s), 3.90 (2H, s), 3.89 (3H, s)

(c) 6-(Hydroxymethyl)-2H-pyrazino[2,3-b][1,4]thiazin-3 (4H)-one

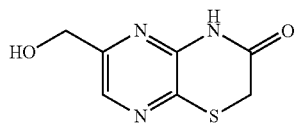 [SMILES: O=C1CSc2ncc(CO)nc2N1]

A solution of methyl 3-oxo-3,4-dihydro-2H-pyrazino[2,3-b][1,4]thiazine-6-carboxylate (400 g, 1.78 mol, 1 equiv) in THF (8 L) was placed in a 20 L 4-necked round-bottom flask under N$_2$. LiBHEt$_3$(1M) (5.7 L, 3.2 equiv) was added dropwise to above the solution while maintaining the temperature at −10-0° C. (about 1 hours added completion). The resulting solution was allowed to react for 1 h while maintaining the temperature at −10-0° C. The reaction progress was monitored by LCMS until the starting material was consumed completely. The pH value of the solution was adjusted to 3-4 with 6M hydrogen chloride (about 500 ml). The resulting solution was extracted with THF (2×5 L) and the organic layers were combined. The organic phase was dried over anhydrous sodium sulfate. The organic phase was concentrated (to 1 L) under vacuum. The solids were collected by filtration and dried to give the product (189 g, 98% purity, 54% yield) as a yellow solid.

1H-NMR (300 MHz, DMSO-d6) δ: 11.21 (1H, s), 8.17 (1H, s), 5.59 (1H, b), 4.51 (2H, s), 3.78 (2H, s)

(d) 3-Oxo-3,4-dihydro-2H-pyrazino[2,3-b][1,4]thi-azine-6-carbaldehyde

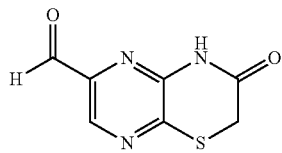 [SMILES: O=Cc1cnc2c(n1)NC(=O)CS2]

A solution of 6-(hydroxymethyl)-2H-pyrazino[2,3-b][1,4]thiazin-3(4H)-one (200 g, 1.02 mol, 1 equiv) in THF (4 L) and DCE (4 L) was placed in a 20 L 4-necked round-bottom flask. $MnO_2$ (2.2 kg, 25.4 mol, 25 equiv) was added in several portions to above the solution while maintaining the temperature at 75-80° C. The reaction progress was monitored by LCMS until the starting material was consumed completely. A filtration was performed to remove $MnO_2$. The filtrate was concentrated (to 1 L) under vacuum. The solids were collected by filtration and dried. The product (60 g g, 98% purity, 30% yield) was obtained as a yellow solid. The mother liquid was purified by chromatogram on silica gel with EA/DCM (1:1) to give the desired product (20 g) in a light yellow solid. In all, the product (79 g, 95% purity, 40% yield) was obtained as a yellow solid.

1H-NMR (300 MHz, DMSO-d6) δ: 11.65 (1H, s), 9.93 (1H, s), 8.62 (1H, s), 3.92 (2H, s).

Preparation B 3-Oxo-3,4-dihydro-2H-pyrazino[2,3-b][1,4]oxazine-6-carbaldehyde

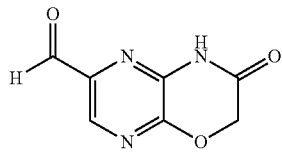 [SMILES: O=Cc1cnc2c(n1)NC(=O)CO2]

(a) 6-Chloro-3-(methyloxy)-2-pyrazinamine

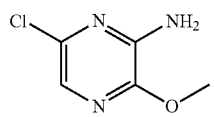

A mixture of 3-bromo-6-chloro-2-pyrazinamine (15 g, 72 mmol) in MeOH (200 mL) was stirred at rt for 10 min. Then, sodium methoxide (3.9 g, 72 mmol) was added at rt. The reaction mixture was stirred at 80dec overnight. MeONa (3.9 g, 72 mmol) was added. The mixture was stirred at 80° C. for 24 h. The reaction mixture was poured into ice-water (500 mL) and extracted with DCM (5×50 mL). The combined organic layers were dried over $Na_2SO_4$ and filtered. The solvent was removed in vacuo. The resulting residue was purified by column chromatography on silica gel (PE:DCM 5:1) to afford the product (7.5 g, 65%), as a yellow solid.

1H NMR (400 MHz, CDCl3): δ 7.37 (s, 1H), 5.00 (brs, 1H), 3.97 (s, 3H).

(b) 3-Amino-5-chloro-2(1H)-pyrazinone

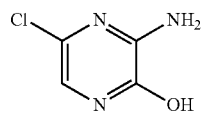

A mixture of 6-chloro-3-(methyloxy)-2-pyrazinamine (7.5 g, 47 mmol) in DCE (400 mL) was stirred at rt for 1 h. BBr3 (22 mL, 23.5 mmol) was added dropwise at rt. The reaction mixture was stirred at 60° C. overnight. The mixture was quenched with the addition of $CH_3OH$ (50 mL) at 0° C. The mixture was allowed to warmed to rt and stirred for 1 h at rt. The solid was collected by filtration and washed with DCM (5×10 mL). The solid was then dried in vacuo to afford the product (8 g).

(c) 2-Chloro-N-(6-chloro-3-oxo-3,4-dihydro-2-pyrazinyl)acetamide

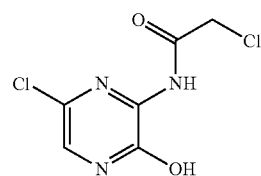 [SMILES: O=C(CCl)Nc1nc(Cl)cnc1O]

The mixture of 3-amino-5-chloro-2(1H)-pyrazinone (6 g, 28.8 mmol) and chloroacetic anhydride (19.7 g, 115 mmol) in $CH_3CN$ (80 mL) was stirred at 80dec overnight. The solvent was removed in vacuo. The resulting residue was washed with PE:EA (3:1) to afford the product (3 g, 56%), as black solid.

1H NMR (400 MHz, DMSO): δ 12.61 (brs, 1H), 10.32 (s, 1H), 7.40 (s, 1H), 4.49 (s, 2H).

(d) 6-Chloro-2H-pyrazino[2,3-b][1,4]oxazin-3 (4H)-one

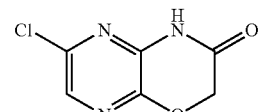

The mixture of 2-chloro-N-(6-chloro-3-oxo-3,4-dihydro-2-pyrazinyl)acetamide (3 g, 13.5 mmol) and KOH (2.3 g, 40.5 mmol) in Ethanol (50 mL) was stirred at rt overnight. The solvent was removed in vacuo and the resulting residue was purified by prep-HPLC to afford the product (1 g, 39%), as white solid.

1H NMR (400 MHz, DMSO): δ 11.85 (s, 1H), 7.86 (s, 1H), 4.90 (s, 2H).

(e) 6-Ethenyl-2H-pyrazino[2,3-b][1,4]oxazin-3(4H)-one

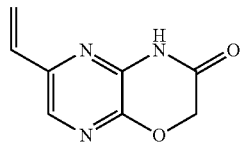

The mixture of 6-chloro-2H-pyrazino[2,3-b][1,4]oxazin-3(4H)-one (300 mg, 1.6 mmol), tributyl(vinyl)tin (1.52 g, 4.8 mmol) and Pd(PPh$_3$)$_4$ (184 mg, 0.16 mmol) in 1,4-dioxane (6 mL) and Toluene (6 mL) was stirred at 100° C. for 3 days under N$_2$. The mixture was filtered and the filtrate was concentrated in vacuo. The resulting residue was purified by prep-TLC (PE:EA 3:1) to afford the product (40 mg, 14%), as white solid.

1H NMR (400 MHz, CDCl3): δ 8.51 (s, 1H), 7.83 (s, 1H), 6.70 (dd, J=10.8 and 17.2 Hz, 1H), 6.15 (dd, J=1.2 and 17.2 Hz, 1H), 5.47 (dd, J=0.8 and 10.8 Hz, 1H), 4.92 (s, 2H)

(f) 3-Oxo-3,4-dihydro-2H-pyrazino[2,3-b][1,4]oxazine-6-carbaldehyde

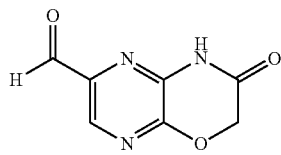 [SMILES: O=Cc1cnc2c(n1)NC(=O)CO2]

6-Ethenyl-2H-pyrazino[2,3-b][1,4]oxazin-3(4H)-one (40 mg, 0.22 mmol) was dissolved in THF (3 mL) and H$_2$O (0.6 mL). Then, NaIO$_4$ (141 mg, 0.66 mmol) and OsO$_4$ (1.1 mg, 0.0045 mmol) was added. The reaction mixture was stirred at r.t. for 5 h. 100 mL of water was added. The mixture was extracted with EtOAc (5×20 mL). The combined organic layers were dried over Na$_2$SO$_4$ and the solid was filtered off. The filtrate was purified by prep-TLC (PE:EA 1:1) to afford the product (20 mg, 49%).

1H NMR (400 MHz, DMSO): δ 11.95 (s, 1H), 9.86 (s, 1H), 8.36 (s, 1H), 4.99 (s, 2H).

Alternative Preparation B (a) 6-Chloro-2-pyrazinamine

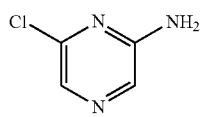

A solution of 2,6-dichloropyrazine (15 kg, 101.4 mol, 1.00 equiv) in water (20 L), ammonia water (25 L, 25%) was placed in a 100 L pressure tank reactor. The resulting solution was stirred for 6 h at 120° C. The reaction progress was monitored by TLC (EA:PE=1:1) until the starting material was consumed, and cooled to room temperature. The solids were collected by filtration. The solid was washed with water and dried. The solid was washed with petroleum ether to remove the unreacted starting materials. The product (7.8 kg, purity=95%, 60% yield) was obtained as a white solid.

(b) Methyl 6-amino-2-pyrazinecarboxylate

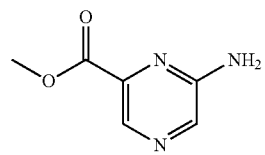

A solution of 6-chloro-2-pyrazinamine (4 kg, 31 mol, 1.00 equiv), Et3N (4.7 kg, 46.5 mol, 1.50 equiv), Pd(OAc)$_2$ (139 g, 0.62 mol, 0.02 equiv), dppf (343 g, 0.62 mol, 0.02 equiv) in methanol (60 L) was placed in a 100 L pressure tank reactor (10 atm).

The resulting solution was allowed to react for 5 h while maintaining the temperature at 85° C. The reaction progress was monitored by TLC (DCM:MeOH=20:1) until the starting material was consumed completely, and cooled to room temperature. The resulting mixture was concentrated under vacuum. The residue was washed with water 50 L. The filter was collected and dried. The product (3.8 kg, purity=95%, 80% yield) was obtained as a pale brown solid.

1H-NMR (300 MHz, DMSO-d6) δ: 8.27 (1H, s), 8.06 (1H, s), 6.87 (2H, b), 3.84 (3H, s).

LC-MS: m/z=154(M+H)+.

(c) Methyl 6-amino-3,5-dibromo-2-pyrazinecarboxylate

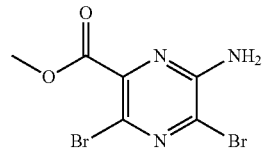

A solution of methyl 6-amino-2-pyrazinecarboxylate (17 kg, 111 mmol, 1.00 equiv) in N,N-dimethylformamide (100 L) was placed in a 200 L reactor. N-Bromosuccinimide (56 kg, 333 mol, 3.3 equiv) was added in several portions to above the solution while maintaining the temperature at 0° C. The reaction progress was monitored by TLC (EA:PE=1: 1) until the starting material was consumed completely. The reaction was quenched with 300 L water/ice. The solids were collected by filtration and dried. The crude product was re-crystallized in a solvent of MeOH (5 vol: 1 g). The product (17 kg, purity=98%, 54%) was obtained as a yellow solid.

1H-NMR (300 MHz, DMSO-d6) δ: 7.36 (2H, b), 3.87 (3H, s).

(d) Methyl 7-bromo-3-oxo-3,4-dihydro-2H-pyrazino[2,3-b][1,4]oxazine-6-carboxylate

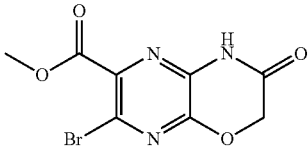 [SMILES: COC(=O)c1nc2c(nc1Br)OCC(=O)N2]

A solution of ethyl 6-amino-3,5-dibromo-2-pyrazinecarboxylate (2.5 kg, 8.1 mol, 1 equiv in methyl 2-hydroxyacetate (8.7 kg, 97.1 mol, 12 equiv) was placed in a 20 L 4-necked round-bottom flask under $N_2$. t-BuOK (2.71 kg, 24.3 mol, 3 equiv) was added in several portions to above the solution while maintaining the temperature at 50-60° C. (about 1 hours added completion). The resulting solution was allowed to react for 1 h while maintaining the temperature at 50-60° C. The reaction progress was monitored by LCMS until the starting material was consumed completely. The reaction mixture was cooled to room temperature. The reaction was then quenched by 20 L water. The pH value of the solution was adjusted to 3-4 with 6M hydrogen chloride. The solids were collected by filtration and dried. The crude product was purified by chromatogram on silica gel with DCM:EA (1:1) to give the desired product (1.3 kg, 95% purity, 56% yield) as a light yellow solid 1H-NMR (300 MHz, DMSO-d6) δ: 11.97 (1H, b), 4.98 (2H, s), 3.88 (3H, s).

(e) Methyl 3-oxo-3,4-dihydro-2H-pyrazino[2,3-b][1,4]oxazine-6-carboxylate

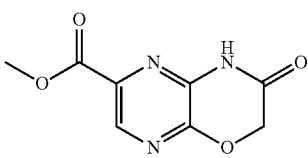

A solution of NaOAc (1000 g, 12.2 mol, 2.06 equiv), Pd/C (10%, 340 g), methyl 7-bromo-3-oxo-3,4-dihydro-2H-pyrazino[2,3-b][1,4]oxazine-6-carboxylate in MeOH (34 L) and THF (34 L) was placed in a 100 L pressure tank reactor (3 atm). The resulting solution was stirred for 3 h at 30° C. The reaction progress was monitored by LCMS until the starting material was consumed completely. The reaction mixture was hot to 60° C. for 1 h. A filtration was performed to remove Pd/C. The resulting mixture was washed with THF (20 L×2). The resulting mixture was concentrated (to 1 L) under vacuum. The solids were collected by filtration and added in 2 L water. The pH value of the mixture was adjusted to 3-4 with 3M hydrogen chloride. The solids were collected by filtration and dried. The product (0.9 kg, 98% purity, 80% yield) was obtained as a yellow solid.

1H-NMR (300 MHz, DMSO-d6) δ: 11.94 (1H, s), 8.39 (1H, S), 4.98 (2H, s), 3.86 (3H, s).

(f) 6-(hydroxymethyl)-2H-pyrazino[2,3-b][1,4]oxazin-3 (4H)-one

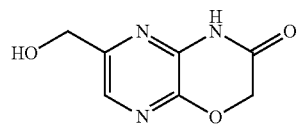

A solution of methyl 3-oxo-3,4-dihydro-2H-pyrazino[2,3-b][1,4]oxazine-6-carboxylate (400 g, 2.22 mol, 1 equiv) in THF (8 L) was placed in a 20 L 4-necked round-bottom flask under $N_2$. LiBHEt$_3$ (1M) (6.1 L, 3.2 equiv) was added dropwise to the solution, while maintaining the temperature at −10-0° C. (about 1 hours added completion). The resulting solution was allowed to react for 1 h while maintaining the temperature at −10-0° C. The reaction progress was monitored by LCMS until the starting material was consumed completely. The pH value of the solution was adjusted to 3-4 with 6M hydrogen chloride (about 500 ml). The resulting solution was extracted with THF (2×5 L) and the organic layers were combined. The organic phase was dried over anhydrous sodium sulfate. The organic phase was concentrated (to 2 L) under vacuum. The solids were collected by filtration and dried. The product (173 g, 98% purity, 50% yield) was obtained as a yellow solid.

1H-NMR (300 MHz, DMSO-d6) δ: 11.57 (1H, s), 7.79 (1H, s), 5.47 (1H, b), 4.86 (2H, s), 4.46 (2H, s).

(g) 3-Oxo-3,4-dihydro-2H-pyrazino[2,3-b][1,4]oxazine-6-carbaldehyde

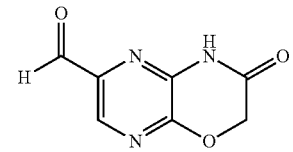 [SMILES: O=Cc1cnc2c(n1)NC(=O)CO2]

A solution of 6-(hydroxymethyl)-2H-pyrazino[2,3-b][1,4]oxazin-3(4H)-one (200 g, 1.1 mol, 1 equiv) in THF (8 L) and DCE (4 L) was placed in a 20 L 4-necked round-bottom flask. MnO$_2$ (1150 g, 13.3 mol, 12 equiv) was added in several portions to above the solution while maintaining the temperature at 75-80° C. (about 24 hours added completion). The reaction progress was monitored by LCMS until the starting material was consumed completely. A filtration was performed to remove MnO$_2$. The filtrate was concentrated (to 2 L) under vacuum. The solids were collected by filtration and dried. The product (110 g, 98% purity, 60% yield) was obtained as a off-white solid.

1H-NMR (300 MHz, DMSO-d6) δ: 11.98 (1H, s), 9.88 (1H, s), 8.38 (1H, s), 5.01 (2H, s).

Synthesis Scheme A

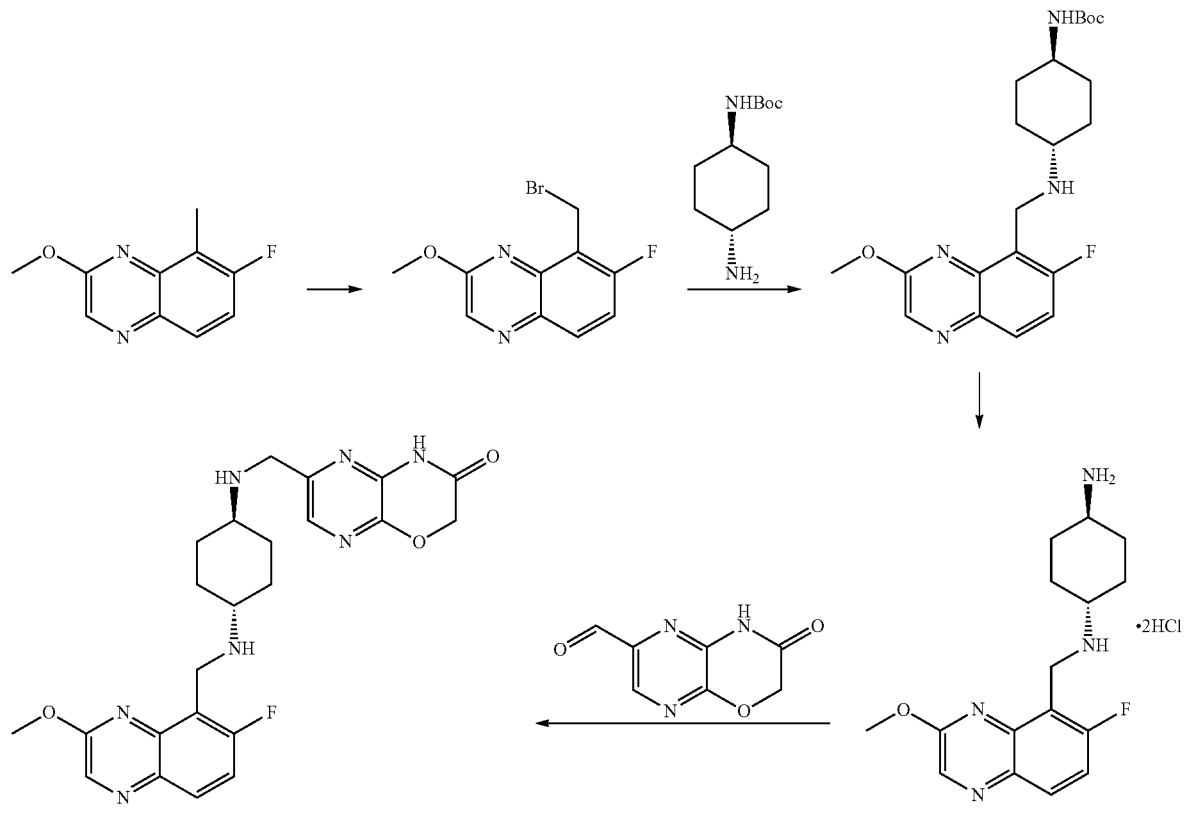

Example 1:
8-(Bromomethyl)-7-fluoro-2-methoxyquinoxaline

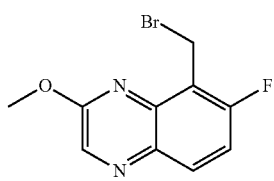

To a cooled (0° C.) solution of 7-fluoro-8-methyl-2-(methyloxy) quinoxaline (5.037 g, 26.2 mmol) in chloroform (101 ml) was added NBS (5.13 g, 28.8 mmol) portionwise over 5 minutes followed by benzoyl peroxide (0.317 g, 1.310 mmol) portionwise over 1 minute. The ice bath was removed and the reaction was heated to reflux in an oil bath (60° C.). A 120 W lamp was placed to shine on the reaction inside an aluminum foil tent. The reaction was refluxed under the light for 3.5 hours, then cooled to rt. Water was added to the reaction (100 mL) and the organic layers were extracted with $CH_2Cl_2$ (3×30 mL). The combined organic layers were dried over $Na_2SO_4$, filtered and concentrated to give 8-(Bromomethyl)-7-fluoro-2-methoxyquinoxaline as a tan powder (7.02 g, 25.9 mmol, 99% yield).

LCMS: m/z 271.2 (M+), 273.2 (M+2+).

$^1$H NMR (CDCl$_3$) ppm: 4.19 (s, 3H), 5.10 (d, J=1.52 Hz, 2H), 7.36 (t, J=9.09 Hz, 1H), 8.02 (dd, J=9.22, 5.94 Hz, 1H), 8.49 (s, 1H).

Example 2: Tert-butyl ((1R,4R)-4-((((6-fluoro-3-methoxyquinoxalin-5-yl)methyl)amino)cyclohexyl)carbamate

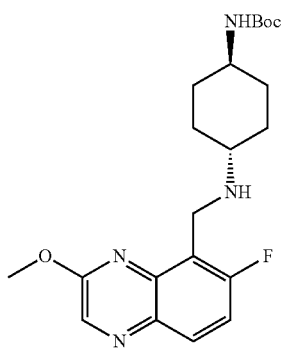 [SMILES: COc1cnc2ccc(F)c(CN[C@H]3CC[C@H](NC(=O)OC(C)(C)C)CC3)c2n1]

To a solution of 8-(bromomethyl)-7-fluoro-2-(methyloxy) quinoxaline (4.5 g, 16.60 mmol) and 1,1-dimethylethyl (trans-4-aminocyclohexyl)carbamate (4.27 g, 19.92 mmol) in tetrahydrofuran (THF) (100 mL) was added $K_2CO_3$ (2.75 g, 19.92 mmol) at RT, and stirred overnight. THF was removed under reduced pressure and water (50 mL) was added to the residue. This mixture was extracted with $CH_2Cl_2$ (3×100 mL). The combined organic layers were dried over $Na_2SO_4$, filtered and concentrated. The residue was then purified by combiflash with 85% $CH_2Cl_2$, 14% MeOH and 1% $NH_4OH$ as eluate to give tert-butyl ((1r,4r)-

4-(((6-fluoro-3-methoxyquinoxalin-5-yl)methyl)amino)cyclohexyl)carbamate (4.57 g, 11.29 mmol, 68% yield).

LCMS: m/z 405.3 (M+1+).

$^1$H NMR (CDCl$_3$) δ: 1.11 (q, J=11.7 Hz, 2H), 1.20-1.42 (m, 4H), 1.46 (s, 9H), 2.03 (br. d, J=10.4 Hz, 4H), 2.43 (br. s., 1H), 3.44 (br. s., 1H), 4.12 (s, 3H), 4.37 (s, 2H), 7.35 (t, J=9.1 Hz, 1H), 7.95 (dd, J=9.1, 5.8 Hz, 1H), 8.47 (s, 1H).

Example 3: (1R,4R)—N1-((7-fluoro-2-methoxyquinoxalin-8-yl)methyl)cyclohexane-1,4-diamine Dihydrochloride

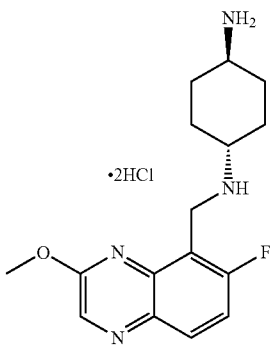 [SMILES: COc1cnc2ccc(F)c(CN[C@H]3CC[C@H](N)CC3)c2n1]

To a 10 L flask under nitrogen was added tert-butyl (1r,4r)-4-((7-fluoro-2-methoxyquinoxalin-8-yl)methylamino)cyclohexylcarbamate (150 g), DCM (2 L) and methanol (2 L). This was followed by the dropwise addition of 4M HCl in dioxane (1.38 L), T$_{max}$ 25° C. The solution became a slurry and was allowed to stir overnight. LC analysis indicated 95% product and 3% SM. The reaction mixture was concentrated in vacuo. The residue was reconcentrated in vacuo from MeOH (3×1 L) this gave (1r,4r)-N1-((7-fluoro-2-methoxyquinoxalin-8-yl)methyl)cyclohexane-1,4-diamine dihydrochloride as a yellow/white solid. A total of 127 g was obtained, however, $^1$H NMR assay indicated an activity of 87%. 110 g active (79% yield).

$^1$H NMR (D$_2$O, 270 MHz): δ, 1.39-1.71 (4H, m), 2.07-2.24 (2H, m), 2.32-2.47 (2H, m), 3.12-3.44 (2H, m), 3.67 (2H, s), 4.06 (3H, s), 6.31 (6H, s, maleic acid peak as internal standard), 7.45 (1H, t, J=9.5 Hz), 8.00 (1H, dd, J=5.9 Hz and 9.2 Hz) and 8.40 (1H, s).

Example 4: 6-((((1R,4R)-4-(((6-fluoro-3-methoxyquinoxalin-5-yl)methyl)amino)cyclohexyl)amino)methyl)-2H-pyrazino[2,3-b][1,4]oxazin-3(4H)-one

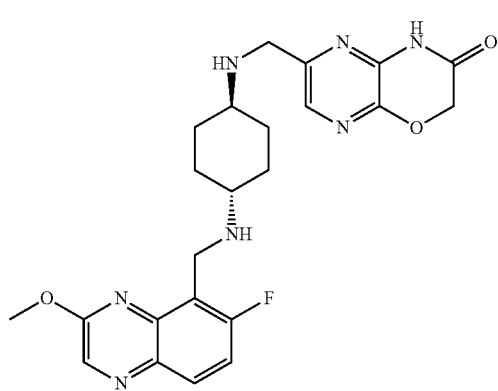 [SMILES: COc1cnc2ccc(F)c(CN[C@H]3CC[C@H](NCc4cnc5c(n4)NC(=O)CO5)CC3)c2n1]

To a 3 necked flask under nitrogen was added (1R,4R)—N'-((7-fluoro-2-methoxy quinoxaline-8-yl) methyl) cyclohexane 1,4 diamine dihydrochloride (100.6 g active), 3,4 dihydro-3-oxo-2H-pyrazino[2,3b][1,4]oxazine-6-carbaldehyde (43 g), IPA (1 L), chloroform (6.12 L) and finally triethylamine (124.8 mL). The reaction was then allowed to stir overnight as a slurry. Next day a lot of the solid had dissolved but not all (same as small scale). Sodium triacetoxyborohydride (141.3 g) was added portionwise to the reaction over 20 mins. The reaction was then allowed to stir for 3 h. A sample was analysed via LCMS and this showed 82% product, 8.6% amine and 1.2% aldehyde. The reaction mixture was transferred to a 20 L flask containing 6.6 L of saturated NaHCO$_3$ solution. The organics were separated off and the aqueous reextracted with DCM:MeOH (2×6 L:0.6 L). The organics were dried, filtered and concentrated in vacuo. The residue was subject to column chromatography (10 kg silica) eluting with 10% methanol:DCM to 25% methanol:DCM to give 6-((((1R,4R)-4-(((6-fluoro-3-methoxyquinoxalin-5-yl)methyl)amino)cyclohexyl)amino)methyl)-2H-pyrazino[2,3-b][1,4]oxazin-3(4H)-one. LCMS of the product indicated a purity of 98.9% with a single impurity of 0.46%. The material was dried under vacuum at 50° C. overnight and then at 60° C. for 5 h to provide the product 77.2 g (69% yield). $^1$H NMR (DMSO-d; 500 MHz): δ (ppm) 11.66-11.69 (m, 1H), 9.15-9.22 (m, 1H), 8.90-8.96 (m, 1H), 8.60-8.66 (m, 1H), 8.12-8.16 (m, 1H), 7.90-7.93 (m, 1H), 7.58-7.64 (m, 2H), 4.90 (s, 5H), 4.59-4.64 (m, 1H), 4.14-4.18 (m, 1H), 4.13 (s, 6H), 3.06-3.13 (m, 1H), 2.29-2.35 (m, 1H), 2.21-2.25 (m, 1H), 1.45-1.50 (m, 1H). LCMS, indicated a purity of 98.6% with the single largest impurity at a level of 0.47%. MeOH content by GC was 0.04%.

Example 5: 6-((((1R,4R)-4-(((6-fluoro-3-methoxyquinoxalin-5-yl)methyl)amino)cyclohexyl)amino)methyl)-2H-pyrazino[2,3-b][1,4]oxazin-3(4H)-one, Hydrochloride 6-((((1R,4R)-4-(((6-fluoro-3-methoxyquinoxalin-5-yl)methyl)amino)cyclohexyl)amino)methyl)-2H-pyrazino[2,3-b][1,4]oxazin-3(4H)-one (20 g, 42.8 mmol) was dissolved in Methanol (130 mL) and Dichloromethane (DCM) (130 mL), then was treated with HCl (34.2 mL, 42.8 mmol) 1.25M in EtOH slowly at 0 degree. The solution became cloudy as salt was precipitate out. The solid was collected and yielded 6-((((1R,4R)-4-(((6-fluoro-3-methoxyquinoxalin-5-yl)methyl)amino)cyclohexyl)amino)methyl)-2H-pyrazino[2,3-b][1,4]oxazin-3(4H)-one, Hydrochloride (20 g, 39.7 mmol, 93% yield).

$^1$H NMR (DMSO, 270 MHz): δ, 0.75-1.36 (4H, m), 1.60-2.05 (4H, m), 2.16-2.47 (2H, m), 3.36 (1H, br s), 3.70 (2H, s), 4.06 (3H, s), 4.19 (2H, s), 4.85 (2H, s), 7.52 (1H, t, J=9.2 Hz), 7.78 (1H, s), 7.97 (1H, dd, J=5.9 Hz and 9.2 Hz) and 8.59 (1H, s).

MS (ES$^+$) m/z 468.2 (MH$^+$).

Synthesis Scheme B

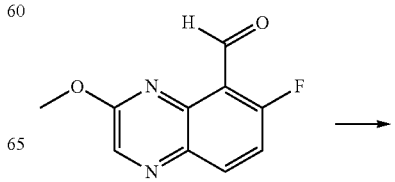

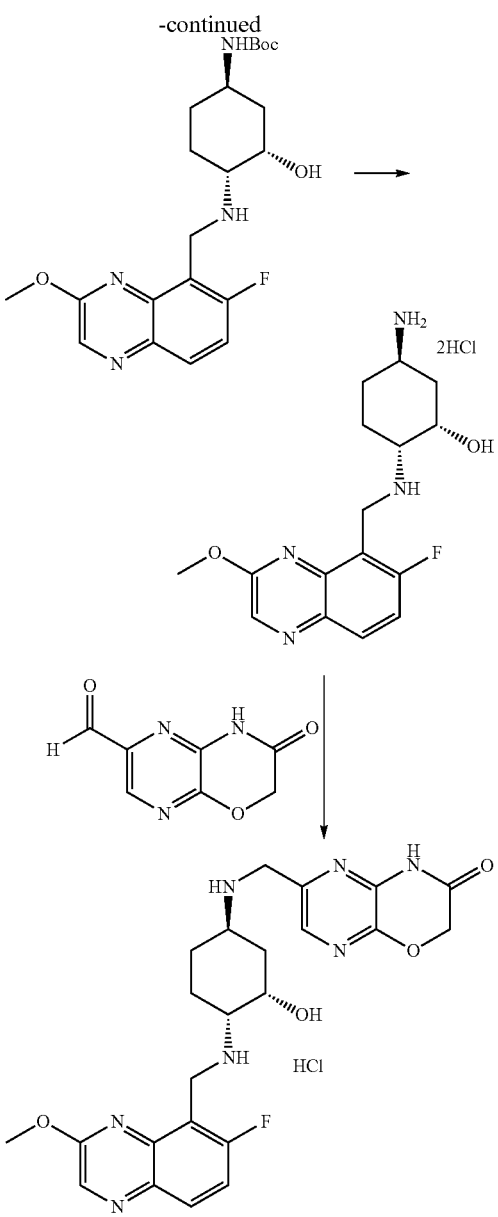

Example 6: tert Butyl (1R,3S,4R)-4-((7-fluoro-2-methoxyquinoxalin-8-yl)methylamino)-3-hydroxy-cyclohexylcarbamate

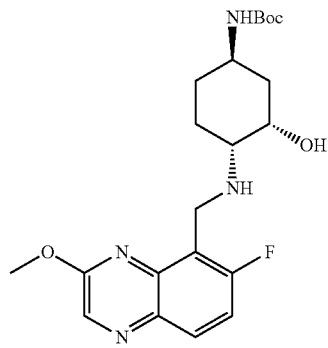 [SMILES: COc1cnc2ccc(F)c(CN[C@@H]3CC[C@@H](NC(=O)OC(C)(C)C)C[C@@H]3O)c2n1]

To a 10 L flask under $N_2$ was charged tert Butyl (1R,3S,4R)-4-amino-3-hydroxy cyclohexylcarbamate (87.5 g) fol- lowed by 6-fluoro-3-methoxyquinoxalin-5-carbaldehyde (88 g, 70.5 g active) at rt. CHCl$_3$ (4.4 L) was charged followed by MeOH (612 mL)—Pot temp 15° C. Stirred the solution formed at rt for 20 hrs. To the RM (clear solution pot temp 17.4° C.) NaBH(OAc)$_3$ (161 g) was added in portions over a period of 20 min—max. pot temp=22.4° C. The RM was stirred for 1 hr 30 min & sampled for TLC (1:1 hept-EtOAc & 5% MeOH in DCM Vis:UV) and LC/LC-MS (UP850RM). After a total of 2 hrs the rxn mix. was quenched with sat. NaHCO$_3$(4.5 L) in portions. Stirred for 15-20 min & layers separated. The AQ layer was ext. with 10% MeOH in DCM (2 L)—LC of AQ layer=UP850AQ. The combined org. layers were dried (Na$_2$SO$_4$), filtered and evap. u/v @ 40-45° C. Yellow solid obt. wt in flask 238.4 g. $^1$HNMR (CDCl$_3$)/LC-MS=UP850. The crude product was chromatographed on silica (8 Kg) packed in DCM and eluted with DCM (20 L); 0.5% MeOH in DCM (20 L); 1% MeOH in DCM (20 L); 2% MeOH in DCM (20 L); 4% MeOH in DCM (20 L); 5% MeOH in DCM (20 L+20 L); 7.5% MeOH in DCM (20 L); 10% MeOH in DCM (20 L). Frac. Size ~9-10 L. F13→16 evap u/v→pale yellow solid 114.3 g (in flask). $^1$HNMR (CDCl$_3$)/LC/LC-MS=UP850A (by NMR ~4% MeOH→active=109.7 g) by LC 97.8% (dimer <1%) by LC-MS 96.9% dimer (1%). F17→20 evap. u/v along with F12 to give 43.7 g (in flask) of tert Butyl (1R,3S,4R)-4-((7-fluoro-2-methoxyquinoxalin-8-yl)methyl-amino)-3-hydroxycyclohexylcarbamate as yellow solid=UP850Bacteroides $^1$HNMR (CDCl$_3$)/LC/LC-MS=UP850B by NMR ~7.7% DCM+~2.3% MeOH, LC 91.5% (2.74% dimer)

MS (ES$^+$) m/z 421.5 (MH$^+$).

Example 7: (1S,2R,5R)-2-((7-fluoro-2-methoxyqui-noxalin-8-yl)methylamino)-5-aminocyclohexanol Dihydrochloride

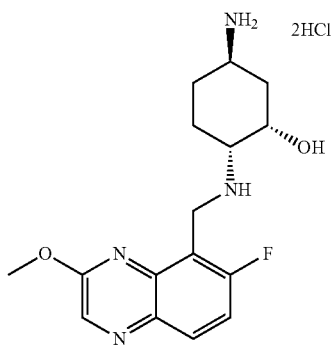 [SMILES: COc1cnc2ccc(F)c(CN[C@@H]3CC[C@@H](N)C[C@@H]3O)c2n1]

To a 5 L flask was charged a solution of tert Butyl (1R,3S,4R)-4-((7-fluoro-2-methoxyquinoxalin-8-yl)methyl-amino)-3-hydroxycyclohexylcarbamate (114.3 g, 109.7 g active) in DCM (1.1 L) and MeOH (1.1 L) at rt. 4M HCl in dioxane (979 mL) was added over a period of 1 hr 30 min keeping pot temp <30° C.—solid starts to ppt. at the end of addn. Stirred at rt for 20 hrs. Sampled the RM (suspension) for LC (UP851RM)—by LC rxn complete. UP851 & UP852 merged & evap. u/v @ 40-45° C. (F/C, PTFE pump). 152 g (in flask) of light brown solid obt. $^1$H-NMR (DMSO-d$_6$)=UP851, $^1$H-NMR (MeOH-d$_4$)= UP851CD3OD, $^1$H-NMR assay (fumaric acid, CD$_3$OD)= UP851ASSAY. By NMR assay 90% active. LC-MS (GSK method)=UP851. 2.47 g of the solid was slurried in DCM (25 mL) for 2 hrs→until all the lumps break up to a fine powder, and filtered & washed with DCM (2×10 mL) and pulled dry for 15-20 min. Packed wt 2.37 g. GSK LC-MS/¹H-NMR (CD₃OD)=UP851A. LC-MS analysis received. UP851→97%, dimer ~0.1% largest impurity ~0.3% (GSK method). UP851A→97.18%. Slurry in DCM not required. All used in the next stage as it is.

¹H NMR (d₃-MeOH, 270 MHz): δ, 1.37-2.55 (6H, m), 3.46-3.64 (2H, m), 4.21 (3H, s), 4.58 (1H, br s), 4.71-4.89 (2H, m), 4.95 (10H, s), 7.56 (1H, t, J=9.2 Hz), 8.15 (1H, dd, J=5.9 and 9.5 Hz) and 8.56 (1H, s).

Example 8: 6-((((1R,3S,4R)-4-(((6-fluoro-3-methoxyquinoxalin-5-yl)methyl)amino)-3-hydroxy-cyclohexyl)amino)methyl)-2H-pyrazino[2,3-b][1,4]oxazin-3(4H)-one Hydrochloride

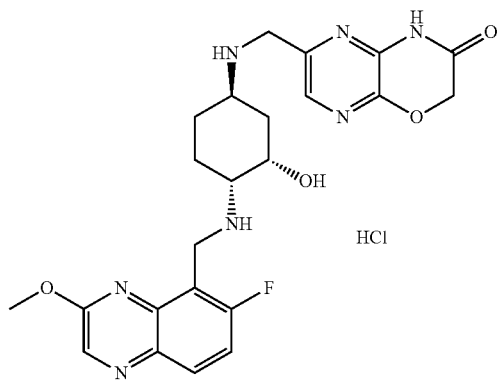 [SMILES: COc1cnc2ccc(F)c(CN[C@@H]3CC[C@@H](NCc4cnc5c(n4)NC(=O)CO5)C[C@@H]3O)c2n1 ; Cl]

(1S,2R,5R)-2-((7-fluoro-2-methoxyquinoxalin-8-yl)methylamino)-5-aminocyclohexanol.2HCl (133 g active) was suspended in CHCl₃ (6.65 L) under N₂ at rt. 3,4-dihydro-3-oxo-2H-pyrazino[2,3-b][1,4]oxazine-6-carbaldehyde (57.7 g active) was charged followed by IPA (930 mL) and NEt₃ (142 mL). The suspension was stirred at rt under N₂ overnight. A clear solution had formed. Pot temp=19.4° C. NaBH(OAc)₃ (144 g) was charged over a period of 30 min. max pot temp obsd. was 23.2° C. Stirred for 2 hrs and sampled for TLC (10% MeOH in DCM, Vis:UV)—by TLC the aldehyde was detected. NaBH(OAc)₃ (36 g) was added and stirring contd. at rt for another 1 hr and sampled for TLC & LC-MS (UP855RM, GSK method)—by TLC aldehyde consumed. The RM was diluted with CHCl₃ (2 L) & stirred 15 min. The RM was vac. transferred into a 20 L flask containing sat. NaHCO₃(9.5 L) over a period of 15-20 min. Stirred for 15 min+15 min and the layers were separated. The aq. Layer was ext. With 20% MeOH in DCM (3×3 L). The combined organic layers were washed with brine (1×2 L) and dried & filtered. LC-MS (UP855RM) received indicated 87.35% prod, 2.17% aldehyde, 5.05% amine no other impurity was individually >0.7%. The org. Layer evap. u/v @ 40-45° C. 245.8 g (in flask) of light brown solid obt. ¹HNMR (DMSO-d₆)=UP855=LC-MS (GSK). By NMR ~12.5% IPA, ~5% EtOH (from CHCl₃); ~0.5% DCM. By LC-MS 92.22% prod, 2.45% aldehyde, 2.25% amine. The solid was taken up in DCM (2 L) & MeOH (500 mL) & adsorbed on silica (250 g) for chromatography on silica (10 Kg) packed in DCM. The material was purified using a gradient of 10% MeOH:DCM to 20% MeOH:DCM to 0.5% NH₄OH, 19.5% MeOH:DCM and this led to the elution of the product. A total of 100 g was isolated with a purity of 96.99& by LCMS. A number of recrystallisation/slurry were looked at for the free base and salt. The three most promising results were scaled up to gram scale.

A hot ethanol slurry (40 vol EtOH added in 10 vol portions), cool down and filter was performed on the free base (4.77 g). This resulted in material with a purity of 98.2%. Recovery 80% (3.82 g).

A hot ethanol slurry (50 vol EtOH added in 10 vol portions), cool down and filter was performed on the salt (2.46 g). This resulted in material with a purity of 98.3%. Recovery 73% (1.93 g).

A hot ethanol slurry (50 vol EtOH added in 10 vol portions), cool down to 50° C. and added TBME (10 vol), cool to rt and filter off the salt (2.42 g). This resulted in material with a purity of 98.1%. Recovery 76% (2.42 g).

A portion of the material (1 g) was recolumned using 5-8% MeOH, 0.5% NH₄OH and DCM and this led to the isolation of 0.88 g (88%) of material with a purity of 98.6%.

After examination of a number of recrystallisation/slurry conditions for the salt/free base, it was found that a hot slurry in ethanol (40 vol) of the free base followed by cooling to rt and filtration gave the required purity (98.2%) and yield. The slurry was trialled on a ~4 g scale successfully and thus the process was repeated on the bulk. Small scale salt formation using purified free base showed 6% methanol present, which re-concentrating from ethanol and drying did not remove. The salt formation was repeated using MeOH (20 vol), EtOH (20 vol) and DCM (36 vol). The material obtained from this salt formation had the desired LC purity and with methanol at an acceptable level. The process was repeated on the bulk of the material to give 79.3 g of 6-((((1R,3S,4R)-4-(((6-fluoro-3-methoxyquinoxalin-5-yl)methyl)amino)-3-hydroxycyclohexyl)amino)methyl)-2H-pyrazino[2,3-b][1,4]oxazin-3(4H)-one hydrochloride with a purity of 98.4% by LCMS.

¹H NMR (DMSO, 270 MHz): δ, 1.16-1.69 (3H, m), 1.74-1.96 (1H, m), 1.96-2.29 (2H, m), 2.87 (1H, br s), 2.96-3.13 (1H, m), 3.92 (2H, br s), 4.10 (3H, s), 4.21 (1H, br s), 4.40 (2H, br s), 4.89 (2H, s), 5.17 (1H, br s), 7.58 (1H, t, J=9.2 Hz), 8.05 (1H, dd, J=5.9 and 9.2 Hz) and 8.62 (1H, s).

MS (ES⁺) m/z 484.1 (MH⁺).

Central Linker

Tert-Butyl ((1R,3S,4R)-4-amino-3-hydroxycyclohexyl)carbamate

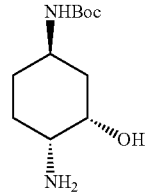 [SMILES: CC(C)(C)OC(=O)N[C@@H]1CC[C@@H](N)[C@@H](O)C1]

Scheme:

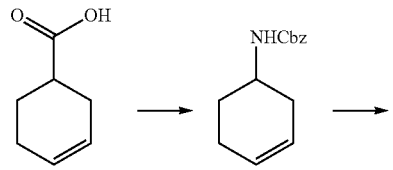

-continued

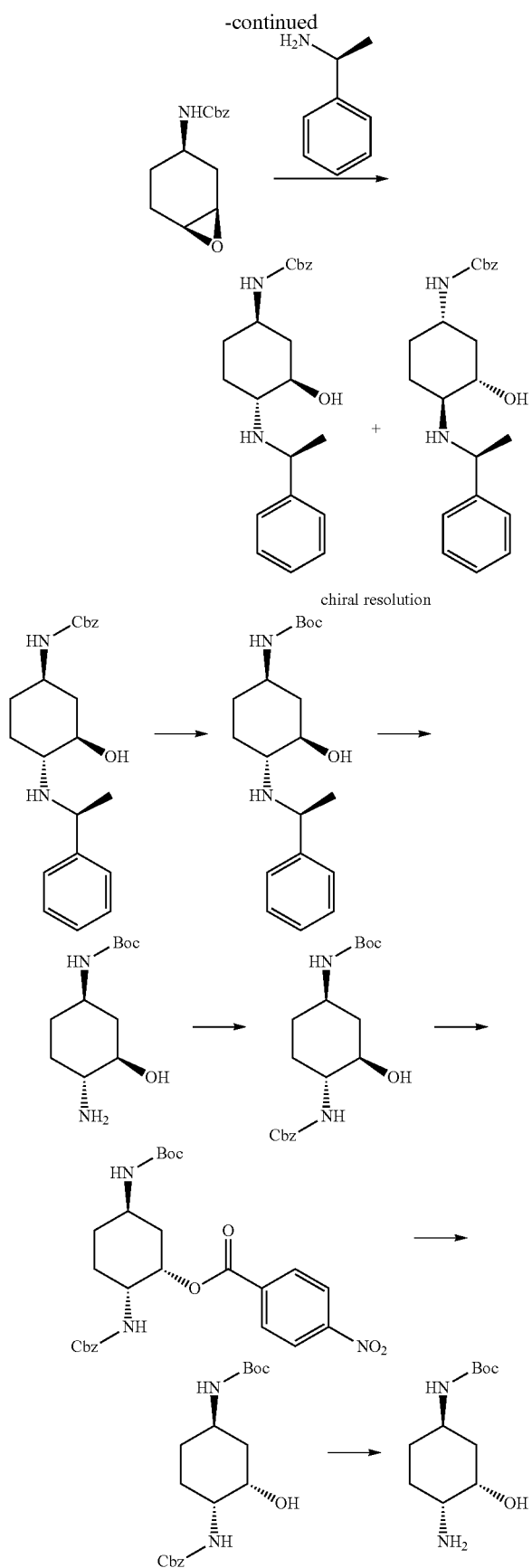

Example 9: Benzyl cyclohex-3-en-1-ylcarbamate

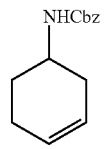

To a solution of cyclohex-3-enecarboxylic acid (17.5 kg, 138.9 mol, 1.00 equiv) in toluene (305 L) was added TEA (15.4 kg, 152.5 mol, 1.10 equiv), Diphenylphosphoryl azide (DPPA) (40.1 kg, 145.8 mol, 1.05 equiv). The reaction was purged with an inert atmosphere of nitrogen. The mixture was stirred at 25° C. for 1.5 hours. Then the resulting solution was heated for an additional 2.5 hours while the temperature was maintained at 110° C. The phenylmethanol (16.5 kg, 152.8 mol, 1.10 equiv) was added dropwise into the above solution. The resulting solution was stirred for 8 hours at 110° C. The reaction progress was monitored by TLC (EA:PE=1:4) until the starting material was consumed completely. The resulting mixture was concentrated under vacuum. The residue was diluted with 500 L of DCM and then washed with 2×100 L of 10% 2-hydroxypropane-1,2,3-tricarboxylic acid and 2×50 L of saturate sodium bicarbonate and 1×100 L of $H_2O$. The organic layer was dried over anhydrous sodium sulfate and concentrated under vacuum. The residue was applied onto a silica gel column with ethyl acetate/petroleum ether (0-10%) to give 14 kg (purity=97%, yield=44%) of benzyl cyclohex-3-enylcarbamate as a white solid.

ES, (m/z): 232 $[M+1]^+$

1H-NMR (300 MHz, $CDCl_3$), δ: 1.560-1.657 (1H, m), 1.858-1.957 (2H, m), 2.127-2.153 (2H, m), 2.388-2.446 (1H, d, J=17.4 Hz), 3.893 (1H, s), 4.824 (1H, s), 5.118 (1H, s), 5.581-5.725 (2H, m), 7.280-7.393 (5H, m).

Example 10: benzyl (1R,3R,6S)-7-oxabicyclo[4.1.0]heptan-3-ylcarbamate

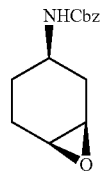

To a solution of benzyl cyclohex-3-enylcarbamate (2.2 kg, 9.5 mol, 1.00 equiv) in dichloromethane (25 L), 3—Chloroperoxybenzoic acid (2.14 kg, 12.4 mol, 1.30 equiv) was added in portions at 10-15° C. The resulting solution was stirred for 4 h at 15° C. The reaction progress was monitored by TLC (DCM/PE/TBME=1/10/10) until the starting material was consumed completely. The solids were filtered out and a filtration was performed. The filtrate was washed with 5 L of 22% sodium phrosulfite and 7.5 L 15% of sodium bicarbonate. The resulting mixture was washed with 5 L of brine. The organic layer was collected and dried over anhydrous sodium sulfate and concentrated under vacuum. The residue was applied onto a silica gel column with ethyl acetate/petroleum ether (0-1/4). This resulted in 750 g (purity=98%, yield=32%) of benzyl (1R,3R,6S)-7-oxa-bicyclo[4.1.0]heptan-3-ylcarbamate as a white solid.

(ES, m/z): 248 [M+1]+

1H-NMR (300 MHz, CDCl3), δ: 1.485-1.561 (2H, m), 1.832-1.998 (2H, m), 2.084-2.278 (2H, m), 3.192 (2H, s), 3.755 (1H, s), 5.051 (2H, s), 5.093-5.135 (1H, d, J=12.6 Hz), 7.280-7.411 (5H, m).

Example 11: benzyl ((1R,3R,4R)-3-hydroxy-4-(((S)-1-phenylethyl)amino)cyclohexyl)carbamate

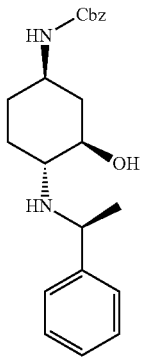 [SMILES: C[C@H](N[C@@H]1CC[C@@H](NC(=O)OC(C)(C)C)C[C@H]1O)c1ccccc1]

To a solution of benzyl (1R,3R,6S)-7-oxa-bicyclo[4.1.0]heptan-3-ylcarbamate (500 g, 2.02 mol, 1.00 equiv) in ACN (10 L) was added LiClO4 (2146 g, 20.2 mol, 10.00 equiv) and (S)-1-phenylethanamine (269 g, 2.22 mol, 1.10 equiv) at 25° C. The resulting solution was stirred for 18 h at 85° C. The reaction progress was monitored by HPLC until the starting material was consumed completely. The resulting solution was diluted with 10000 mL of DCM and then washed with 2×5000 mL of H2O and 5000 mL of brine. The organic layer was dried over anhydrous sodium sulfate and concentrated under vacuum. The crude product was purified by re-crystallization in 4000 mL EA. This resulted in 390 g (chemical purity=98%, yield=52%) of PH-GBI-16-50 isomers as a white solid. Chiral resolution: To a solution of PH-GBI-16-50 isomers (390 g, 1.06 mol, 1.00 equiv) in ethanol (4.7 L) was added D-DBTA (387 g, 1.08 mol, 1.00 equiv). The resulting solution was stirred for 30 min at 78° C. and cooled to 0° C. with a water/ice bath. The solids were collected by filtration, and the filtrate was reserved. The solids was added to ethanol (3.1 L), the resulting solution was stirred for 1 hour at 78° C. and cooled to 0° C. with a water/ice bath. The solids were collected by filtration, and the filtrate was reserved. The solid was added to 1 L H2O, Sodium carbonate was employed to adjust the pH to 9-10. The resulting solution was extracted with EtOAc (2*1 L) and the organic layer was dried with Na2SO4 and concentrated under vacuum to give 134 g of benzyl ((1R,3R,4R)-3-hydroxy-4-(((S)-1-phenylethyl)amino)cyclohexyl)carbamate (optical purity=99% ee, yield=23%) as a colourless syrup.

The above filtrate was concentrated and basified and concentrated with the same method above. This resulted 240 g white solid. The solid was recrystallized in 720 mL MeOH. The filtrate concentrated under vacuum. The product was recrystallized in 450 mL MeOH. This resulted PH-GBI-16-50B 150 g (purity=94% ee) as a white solid. The product was recrystallized once more in 150 mL MeOH, and to give 85 g of benzyl ((1S,3S,4S)-3-hydroxy-4-(((S)-1-phenylethyl)amino)cyclohexyl)carbamate (purity=99% ee, yield=14%).

(ES, m/z): 369 [M+1]+

1H-NMR (300 MHz, CDCl3), δ: 0.978-1.127 (3H, m), 1.361-1.383 (3H, d, J=6.6 Hz), 2.004-2.038 (2H, m), 2.144-2.305 (2H, m), 3.223-3.303 (1H, m), 3.583-3.608 (1H, d, J=7.5 Hz), 3.968-4.033 (1H, m), 4.616-4.641 (1H, d, J=7.5 Hz), 5.081 (2H, s), 7.233-7.389 (8H, m).

Example 12: tert-butyl ((1R,3R,4R)-3-hydroxy-4-(((S)-1-phenylethyl) amino)cyclohexyl)carbamate

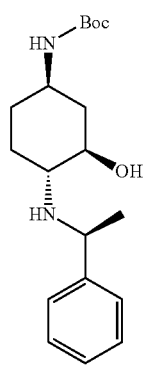

To a solution of benzyl ((1R,3R,4R)-3-hydroxy-4-(((S)-1-phenylethyl)amino)cyclohexyl)carbamate (400 g 1.09 mol, 1.00 equiv) in methanol (6000 mL), Boc2O (236 g, 1.08 mol, 1.00 equiv) and Palladium carbon (wet) (40 g) were added. Then the hydrogen gas was then bubbled into the mixture. The resulting solution was stirred for 4 hours at 15 degree C. The reaction progress was monitored by LCMS until the starting material was consumed completely. The solids were filtered out. The filtrate was concentrated under vacuum. The residue was dissolved in 400 ml EA, A lot of white solid was separated out and the solids were collected by filtration. This resulted 315 g of tert-butyl ((1R,3R,4R)-3-hydroxy-4-(((S)-1-phenylethyl)amino)cyclohexyl)carbamate (purity=99% ee, yield=87%) as a white solid. (ES, m/z): 335 [M+1]+1H-NMRδ: 0.950-1.101 (3H, m), 1.354-1.376 (3H, d, J=6.6 Hz), 1.463 (9H, s), 1.993-2.026 (2H, m), 2.139-2.272 (2H, m), 3.206-3.289 (1H, m), 3.506 (1H, s), 3.966-4.032 (1H, m), 4.351-4.372 (1H, d, J=6.3 Hz), 7.239-7.378 (5H, m).

Example 13: tert-butyl ((1R,3R,4R)-4-amino-3-hydroxycyclohexyl)carbamate

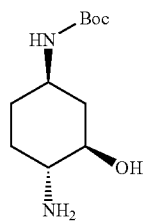

To a solution of 3-hydroxy-4-(((S)-1-phenylethyl)amino)cyclohexyl)carbamate (315 g, 0.943 mol, 1.00 equiv) in methanol (4500 mL), Pd(OH)$_2$/C (wet) (160 g) was added carefully under N$_2$. Then the hydrogen gas was then bubbled into the mixture. The resulting solution was stirred for 12 hours at 30 degree C. The reaction progress was monitored by LCMS until the starting material was consumed completely. The solids were filtered out and the filtrate was concentrated under vacuum. This resulted in 213 g (purity=99% ee, yield=98%) of tert-butyl ((1R,3R,4R)-4-amino-3-hydroxycyclohexyl)carbamate as a white solid.

(ES, m/z): 231 [M+1]$^+$

1H-NMRδ: 1.211-1.280 (3H, m), 1.447 (9H, s), 1.853-2.082 (5H, m), 2.252-2.299 (1H, m), 2.384-2.464 (1H, m), 3.175-3.257 (1H, m), 3.531 (1H, s), 4.492 (1H, s),

Example 14: Benzyl tert-butyl ((1R,2R,4R)-2-hydroxycyclohexane-1,4-diyl)dicarbamate

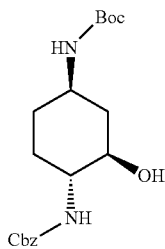 [SMILES: CC(C)(C)OC(=O)N[C@@H]1CC[C@@H](NC(=O)OCc2ccccc2)[C@H](O)C1]

To a solution of tert-butyl ((1R,3R,4R)-4-amino-3-hydroxycyclohexyl)carbamate (213 g, 0.926 mol, 1.00 equiv) in THF (3.5 L) was added Na$_2$CO$_3$ (147 g, 1.39 mol, 1.50 equiv) at 0° C. A solution of benzyl carbonochloridate (236 g, 1.39 mol, 1.50 equiv) in THF (500 mL) was added dropwise to above the solution while maintaining the temperature at 0° C. The resulting solution was stirred for 2 hours at 20° C. The reaction progress was monitored by LCMS until SM was consumed completely. The reaction was quenched by the addition of 15 L ice/water. A lot of white solid was separated out and the solids were collected by filtration. The resulting solid was washed with water (1000*2 ml). The solid was dried in an oven under Vacuum. This resulted in 309 g (purity=98%, yield=91%) of benzyl tert-butyl ((1R,2R,4R)-2-hydroxycyclohexane-1,4-diyl)dicarbamate as a off-white solid.

(ES, m/z): 309 [M-56+1]$^+$

1H-NMR (300 MHz, CDCl$_3$), δ: 1.148-1.343 (4H, m), 1.452 (9H, s), 2.012-2.072 (2H, m), 2.300-2.348 (1H, m), 2.974 (1H, s), 3.434-3.502 (3H, m), 4.504 (1H, s), 4.809 (1H, s), 5.126 (2H, s), 4.27-4.38 (2H, m), 7.361-7.409 (5H, m).

Example 15: (1S,2R,5R)-2-(((benzyloxy)carbonyl)amino)-5-((tert-butoxycarbonyl) amino)cyclohexyl 4-nitrobenzoate

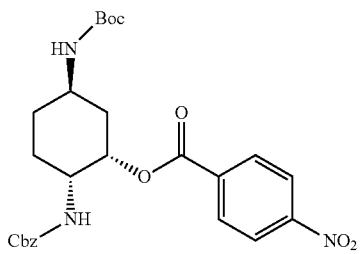 [SMILES: CC(C)(C)OC(=O)N[C@@H]1CC[C@@H](NC(=O)OCc2ccccc2)[C@@H](OC(=O)c2ccc([N+](=O)[O-])cc2)C1]

To a solution of triphenylphosphine (295.8 g, 1.125 mol, 1.50 equiv, 98%) in THF (4000 mL), DEAD (195.7 g, 1.125 mol, 1.50 equiv, 98%) in THF (1500 ml) was added dropwise in 1 hr, while the temperature was maintained at 0-5° C. After the resulting solution was stirred for 10 minutes at 0-5° C., 4-nitrobenzoic acid (125.2 g, 0.750 mol, 1.00 eq, 99%) was added in several portions while maintaining the temperature at 0-5° C. (about 30 minutes added completion). After the resulting solution was stirred for 10 minutes at 0-5° C., benzyl tert-butyl ((1R,2R,4R)-2-hydroxycyclohexane-1,4-diyl)dicarbamate (273 g, 0.750 mol, 1.00 equiv, 98%) was added in several portions while maintaining the temperature at 0-5° C. (about 10 minutes added completion). The resulting solution was allowed to react at 5-20° C. for 3 hrs. The reaction progress was monitored by LCMS until SM was consumed completely. The reaction was quenched by the addition of 2.5 L brine and the organic layer was dried over anhydrous sodium sulfate and concentrated under vacuum. The residue were dissolved in 5 L EA and washed with 2.5 L brine. The organic layer was dried over anhydrous sodium sulfate and concentrated under vacuum again. The crude was purified by re-crystallizing in MeOH (2700 ml). This resulted in 267 g (purity=98%, yield=62%) of (1S,2R,5R)-2-(((benzyloxy)carbonyl)amino)-5-((tert-butoxycarbonyl) amino)cyclohexyl 4-nitrobenzoate as a white solid.

(ES, m/z): 458 [M-56+1]$^+$

1H-NMR (300 MHz, CDCl3), δ: 1.20-1.36 (1H, m), 1.42 (9H, s), 1.52-1.69 (2H, m), 1.75-1.89 (1H, m), 1.97-2.06 (1H, m), 2.15-2.20 (1H, m), 2.39-2.44 (1H, m), 3.81-3.90 (2H, m), 4.42 (1H, s), 4.86-4.88 (1H, d, J=8.4 Hz), 5.04-5.09 (2H, m), 5.53 (1H, s), 7.33 (5H, s), 8.18-8.21 (2H, d, J=9 Hz), 8.29-8.32 (2H, d, J=8. 7 Hz).

Example 16: Benzyl tert-butyl ((1R,2S,4R)-2-hydroxycyclohexane-1,4-diyl)dicarbamate

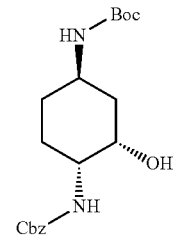

To a solution of (1S,2R,5R)-2-(((benzyloxy)carbonyl)amino)-5-((tert-butoxycarbonyl)amino)cyclohexyl 4-nitrobenzoate (267 g, 0.52 mol, 1.00 equiv, 98%) in MeOH/THF (1700/1700 mL) was added K$_2$CO$_3$ (9.7 g, 70.16 mmol, 4.00 equiv, 98%) in H$_2$O (1000 ml) at 25° C. A The resulting solution was allowed to react for 3.5 h at 25° C. The reaction progress was monitored by LCMS until SM was consumed completely. The resulting solution was diluted with PE/H2O (1400/1600 ml) and product was collected by filtration and was dried in an oven under reduced pressure. This resulted in 172 g (purity=98%, yield=91%) of benzyl tert-butyl ((1R,2S,4R)-2-hydroxycyclohexane-1,4-diyl)dicarbamate as a white solid.

(ES, m/z): 309 [M-56+1]$^+$

1H-NMR: (300 MHz, CDCl$_3$), δ1.161-1.299 (2H, m), 1.299-1.366 (10H, s), 1.792-1.817 (3H, m), 1.993-2.047 (1H, m), 2.142-2.196 (1H, m), 3.618 (1H, s), 3.819 (1H, s), 4.1068 (1H, s), 4.345 (1H, s), 5.109-5.189 (3H, m), 7.305-7.380 (5H, m).

Example 17: tert-butyl ((1R,3S,4R)-4-amino-3-hydroxycyclohexyl)carbamate

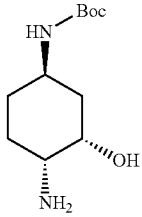 [SMILES: CC(C)(C)OC(=O)N[C@@H]1CC[C@@H](N)[C@@H](O)C1]

To a solution of benzyl tert-butyl ((1R,2S,4R)-2-hydroxy-cyclohexane-1,4-diyl)dicarbamate (170 g, 0.467 mol, 1.00 eq, 98%) in MeOH/THF (1700/1700 ml) was added Pd/C (wet, 34 g). The resulting solution react with an atmosphere of H2 at 25° C. The reaction progress was monitored by LCMS until the starting material was consumed completely (about 4 hours). The filtrate was concentrated under vacuum. The residue was dissolved in 200 ml EA, A lot of white solid was separated out and the solids were collected by filtration. This resulted in 100 g (purity=98%, yield=93%) of tert-butyl ((1R,3S,4R)-4-amino-3-hydroxycyclohexyl)carbamate as a white solid.

(ES, m/z): 231 $[M+1]^+$

1H-NMR: 6:1.271-1.456 (3H, m), 1.509 (9H, S), 1.524-1.593 (2H, m), 1.791 (3H, m), 1.990-2.032 (1H, m), 2.167-2.219 (1H, m), 2.825-2.886 (1H, m), 3.820-3.828 (2H, d, J=2.4 Hz), 4.323 (1H, s).

central linker enantiomer scheme B:

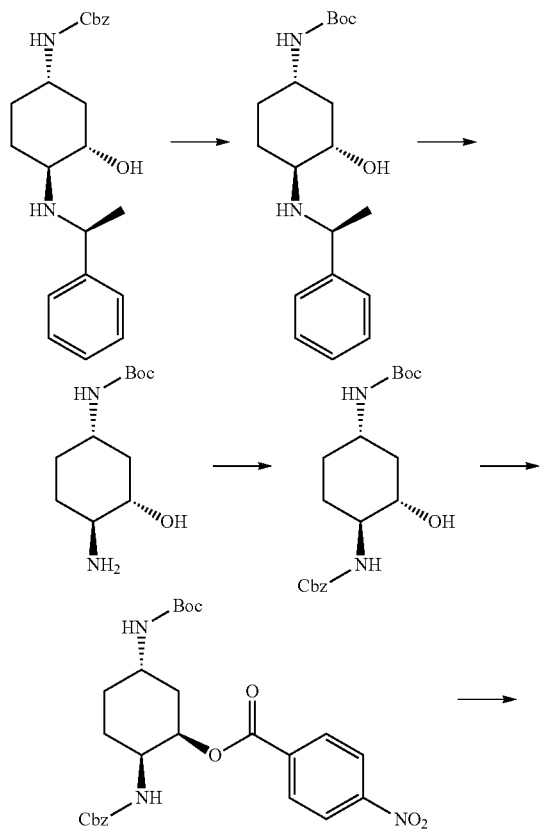

Example 18: benzyl ((1S,3S,4S)-3-hydroxy-4-(((S)-1-phenylethyl)amino)cyclohexyl)carbamate

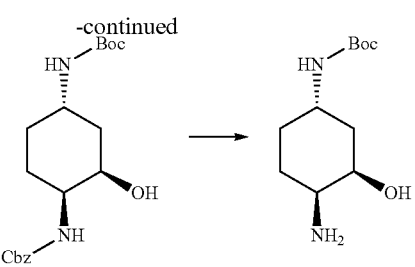

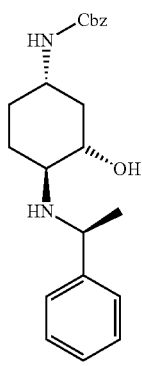

To a solution of benzyl (1R,3R,6S)-7-oxa-bicyclo[4.1.0]heptan-3-ylcarbamate (500 g, 2.02 mol, 1.00 equiv) in ACN (10 L) was added LiClO4 (2146 g, 20.2 mol, 10.00 equiv) and (S)-1-phenylethanamine (269 g, 2.22 mol, 1.10 equiv) at 25° C. The resulting solution was stirred for 18 h at 85° C. The reaction progress was monitored by HLC until the starting material was consumed completely. The resulting solution was diluted with 10000 mL of DCM and then washed with 2×5000 mL of H2O and 1×5000 mL of brine. The organic layer was dried over anhydrous sodium sulfate and concentrated under vacuum. The crude product was purified by re-crystallization in 4000 mL EA. This resulted in 390 g (chemical purity=98%, yield=52%) of PH-GBI-16-50 isomers as a white solid.

Chiral Resolution:

To a solution of PH-GBI-16-50 isomers (390 g, 1.06 mol, 1.00 equiv) in ethanol (4.7 L) was added D-DBTA (387 g, 1.08 mol, 1.00 equiv). The resulting solution was stirred for 30 min at 78° C. and cooled to 0° C. with a water/ice bath. The solids were collected by filtration, and the filtrate was reserved. The solids was added to ethanol (3.1 L), The resulting solution was stirred for 1 hour at 78° C. and cooled to 0° C. with a water/ice bath. The solids were collected by filtration, and the filtrate was reserved. The solid was added to 1 L H2O, Sodium carbonate was employed to adjust the pH to 9-10. The resulting solution was extracted with EtOAc (2*1 L) and the organic layer was dried with Na2SO4 and concentrated under vacuum to give 134 g of PH-GBI-16-50A (optical purity=99% ee, yield=23%) as a colourless syrup.

The above filtrate was concentrated and basified and concentrated with the same method above. This resulted 240 g white solid. The solid was recrystallized in 720 mL MeOH. The filtrate concentrated under vacuum. The product was recrystallized in 450 mL MeOH. This resulted PH-GBI-16-

50B 150 g (purity=94% ee) as a white solid. The product was recrystallized once more in 150 mL MeOH, and to give 85 g of benzyl ((1S,3S,4S)-3-hydroxy-4-(((S)-1-phenylethyl)amino)cyclohexyl)carbamate (purity=99% ee, yield=14%).

(ES, m/z): 369 [M+1]+

1H-NMR: (300 MHz, CDCl3), δ: 0.940-1.267 (4H, m), 1.306-1.366 (3H, d, J=18 Hz), 1.893-2.022 (2H, m), 2.300-2.398 (2H, m), 3.170-3.250 (2H, m), 3.586-3.613 (2H, t, J=8.1 Hz), 3.883-3.948 (1H, m), 4.703 (1H, s), 5.097 (2H, s), 7.242-7.379 (8H, m).

Example 19: tert-butyl ((1S,3S,4S)-3-hydroxy-4-(((S)-1-phenylethyl) amino)cyclohexyl)carbamate

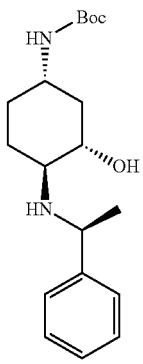

To a solution of benzyl ((1S,3S,4S)-3-hydroxy-4-(((S)-1-phenylethyl)amino)cyclohexyl)carbamate (250 g, 0.679 mol, 1.00 equiv) in methanol (3750 mL), Boc2O (148 g, 0679 mol, 1.00 equiv) and Palladium carbon (wet) (25 g) were added. Then the hydrogen gas was then bubbled into the mixture. The resulting solution was stirred for 4.5 hours at 15 degree C. The reaction progress was monitored by LCMS until the starting material was consumed completely. The solids were filtered out. The filtrate was concentrated under vacuum. The residue was dissolved in 500 ml EA, A lot of white solid was separated out and the solids were collected by filtration. This resulted in 205 g (purity=99% ee, yield=90%) of tert-butyl ((1S,3S,4S)-3-hydroxy-4-(((S)-1-phenylethyl)amino)cyclohexyl)carbamate as a white solid.

(ES, m/z): 335 [M+1]+

1H-NMR: δ: 1.111-1.273 (4H, m), 1.337-1.359 (3H, d, J=6.6 Hz), 1.463 (9H, s), 1.889-2.010 (2H, m), 2.289-2.369 (2H, m), 3.148-3.230 (1H, m), 3.498 (2H, s), 3.881-3.945 (1H, m), 4.446 (1H, s), 7.233-7.343 (5H, m).

Example 20: tert-butyl ((1S,3S,4S)-4-amino-3-hydroxycyclohexyl)carbamate

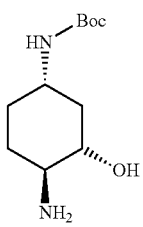

To a solution of tert-butyl ((1S,3S,4S)-3-hydroxy-4-(((S)-1-phenylethyl)amino)cyclohexyl)carbamate (203 g, 0.608 mol, 1.00 equiv) in methanol (3000 mL), Pd(OH)2 (wet, 120 g) was added carefully under N2. Then the hydrogen gas was then bubbled into the mixture. The resulting solution was stirred for 12 h at 30 degree C. The reaction progress was monitored by LCMS until the starting material was consumed completely. The solids were filtered out and the filtrate was concentrated under vacuum. This resulted in 117 g (purity=99% ee, yield=84%) of tert-butyl ((1S,3S,4S)-4-amino-3-hydroxycyclohexyl)carbamate as a off-white solid.

(ES, m/z): 231 [M+1]+

1H-NMR: δ: 1.202-1.262 (3H, m), 1.449 (9H, s), 1.855-2.005 (5H, m), 2.256-2.380 (1H, m), 2.394-2.460 (1H, m), 3.174-3.255 (1H, m), 3.535 (1H, s), 4.481 (1H, s),

Example 21: Benzyl tert-butyl ((1S,2S,4S)-2-hydroxycyclohexane-1,4-diyl)dicarbamate

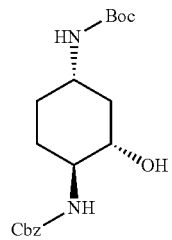 [SMILES: CC(C)(C)OC(=O)N[C@H]1CC[C@H](NC(=O)OCc2ccccc2)[C@@H](O)C1]

To a solution of tert-butyl ((1S,3S,4S)-4-amino-3-hydroxycyclohexyl)carbamate (117 g, 0.507 mol, 1.00 equiv, 99%) in THF (1.5 L) was added Na2CO3 (80.5 g, 0.759 mol, 1.50 equiv, 98%) at 0° C. A solution of benzyl carbonochloridate (12.9 g, 0.759 mol, 1.50 eq, 98%) in THF (500 mL) was added dropwise to above the solution while maintaining the temperature at 0° C. The resulting solution was stirred for 3 hours at 25° C. The reaction progress was monitored by LCMS until SM was consumed completely. The reaction was quenched by the addition of 10 L ice/water, a lot of white solid was separated out and the solids were collected by filtration. The resulting solid was washed with water (500*2 ml). The solid was dried in an oven under Vacuum. This resulted in 162 g (purity=98%, yield=87%) of benzyl tert-butyl ((1S,2S,4S)-2-hydroxycyclohexane-1,4-diyl)dicarbamate as an off-white solid.

(ES, m/z): 309 [M-56+1]+

1H-NMR: δ: 1.184-1.352 (4H, m), 1.447 (9H, s), 2.005-2.045 (2H, m), 2.287-2.334 (1H, m), 3.431-3.496 (3H, m), 4.537-4.582 (1H, s), 4.920 (1H, s), 5.119-5.166 (2H, m), 7.280-7.396 (5H, m).

Example 22: (1R,2S,5S)-2-(((benzyloxy)carbonyl)amino)-5-((tert-butoxycarbonyl)amino)cyclohexyl 4-nitrobenzoate

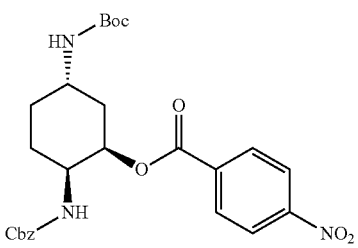 [SMILES: CC(C)(C)OC(=O)N[C@H]1CC[C@H](NC(=O)OCc2ccccc2)[C@H](OC(=O)c2ccc([N+](=O)[O-])cc2)C1]

To a solution of triphenylphosphine (181 g, 0.688 mol, 1.50 equiv, 98%) in THF (2700 mL), DEAD (174 g, 0.689 mol, 1.50 equiv, 98%) in THF (600 ml) was added dropwise in 0.5 hr, while the temperature was maintained at 0-5° C. After the resulting solution was stirred for 20 minutes at 0-5° C., 4-nitrobenzoic acid (76.6 g, 0.458 mol, 1.00 eq, 99%) was added in several portions while maintaining the temperature at 0-5° C. (about 30 minutes added completion). After the resulting solution was stirred for 20 minutes at 0-5° C., benzyl tert-butyl ((1S,2S,4S)-2-hydroxycyclohexane-1,4-diyl)dicarbamate (162 g, 0.445 mol, 1.00 equiv, 98%) was added. The resulting solution was allowed to react at 5-20° C. for 2.5 hrs. The reaction progress was monitored by LCMS. The reaction was quenched by the addition of 1.5 L brine and the organic layer was dried over anhydrous sodium sulfate and concentrated under vacuum. The residue were dissolved in 2 L EA and washed with 1 L brine. The organic layer was dried over anhydrous sodium sulfate and concentrated under vacuum again. The crude was purified by re-crystallizing in MeOH (1500 ml). This resulted in 150 g (purity=96%, yield=65.7%) of (1R,2S,5S)-2-(((benzyloxy)carbonyl)amino)-5-((tert-butoxycarbonyl)amino)cyclohexyl 4-nitrobenzoate as a white solid.

(ES, m/z): 458 [M-56+1]+

1H-NMR: (300 MHz, CDCl₃), δ: 1.27 (1H, s), 1.42 (9H, s), 1.52-1.64 (1H, m), 1.81-1.86 (1H, m), 1.89-2.00 (1H, m), 2.17-2.21 (1H, d, J=12 Hz), 2.39-2.44 (2H, d, J=15 Hz), 3.80-3.89 (2H, m), 4.43 (1H, s), 4.87-4.90 (1H, d, J=9 Hz), 5.04-5.13 (2H, m), 5.53 (1H, s), 7.33 (5H, s), 8.17-8.22 (2H, m), 8.29-8.32 (2H, d, J=9 Hz).

Example 23: benzyl tert-butyl ((1S,2R,4S)-2-hydroxycyclohexane-1,4-diyl)dicarbamate

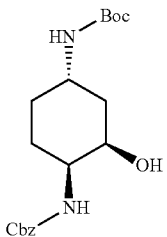 [SMILES: CC(C)(C)OC(=O)N[C@H]1CC[C@H](NC(=O)OCc2ccccc2)[C@H](O)C1]

To a solution of (1R,2S,5S)-2-(((benzyloxy)carbonyl)amino)-5-((tert-butoxycarbonyl)amino)cyclohexyl 4-nitrobenzoate (150 g, 0.292 mol, 1.00 equiv, 96%) in MeOH/THF (750/750 mL) was added K₂CO₃ (161 g, 1.169 mol, 4.00 equiv, 98%) in H2O (600 ml) at 25° C. The resulting solution was allowed to react for 2 h at 25° C. The reaction progress was monitored by LCMS until SM was consumed completely. The resulting solution was diluted with PE/H2O (750/900 ml) and product was collected by filtration and was dried in an oven under reduced pressure. This resulted in 102 g (purity=98%, yield=96%) of benzyl tert-butyl ((1S,2R,4S)-2-hydroxycyclohexane-1,4-diyl)dicarbamate as a white solid (ES, m/z): 309 [M-56+1]+

1H-NMR: δ1.218-1.365 (2H, m) 1.444 (10H, s), 1.706-1.789 (3H, m), 1.974-2.037 (1H, m), 2.136-2.180 (1H, m), 3.591-3.619 (1H, m), 3.849 (1H, s), 4.100 (1H, s), 4.369 (1H, s), 5.103 (1H, s), 5.239 (1H, s), 7.280-7.401 (5H, m).

Example 24: tert-butyl ((1S,3R,4S)-4-amino-3-hydroxycyclohexyl)carbamate

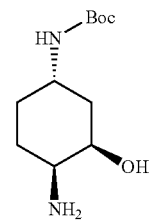

Reactants

| Substance | Formula | MW | Amt | Units | Eq | mol | Purity (%) |
|---|---|---|---|---|---|---|---|
| PH-GBI-17-12B | C19H28N2O5 | 364 | 100 | G | 1.00 | 0.275 | 98% |
| Pd/C(wet) | N/A | N/A | 10 | G | N/A | N/A | N/A |
| MeOH/THF | N/A | N/A | 1/1 | L | N/A | N/A | N/A |

To a solution of tert-butyl ((1S,3R,4S)-4-amino-3-hydroxycyclohexyl)carbamate (100 g, 0.275 mol, 1.00 eq, 98%) in MeOH/THF (1000/1000 ml) was added Pd/C (wet, 10 g). The resulting solution react with an atmosphere of H₂ at 25° C. The reaction progress was monitored by LCMS until the starting material was consumed completely (about 3 hours). The filtrate was concentrated under vacuum. The residue was dissolved in 200 ml EA, A lot of white solid was separated out and the solids were collected by filtration. This resulted in 59 g (purity=98%, yield=93%) of tert-butyl ((1S,3R,4S)-4-amino-3-hydroxycyclohexyl)carbamate as a white solid.

(ES, m/z): 231 [M+1]+

1H-NMR: δ: 1.05-1.35 (3H, m), 1.509 (9H, S), 1.522-1.715 (3H, m), 1.976-2.038 (1H, m), 2.152-2.231 (1H, m), 2.815-2.877 (1H, m), 3.818-3.827 (2H, d, J=2.7 Hz), 4.333 (1H, s).

Synthesis scheme C

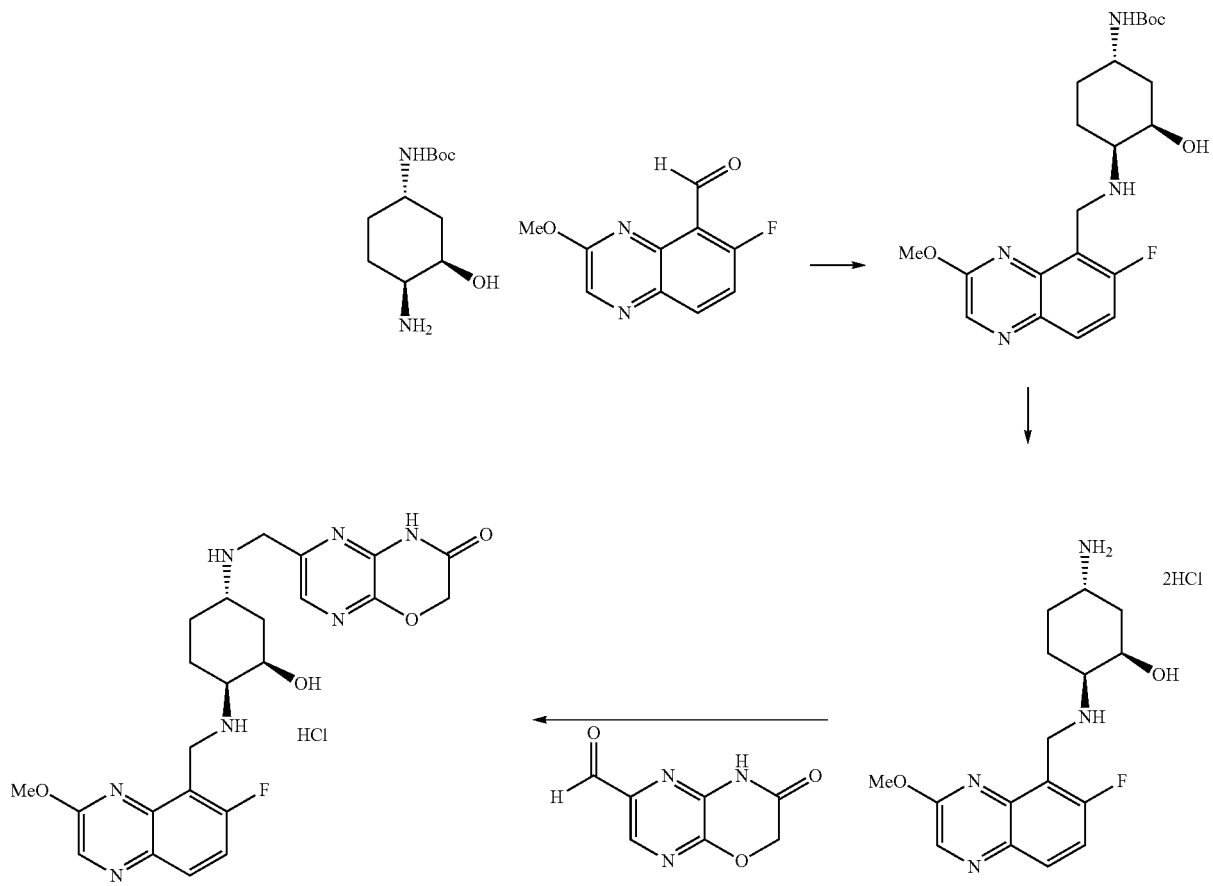

Example 25 tert-Butyl (1S,3R,4S)-4-((7-fluoro-3-methoxyquinoxalin-8-yl)methylamino)-3-hydroxy-cyclohexylcarbamate

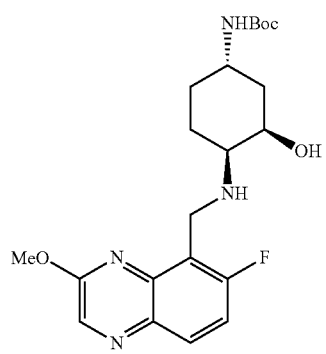 [SMILES: COc1cnc2ccc(F)c(CN[C@H]3CC[C@H](NC(=O)OC(C)(C)C)C[C@H]3O)c2n1]

tert-Butyl-(1R,3S,4R)-4-amino-3-hydroxycyclohexylcarbamate (77 g, 0.33 mol, 1 eq.) was dissolved in chloroform (3.9 L) and methanol (540 ml) and placed under a nitrogen atmosphere. 6-Fluoro-3-methoxyquinoxaline-5-carbaldehyde (62.0 g, 0.30 mol, 0.9 eq.) was charged to the reaction which was stirred at room temperature over night. Sodium triacetoxyborohydride (141.6 g, 0.67 mol, 2 eq.) was added portion wise to the reaction over 20 minutes (exotherm from 12.6-18.2° C.). The reaction was then stirred at room temperature for 2 h. Reaction complete by TLC and LC (AM620A) and was quenched by the addition of sat. aq. NaHCO$_3$ solution (5.75 L). The layers were separated and the aqueous layer was extracted with 10% MeOH:DCM (2 L). The organics were dried over MgSO$_4$, filtered and concentrated in vacuo giving a yellow solid (AM620B, 190 g). The crude product was purified by chromatography: silica=8 Kg packed in dichloromethane and eluted with 1% MeOH:DCM (20 L), 2% MeOH:DCM (20 L), 4% MeOH:DCM (20 L), 5% MeOH:DCM (40 L), 7.5% MeOH:DCM (30 L), 10% MeOH:DCM (30 L). The product containing fractions were combined and concentrated in vacuo providing 135.5 g of tert-Butyl (1S,3R,4S)-4-((7-fluoro-3-methoxyquinoxalin-8-yl)methylamino)-3-hydroxycyclohexylcarbamate (active=129.8 g, yield=100%) with a purity by LC of 99.4%.

$^1$H NMR (CDCl$_3$, 270 MHz): δ, 0.92-1.28 (3H, m), 1.29-1.47 (11H, m), 1.48-1.70 (1H, m), 1.79-2.02 (1H, m), 2.06-2.26 (1H, m), 2.37-2.55 (1H, m), 3.41 (2H, s), 3.67 (1H, br s), 4.06 (3H, s), 4.13 (1H, br s), 4.21-4.28 (2H, m), 4.33 (1H, br s), 7.28 (1H, t, J=8.9 Hz), 7.90 (1H, dd, J=5.7 and 8.9 Hz) and 8.40 (1H, s).

Example 26: (1R,2S,5S)-2-((7-Fluoro-2-methoxy-quinoxalin-8-yl)methylamino)-5-aminocyclohexanol.2HCl

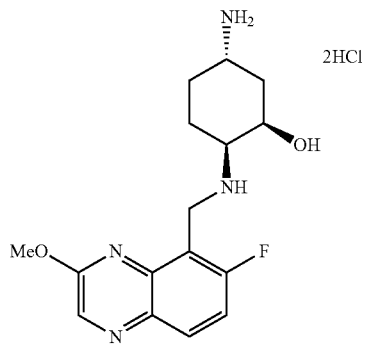 [SMILES: COc1cnc2ccc(F)c(CN[C@H]3CC[C@H](N)C[C@H]3O)c2n1]

tert-Butyl (1S,3R,4S)-4-((7-fluoro-3-methoxyquinoxalin-8-yl)methylamino)-3-hydroxycyclohexylcarbamate (129.8 g, 0.30 mol, 1 eq.) was dissolved in dichloromethane (1.5 L) and methanol (1.5 L) and placed under a nitrogen atmosphere. 4M HCl in 1,4-dioxane (1.16 L, 4.63 mol, 15 eq.) was added slowly to the reaction over 30 minutes (keeping the reaction temperature below 25° C.). The reaction was then stirred at room temperature over night (after stirring for 15 minutes a white solid had precipitated out of solution). The following morning the reaction was complete by TLC and LC (AM622A) and was concentrated in vacuo giving 128.9 g of (1R,2S,5S)-2-((7-Fluoro-2-methoxyquinoxalin-8-yl)methylamino)-5-aminocyclohexanol.2HCl (active=116.01 g, yield=95.5%) an off-white solid with a purity of 90% by $^1$H nmr assay.

$^1$H NMR (D$_2$O, 270 MHz): δ, 1.40-1.60 (1H, m), 1.62-1.76 (1H, m), 1.77-1.96 (1H, m), 2.04-2.18 (2H, m), 2.19-2.34 (1H, m), 3.26 (1H, s), 3.39-3.58 (2H, m), 4.05 (3H, s), 4.52 (1H, s), 4.61-4.74 (2H, m), 7.43 (1H, t, J=9.2 Hz), 7.96 (1H, dd, J=5.9 and 9.2 Hz) and 8.36 (1H, s).

Example 27: 6-(((1S,3R,4S)-4-((7-Fluoro-2-methoxyquinoxalin-8-yl)methylamino)-3-hydroxy-cyclohexylamino)methyl)-2H-pyrazino[2,3-b][1,4]oxazin-3(4H)-one Hydrochloride

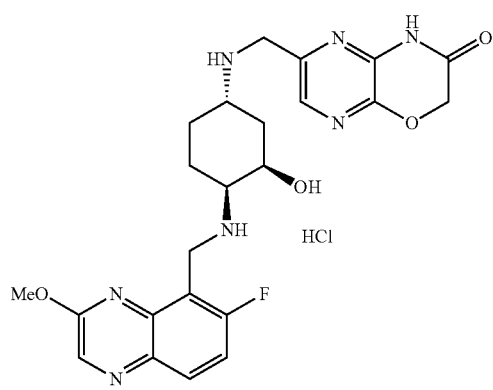 [SMILES: COc1cnc2ccc(F)c(CN[C@H]3CC[C@H](NCc4cnc5c(n4)NC(=O)CO5)C[C@H]3O)c2n1 ; Cl]

(1R,2S,5S)-2-((7-Fluoro-2-methoxyquinoxalin-8-yl)methylamino)-5-aminocyclohexanol.2HCl (115.2 g, 293 mol, 1 eq.) was suspended in chloroform (5.95 L) and isopropanol (825 ml). Triethyl amine (123 ml, 879 mol, 3 eq.) was charged to the reaction which was placed under a nitrogen atmosphere. 3,4-Dihydro-3-oxo-2H-pyrazino[2,3-b][1,4]oxazine-6-carbaldehyde (47.2 g, 263.7 mol, 0.9 eq.) was charged to the reaction which was stirred at room temperature overnight (in morning a solution had formed). Sodium triacetoxyborohydride (186.3 g, 879 mol, 3 eq.) was charged to the reaction over 20 minutes. The reaction was then stirred at room temperature for 2.5 h and sampled (AM625A), only 1.4% aldehyde remaining. The reaction was quenched by the addition of sat. aq. NaHCO$_3$(10 L). The solution was stirred for 20 minutes and then the layers were separated. The aqueous layer was extracted with 20% MeOH:DCM (5×3 L) and the organics were dried over MgSO$_4$, filtered and concentrated in vacuo. The crude product was absorbed on to 300 g of silica before purification by chromatography: silica=10 Kg, packed in DCM and eluted with 10% MeOH:DCM (180 L), 0.5% NH$_4$OH: 8% MeOH:DCM (60 L), 0.5% NH$_4$OH: 10% MeOH:DCM. The product containing fractions were concentrated in vacuo giving 109.6 g of 6-(((1S,3R,4S)-4-((7-Fluoro-2-methoxy-quinoxalin-8-yl)methylamino)-3-hydroxycyclohexylamino)methyl)-2H-pyrazino[2,3-b][1,4]oxazin-3(4H)-one (AM625B, yield=86.0%) with a purity of 98.6% by LCMS.

6-(((1S,3R,4S)-4-((7-Fluoro-2-methoxyquinoxalin-8-yl)methylamino)-3-hydroxycyclohexylamino)methyl)-2H-pyrazino[2,3-b][1,4]oxazin-3(4H)-one (1 g) was suspended in dichloromethane (36 ml), methanol (20 ml) and ethanol (20 ml) and placed under a nitrogen atmosphere. 2M HCl in Et$_2$O (1 ml) was added to the suspension and after a few minutes a solution was obtained. The reaction was concentrated in vacuo giving 970 mg of an off-white solid (AM625C) with a purity by LCMS of 98.7% and the largest impurity at a level of 0.37%. The Cl content of the mono HCl salt was 8.25% (theoretical Cl content=6.82%). Due to the Cl content of the mono HCl salt being high the free base was tested and found to contain 1.4% Cl. A portion of the free base (5 g, AM625B) was dissolved in 10% MeOH:DCM (100 ml) and a suspension was obtained. A further 50 ml of 20% MeOH:DCM was added to the suspension and the solid still did not fully dissolve. A solution of sat. aq. K$_2$CO$_3$ (20 ml) was added to the suspension and a solution was obtained. The layers were separated and the organics dried over MgSO$_4$, filtered and concentrated in vacuo providing 4.22 g of a white solid (AM625D) with a purity by LCMS of 98.5% and a Cl content of 0%. The remaining AM625B (103.4 g) was taken-up in 10% MeOH:DCM (2 L) and 20% MeOH:DCM (1 L) and washed with sat. aq. K$_2$CO$_3$ solution (400 ml). The layers were separated and the organics were dried over MgSO$_4$, filtered and concentrated in vacuo giving 95.1 g (AM625E) of a white solid with a purity of 98.5% by LCMS (1 impurity at a level of 0.46%). The aqueous layer was extracted with 10% MeOH:DCM (2×1 L) and the organics were dried over MgSO$_4$, filtered and concentrated in vacuo giving 2.3 g (AM625F) of a white solid.

AM625E (1 g) was suspended in dichloromethane (36 ml), methanol (20 ml) and ethanol (20 ml) and placed under a nitrogen atmosphere. 2M HCl in Et$_2$O (1 ml) was added to the suspension and after a few minutes a solution was obtained. The reaction was concentrated in vacuo giving 1.08 g of an off-white solid (AM625G) with a Cl content of 7.7% and a purity of 98.6%.

AM625E (1 g) was suspended in dichloromethane (36 ml), methanol (20 ml) and ethanol (20 ml) and placed under a nitrogen atmosphere. 2M HCl in Et$_2$O (0.95 ml) was added to the suspension and after a few minutes a solution was obtained. The reaction was concentrated in vacuo giving 1.08 g of an off-white solid (AM625H) with a Cl content of 6.9% and a purity of 98.5%.

The remaining freebase was taken-up in dichloromethane (3.47 L), methanol (1.93 L) and ethanol (1.93 L) and placed under a nitrogen atmosphere. 2M HCl in Et$_2$O (91.6 ml) was added to the suspension and after a few minutes a solution was obtained. The reaction was concentrated in vacuo giving a white solid (100.5 g, AM625I) which was dried in the oven over night providing 96.0 g (AM625J) with a purity of 98.6% by LCMS and one impurity at a level of 0.59%.

AM625J (5 g) was suspended in ethanol (100 ml) and heated to reflux. The ethanol was increased in 10 volume increments until 50 volumes had been added. The reaction was still a suspension and it was cooled to room tempera- 50° C. producing 86.5 g of 6-(((1S,3R,4S)-4-((7-Fluoro-2-methoxyquinoxalin-8-yl)methylamino)-3-hydroxycyclohexylamino)methyl)-2H-pyrazino[2,3-b][1,4]oxazin-3(4H)-one hydrochloride as a white solid (AM625P) with a purity of 99.1% (impurity=0.41%) by LCMS. Cl content=6.84% (theoretical Cl content=6.82%) and solvents by GC: EtOH=2901 ppm, MeOH=425 ppm, Et$_2$O=4 ppm and DCM=642 ppm.

$^1$H NMR (DMSO, 270 MHz): δ, 1.13-1.70 (3H, m), 1.72-1.94 (1H, m), 1.94-2.31 (2H, m), 2.73-3.11 (2H, m), 3.19-3.57 (1H, m), 3.89 (2H, br s), 4.01-4.27 (4H, m), 4.37 (2H, br s), 4.78-5.24 (3H, m), 7.57 (1H, t, J=9.2 Hz), 7.91 (1H, s), 8.05 (1H, dd, J=5.9 and 9.2 Hz) and 8.62 (1H, s).

MS (ES$^+$) m/z 484.5 (MH$^+$).

Synthesis Scheme D:

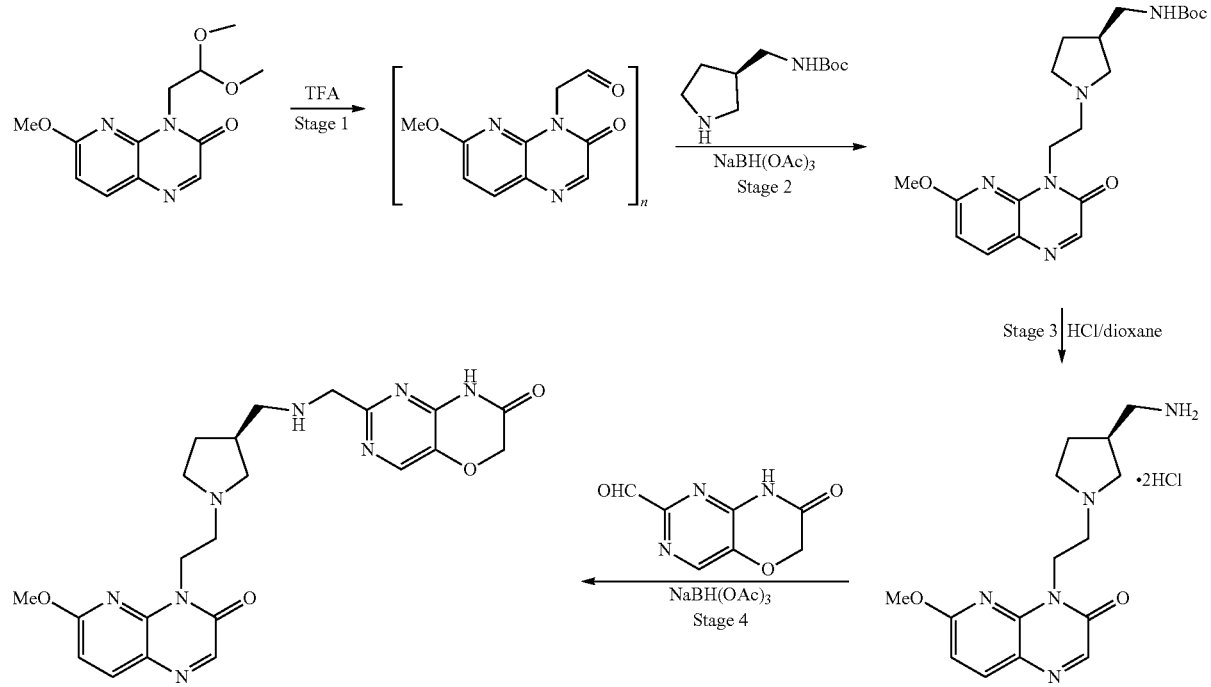

ture. The suspension was filtered and providing 3.25 g of a white solid (AM625K) with a purity of 99.4% and the impurity had been reduced to a level of 0.18%. To increase the recovery two further trial were attempted using AM625J (2×2.5 g) and 20 volumes and 30 volumes of ethanol. The suspensions were heated at reflux for 1 h before cooling to room temperature and filtering. The filter cake was washed with ethanol (30 ml) giving a white solid: AM625 L (20 volumes)=2.43 g LCMS=99.1% impurity=0.41% and AM625M (30 volumes)=2.41 g LCMS=99.1% impurity=0.37%.

The remaining AM625J (85.2 g) was charged to a flask followed by ethanol (2.5 L) and placed under a nitrogen atmosphere. The suspension was heated to reflux and stirred for 1 h before cooling to room temperature. The suspension was filtered and the filter cake was washed with ethanol (300 ml). The filter cake (AM625N) was dried in the oven over night at 45° C. giving 90 g (AM625O) of a white solid which contained 5.5% ethanol by $^1$H nmr. Due to the high ethanol content AM625O was dried in the oven for a further 5 h at Stage 1: 2-(6-Methoxy-3-oxopyrido[3,2-b]pyrazin-4(3H)-yl)acetaldehyde

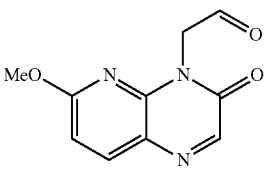 [SMILES: COc1ccc2ncc(=O)n(CC=O)c2n1]

The 6-methoxy-4-(2,2-dimethoxyethyl)pyrido[3,2-b]pyrazin-3(4H)-one (80 g) was stirred in a 1 L flange flask. TFA/water 50:50 (500 ml) was slowly added and the reaction stirred for 2 hours. LC analysis showed no starting material remained. The TFA was removed in vacuo. The residue was partitioned between DCM (800 ml) and saturated NaHCO$_3$ (800 ml). The aqueous phase was further extracted with DCM (2×400 ml). The combined organic layer was dried over Na$_2$SO$_4$, filtered and the solvent evaporated off. The crude material was azeotroped with toluene (2×400 ml) to remove the last of the TFA leaving a purple green solid, 64.6 g, 98% yield and a purity by $^1$H NMR of >95%, trace toluene present.

$^1$H NMR (CDCl$_3$, 270 MHz): δ 3.90 (3H, s), 5.19 (2H, s), 6.73 (1H, d, J=8.6 Hz), 8.04 (1H, d, J=8.6 Hz), 8.20 (1H, s) and 9.7 (1H, s).

Stage 2: tert-butyl ((S)-1-(2-(6-Methoxy-3-oxopyrido[3,2-b]pyrazin-4(3H)-yl)ethyl)pyrrolidin-3-yl)methylcarbamate

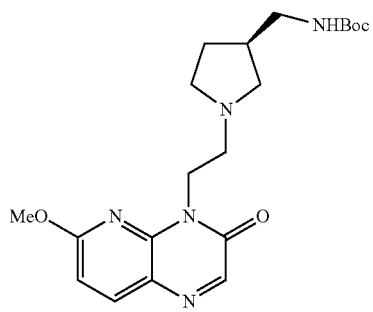 [SMILES: COc1ccc2ncc(=O)n(CCN3CC[C@@H](CNC(=O)OC(C)(C)C)C3)c2n1]

The 6-methoxy-4-(2,2-dimethoxyethyl)pyrido[3,2-b]pyrazin-3(4H)-one (44 g) and tert-butyl ((R)-pyrrolidin-3-yl)methylcarbamate (40 g) were stirred in chloroform (640 ml)/MeOH (160 ml) overnight at room temperature under N$_2$. The NaBH(OAc)$_3$ was added in portions so that the temperature of the reaction did not rise above 30° C. The reaction was stirred at room temperature for 2 h. TLC analysis showed no starting materials remained (Solvent system: 10% MeOH:90% DCM). The reaction was carefully quenched with a saturated solution of NaHCO$_3$ (800 ml). The aqueous and organic phases were partitioned and the aqueous extracted with DCM (2×500 ml). The combined organic phases were washed with water (1 L) and brine (1 L) before drying over MgSO$_4$, filtering and evaporating. The crude material was combined with crude material from a previous reaction, dissolved in DCM and loaded onto a silica column (2.5 Kg). The product was eluted with 0-1% methanol/DCM. No pure product was isolated therefore the material was re-columned (silica 2.5 Kg) eluting with 100% EtOAc then 3% and 5% MeOH once the impurities had come off. The product containing fractions were evaporated to provide 86 g of product (17% EtOAc present) by $^1$H NMR>95% purity and 96% purity by LCMS.

$^1$H NMR (CDCl$_3$, 270 MHz): δ 1.42-1.47 (10H, m), 1.81-2.00 (1H, m), 2.20-2.45 (1H, m), 2.45-2.81 (5H, m), 2.81-3.20 (3H, m), 4.01 (3H, s), 4.41-4.68 (2H, m), 4.83-5.02 (1H, m), 6.71 (1H, d, J=8.6 Hz), 7.99 (1H, d, J=8.6 Hz) and 8.13 (1H, s).

Stage 3: 4-(2-((S)-3-(aminomethyl)pyrrolidin-1-yl)ethyl)-6-methoxypyrido[3,2-b]pyrazin-3(4H)-one Dihydrochloride

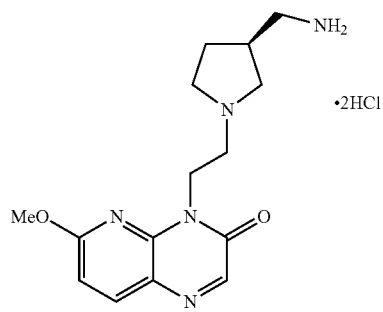 [SMILES: COc1ccc2ncc(=O)n(CCN3CC[C@@H](CN)C3)c2n1]

To a solution of tert-butyl ((S)-1-(2-(6-Methoxy-3-oxopyrido[3,2-b]pyrazin-4(3H)-yl)ethyl)pyrrolidin-3-yl)methylcarbamate (35 g) in DCM (500 ml)/MeOH (500 ml) at room temperature under N$_2$ was added 4M HCl in dioxane (300 ml) dropwise at a rate that the temperature does not exceed 25° C. The reaction mixture was stirred at room temperature and after 4 h LC analysis indicated the reaction was complete. The reaction mixture was concentrated in vacuo to provide 4-(2-((S)-3-(aminomethyl)pyrrolidin-1-yl)ethyl)-6-methoxypyrido[3,2-b]pyrazin-3(4H)-one dihydrochloride, 25 g, 77% yield. $^1$H NMR (DMSO) corresponded to the desired product. $^1$H NMR assay using maleic acid as the internal standard indicated a purity of 100%.

$^1$H NMR (DMSO, 270 MHz): δ 1.60-2.39 (2H, m), 2.56-3.44 (6H, m), 3.44-3.91 (4H, m), 3.91-4.14 (5H, m), 4.52-4.76 (2H, m), 6.86 (1H, d, J=8.4 Hz), 8.12-8.16 (2H, m), 8.23-8.49 (3H, m) and 11.46-11.62 (1H, m).

Example 28: 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one

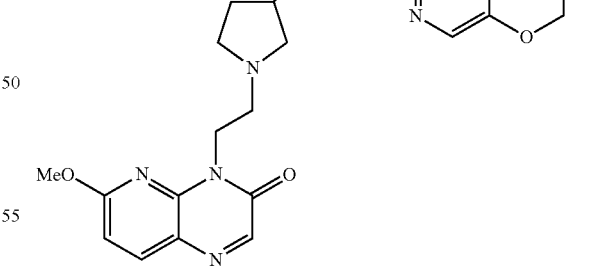

4-(2-((S)-3-(aminomethyl)pyrrolidin-1-yl)ethyl)-6-methoxypyrido[3,2-b]pyrazin-3(4H)-one dihydrochloride, 80% active (1.25 g, 1 g active, 2.67 mmol, 1 equiv.), 7,8-dihydro-7-oxo-6H-pyrimido[5,4-b][1,4]oxazine-2-carbaldehyde 85% active (0.51 g, 0.43 g active, 2.4 mmol, 0.9 equiv.), triethylamine (1.1 ml, 8.01 mmol, 3 equiv.) were taken up in CHCl$_3$ (50 ml), IPA (7 ml). The reaction mixture was stirred overnight followed by the portionwise addition of NaBH(OAc)$_3$ (1.13 g, 5.34 mmol, 2 equiv.). The reaction mixture was stirred for 2 h, LCMS analysis indicated the reaction was complete. The reaction mixture was diluted with CHCl₃ (50 ml) and washed with sat. aq. NaHCO₃ (75 ml). The aqueous was extracted with CHCl₃ (2×100 ml). The combined organics were washed with water (150 ml), brine (100 ml), dried over MgSO₄ and concentrated in vacuo to provide crude product. The crude product was combined with crude material isolated from the subsequent reactions for purification as described below.

Example 29: 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one

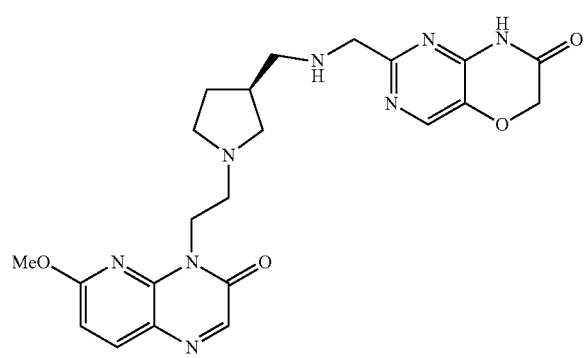 [SMILES: COc1ccc2ncc(=O)n(CCN3CC[C@@H](CNCc4ncc5c(n4)NC(=O)CO5)C3)c2n1]

4-(2-((S)-3-(aminomethyl)pyrrolidin-1-yl)ethyl)-6-methoxypyrido[3,2-b]pyrazin-3(4H)-one dihydrochloride, 80% active (5 g, 4 g active, 10.7 mmol, 1 equiv.), 7,8-dihydro-7-oxo-6H-pyrimido[5,4-b][1,4]oxazine-2-carbaldehyde 85% active (2 g, 1.7 g active, 9.63 mmol, 0.9 equiv.), triethylamine (4.4 ml, 32.1 mmol, 3 equiv.) were taken up in CHCl₃ (200 ml), IPA (28 ml). The reaction mixture was stirred overnight followed by the portionwise addition of NaBH(OAc)₃ (4.5 g, 21.4 mmol, 2 equiv.). The reaction mixture was stirred for 2 h, LCMS analysis indicated the reaction was complete. The reaction mixture was diluted with CHCl₃ (200 ml) and washed with sat. aq. NaHCO₃ (300 ml). The aqueous was extracted with CHCl₃ (2×400 ml). The combined organics were washed with water (600 ml), brine (400 ml), dried over MgSO₄ and concentrated in vacuo to provide crude product. The crude product was combined with crude material isolated from the subsequent reactions for purification as described below.

Example 30: 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one

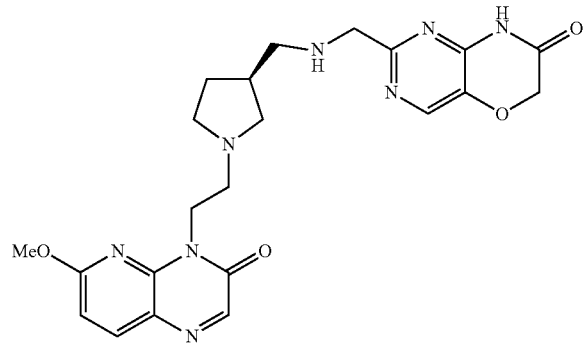 [SMILES: COc1ccc2ncc(=O)n(CCN3CC[C@@H](CNCc4ncc5c(n4)NC(=O)CO5)C3)c2n1]

4-(2-((S)-3-(aminomethyl)pyrrolidin-1-yl)ethyl)-6-methoxypyrido[3,2-b]pyrazin-3(4H)-one dihydrochloride, 90% active (1.11 g, 1 g active, 2.67 mmol, 1 equiv.), 7,8-dihydro-7-oxo-6H-pyrimido[5,4-b][1,4]oxazine-2-carbaldehyde 85% active (0.51 g, 0.43 g active, 2.4 mmol, 0.9 equiv.), triethylamine (1.1 ml, 8.01 mmol, 3 equiv.) were taken up in CHCl₃ (50 ml), IPA (7 ml). The reaction mixture was stirred overnight followed by the portionwise addition of NaBH(OAc)₃ (1.13 g, 5.34 mmol, 2 equiv.). The reaction mixture was stirred for 2 h, LCMS analysis indicated the reaction was complete. The reaction mixture was diluted with CHCl₃ (50 ml) and washed with sat. aq. NaHCO₃ (75 ml). The aqueous was extracted with CHCl₃ (2×100 ml). The combined organics were washed with water (150 ml), brine (100 ml), dried over MgSO₄ and concentrated in vacuo to provide crude product. The crude product was combined with crude material isolated from the subsequent reactions for purification as described below.

Example 31: 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one

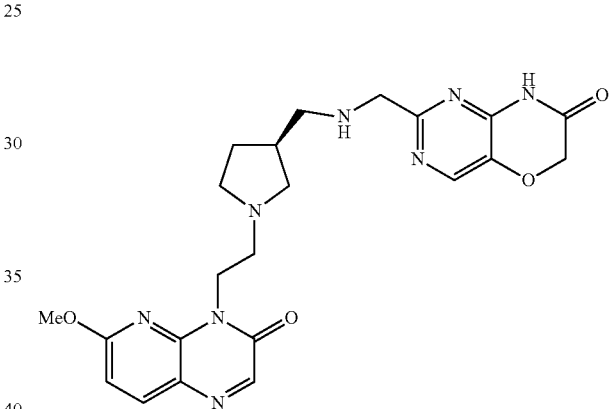

4-(2-((S)-3-(aminomethyl)pyrrolidin-1-yl)ethyl)-6-methoxypyrido[3,2-b]pyrazin-3(4H)-one dihydrochloride, 85% active (23 g, 19.5 g active, 0.052 mol, 1 equiv.), 7,8-dihydro-7-oxo-6H-pyrimido[5,4-b][1,4]oxazine-2-carbaldehyde 85% active (9.9 g, 8.4 g active, 0.0468 mol, 0.9 equiv.), triethylamine (21.8 ml, 0.156 mol, 3 equiv.) were taken up in CHCl₃ (1.2 L), IPA (170 ml). The reaction mixture was stirred overnight followed by the portionwise addition of NaBH(OAc)₃ (22 g, 0.104 mol, 2 equiv.). The reaction mixture was stirred for 2 h, LCMS analysis indicated the reaction was complete. The reaction mixture was diluted with CHCl₃ (1.2 L) and washed with sat. aq. NaHCO₃ (1.5 L). The aqueous was extracted with CHCl₃ (2×1 L). The combined organics were washed with water (3 L), brine (2 L), dried over MgSO₄ and concentrated in vacuo to provide crude product. The crude product was combined with crude material isolated from the subsequent reactions for purification as described below.

Purification of crude 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one (Batches 1-4)

Batch 1 (1.5 g), batch 2 (5.8 g), batch 3 (1.2 g) and batch 4 (25 g) were taken up in DCM and loaded onto a silica column (2 Kg) packed with DCM. The column was run using DCM:IPA:NH₄OH 70:29:1. Fractions 32-55 contained the product and were concentrated in vacuo to provide 2-({[((3S)-1-{2-[6-(Methyloxy)-3-oxopyrido[2,3-b]pyrazin-4(3H)-yl]ethyl}-3-pyrrolidinyl)methyl]amino}methyl)-1H-pyrimido[5,4-b][1,4]oxazin-7(6H)-one, 20.3 g, 71% yield. ¹H NMR (CDCl₃) corresponded to the desired product with ~4% IPA present. LCMS indicated a purity of 98.1% with no single impurity >0.4%.

¹H NMR (CDCl₃, 270 MHz): δ 1.36-1.60 (1H, m), 1.86-2.13 (1H, m) 2.32-3.09 (9H, m), 3.90 (2H, s), 4.49-4.67 (4H, m), 4.49-4.67 (4H, m), 6.68 (1H, d, J=8.6 Hz), 7.96 (1H, d, J=8.6 Hz), 8.12 (1H, s) and 8.15 (1H, s).

MS (ES⁺) m/z 467 (MH⁺).

To starting material (73.8 g)+H₂O (516 ml) add TFA dropwise (516 ml) over 1H at T<20° C. (slight exotherm). Stir 2-3 h at rt. TLC:hept:EtOAc 1:1—no SM. Carefully added reaction to sat. NaHCO₃soln (5 L) [pH~7]. Extracted with Et₂O (2 L)+EtOAc (2×2 L). Organic layers washed sta. NaHCO₃(1 L)+brine (500 ml). Dried, filtered+concentrated—34 g. Back extracted aqueous with EtOAc (3×1 L). Organic dried, filtered+concentrated—21 g. Total 55 g, yield=90.3%.

¹H NMR (CDCl₃, 270 MHz): δ, 3.91 (3H, s), 5.22 (2H, s), 6.64 (2H, d, J=8.9 Hz), 7.65 (1H, d, J=9.5 Hz), 7.77 (1H, d, J=8.4 Hz) and 9.65 (1H, s).

Synthesis Scheme E

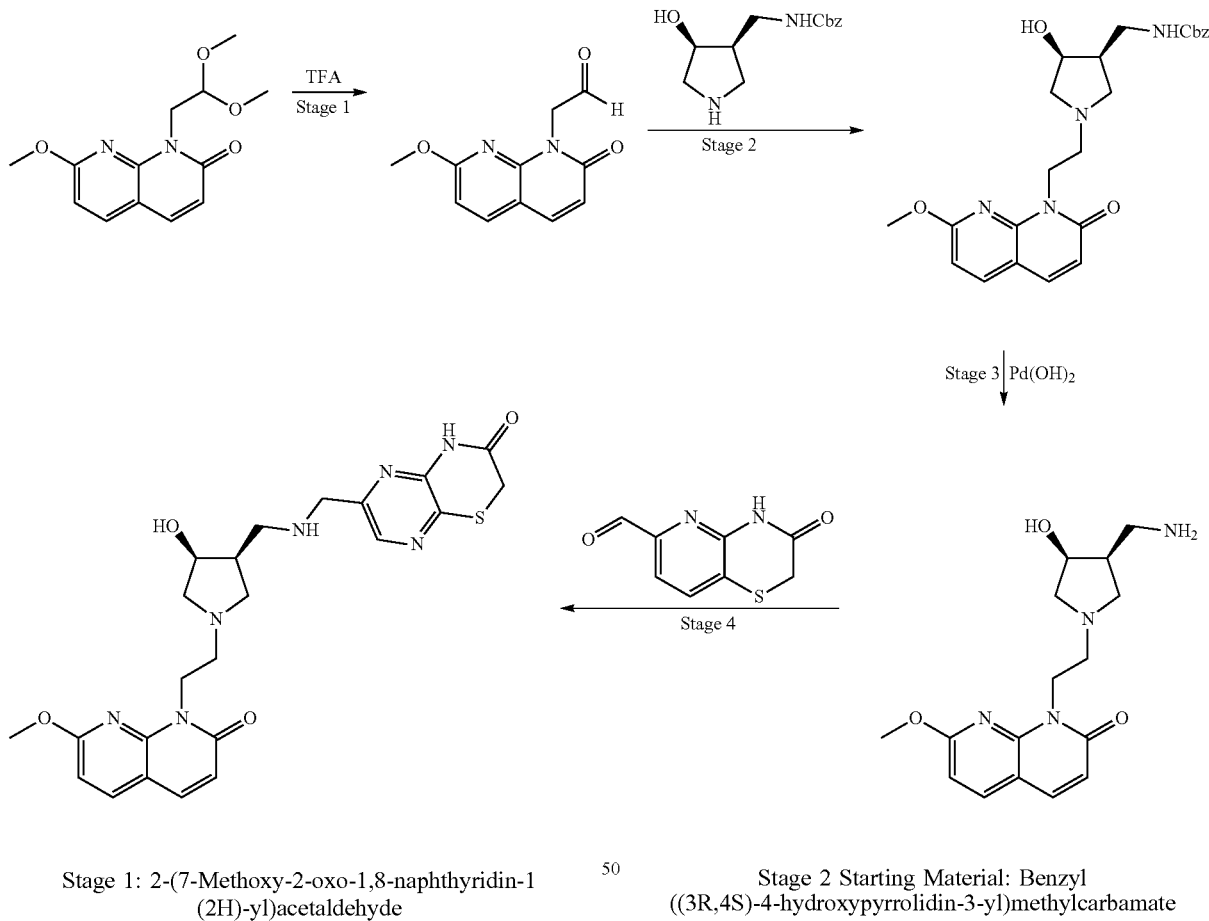

Stage 1: 2-(7-Methoxy-2-oxo-1,8-naphthyridin-1(2H)-yl)acetaldehyde

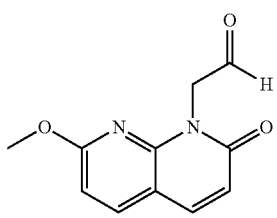 [SMILES: COc1ccc2ccc(=O)n(CC=O)c2n1]

Stage 2 Starting Material: Benzyl ((3R,4S)-4-hydroxypyrrolidin-3-yl)methylcarbamate

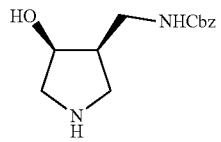

To N-Boc SM (60 g) in DCM (800 ml)+MeOH (800 ml) add 4M HCl/dioxane (800 ml) over 0.5 h at T 20-25° C. (Slight exotherm). Stir 3 h at RT. Concentrated reaction in vacuo to give 49.0 g white solid. Yield=100%

¹H NMR (DMSO, 270 MHz): δ, 2.07-2.40 (1H, m), 2.73-3.00 (1H, m), 3.00-3.45 (5H, m), 4.15-4.35 (1H, m), 5.02 (2H, s), 5.40-5.54 (1H, m), 7.21-7.54 (5H, m), and 9.09-9.63 (2H, m).

Stage 2: Benzyl N-{[(3S,4S)-4-hydroxy-1-[2-(7-methoxy-2-oxo-1,2-dihydro-1,8-naphthyridin-1-yl)ethyl]pyrrolidin-3-yl]methyl}carbamate

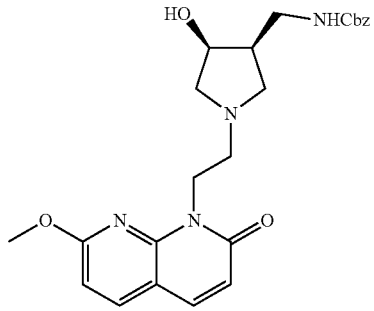 [SMILES: COc1ccc2ccc(=O)n(CCN3C[C@H](CNC(=O)OCc4ccccc4)[C@H](O)C3)c2n1]

To a 2 L flask was charged pyrrolidine.HCl (52.6 g), 'aldehyde' (40 g), DCM (800 ml)+MeOH (160 ml). Added NEt₃ (18.5 g) dropwise over 20 mins at T 20-25° C. (slight exotherm) to give a yellow solution (pH>7). Add NaBH(OAc)₃ (116.9 g) [T=25° C.]+stir 4 h at rt. Mini work-up: NMR: not complete. Reaction left stirring overnight. Mini work-up+TLC is complete. Added sat. NaHCO₃ solution (700 ml) (pH>7). Separated organic layer. Extracted Aq with 10% MeOH/DCM (250 ml). Organic dried (Na₂SO₄), filtered+concentrated—70 g yellow oil. Concentrated onto silica (150 g). Purified by column chromatography (1 Kg) EtOAc 100%–20% MeOH/EtOAc. Product fractions—22.4 g (Batch 1). Column flush (MeOH)—13 g (Batch 2) and top spot fractions—9.5 g (Batch 3). The silica from the column was slurried in DCM/MeOH 10% (3 L), filtered and concentrated in vacuo to provide (13 g). Analysis indicated no product present. Batch 1 (22.4 g) and Batch 2 (13 g) were re-columned. Mass of silica 2.5 Kg. Solvent system: 20% MeOH/EtOAc. The product containing fractions were concentrated in vacuo to provide—25 g. ¹H NMR (CDCl₃) corresponded to the desired product in ~90% purity with 30% EtOAc present—active amount 17.5 g, 21% yield.

¹H NMR (CDCl₃, 270 MHz): δ, 2.16-2.53 (1H, m), 2.60-3.12 (6H, m), 3.13-3.57 (3H, m), 4.01 (3H, s), 4.19-4.32 (2H, m), 4.52-4.74 (2H, m), 5.08 (2H, br s), 5.27-5.52 (1H, m), 6.55 (1H, d, J=9.2 Hz), 6.61 (1H, d, J=8.6 Hz), 7.28 (1H, s), 7.27-7.38 (5H, m), 7.53 (1H, d, J=9.5 Hz), and 7.70 (1H, d, J=8.4 Hz).

Stage 3: 1-(2-((3S,4S)-3-(Aminomethyl)-4-hydroxy-pyrrolidin-1-yl)ethyl)-7-methoxy-1,8-naphthyridin-2(1H)-one

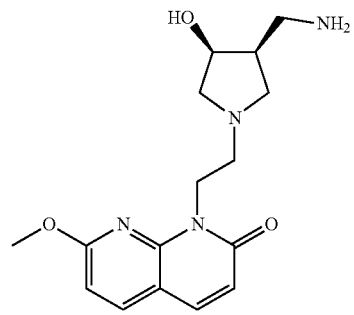 [SMILES: COc1ccc2ccc(=O)n(CCN3C[C@H](CN)[C@H](O)C3)c2n1]

Pd(OH)₂ (2 g) was added to a flask with MeOH (20 ml). 1-(2-((3S,4S)-3-(Aminomethyl)-4-hydroxypyrrolidin-1-yl)ethyl)-7-methoxy-1,8-naphthyridin-2(1H)-one benzyl carbamate (17.7 g, 39.1 mmol, 1 equiv.) dissolved in MeOH (180 ml) was added to the flask. The reaction mixture was stirred with H2 bubbling through the mixture. LC analysis after 2 h indicated trace formation of the product. A further charge of Pd(OH)₂ (2 g) from a different batch was added and the reaction continued with H₂ bubbling through for a further 2 h. LC analysis indicated complete consumption of the starting material. The reaction mixture was filtered through celite and the filter pad washed with MeOH (1 L). The filtrate was concentrated in vacuo to provide a viscous oil, 14.5 g, 116% yield. LCMS analysis indicated a purity of 73%. The material was combined with the crude product from a smaller scale reaction (7.3 g) and purified by column chromatography. Mass of silica: 1 Kg. Solvent system: 1% NH₄OH, 29% MeOH, 70% DCM increasing to 1% NH₄OH, 39% MeOH, 70% DCM. Detection: UV/ninhydrin. The product containing fractions were concentrated in vacuo to provide 15.1 g. LCMS analysis indicated a purity of 88%. ¹H NMR (MeOD) corresponded to the desired product. ¹H NMR assay using maleic acid as the internal standard indicated an activity of 73%—active amount=11 g.

¹H NMR (MeOD, 270 MHz): δ, 2.09-2.40 (1H, m), 2.40-3.10 (7H, m), 3.10-3.25 (1H, m), 4.04 (3H, d, J=3.0 Hz), 4.24-4.46 (1H, m), 4.52-4.72 (2H, m), 5.48 (2H, d, J=3.0 Hz), 6.52 (1H, dd, J=9.4 and 3.0 Hz), 6.69 (1H, dd, J=8.6 and 3.0 Hz), 7.80 (1H, dd, J=9.7 and 3.0 Hz) and 7.92 (1H, dd, J=8.6 and 3.0 Hz).

MS (ES⁺) m/z 318.9 (MH⁺).

Example 32

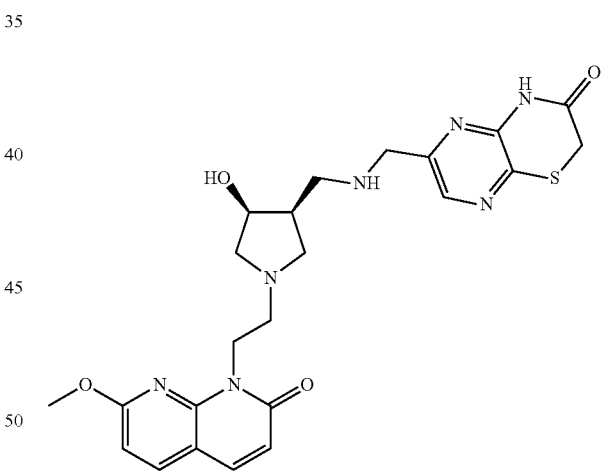

1-(2-((3S,4S)-3-(Aminomethyl)-4-hydroxypyrrolidin-1-yl)ethyl)-7-methoxy-1,8-naphthyridin-2(1H)-one 73% active (13.7 g, 10 g active, 31.4 mmol, 1 equiv.), 3,4 dihydro-3-oxo-2H-pyrazino[2,3-b][1,4]thiazine-6-carbaldehyde 74% active (7.45 g, 5.5 g active, 28.26 mmol, 0.9 equiv.) were taken up in CHCl₃ (500 ml) and IPA (70 ml). The reaction mixture was stirred overnight followed by the portionwise addition of NaBH(OAc)₃ (16.6 g, 78.5 mmol, 2.5 equiv.). The reaction mixture was stirred for 3 h after which point LCMS analysis indicated the reaction was complete. The reaction mixture was quenched with sat. aq. NaHCO₃ (600 ml). The aqueous phase was extracted with 10% MeOH/DCM (2×1 L). The combined organics were washed with water (1 L), brine (1 L), dried over MgSO₄ and combined with the material from the small-scale reaction. The combined material was concentrated in vacuo to provide a crude solid, 18.8 g. The material was purified by column chromatography. Mass of silica: 750 g. Solvent system: 1% NH₄OH, 9% MeOH, 90% DCM. Detection: UV. The product fractions were concentrated in three batches. Batch 1, Fractions 18-22—7.9 g. LC purity—91.6%, largest single impurity 2.8%. Batch 2, Fractions 17—1.9 g, LC purity—77.6%, largest single impurity 8.8%. Batch 3 Fr 23-1.3 g, LC purity—83.8%, largest single impurity 3.5%. A repeat column was carried out with the following modifications incorporated: alternative solvent system 1% NH₄OH, 15% IPA, 84% DCM A blend of 50% fine grade silica and 50% normal silica (100 equiv) was used.

The product containing fractions were concentrated to provide 5 batches as shown below:

Fractions 34-35—0.4 g, 68%, largest single impurity 15.8%.

Fractions 36-38—1.7 g, LCMS—91% largest single impurity 4.0%

Fractions 39-43—2.8 g, LCMS—94.5% impurities >0.5%: 2.5% MW 697, 0.7% MW 511 (M+14 imp).

Fractions 44-57—3.5 g, LCMS 95.3% impurities >0.5%: 1.9% MW 697, 0.7% MW 511 (M+14 imp).

Fractions 58-63—0.8 g, LCMS 96.0% impurities >0.5%: 1.0% MW 697.

Initial small-scale recrystallisations were attempted on batch fractions 44-57 using the following solvents:

MeCN—dissolves hot but oils out on cooling

MeOH/Et₂O—dissolves hot but oils out on cooling

Remaining batches were taken up in DCM (250 ml) combined and concentrated in vacuo to provide 7.4 g as the free base, LCMS indicated a purity of 93.3% with three impurities at a level of >0.5%, 1.0%, 2.0% and 0.6%. A portion of the material was taken up in DCM (10 ml) and converted to the mono HCl salt by adding 1M HCl in Et₂O (0.94 ml) and concentrating in vacuo to provide 521 mg. LCMS purity 94.4%.

$^1$H NMR (CDCl₃, 270 MHz): δ, 2.29-2.51 (1H, m), 2.51-3.03 (8H, m), 3.64 (2H, s), 3.67-3.88 (2H, m), 4.01 (3H, s), 4.32-4.52 (1H, m), 4.55-4.78 (2H, m), 6.55-6.62 (2H, m), 7.54 (1H, d, J=9.7 Hz), 7.70 (1H, d, J=8.6 Hz) and 8.00 (1H, s).

MS (ES⁺) m/z 497.8 (MH⁺).

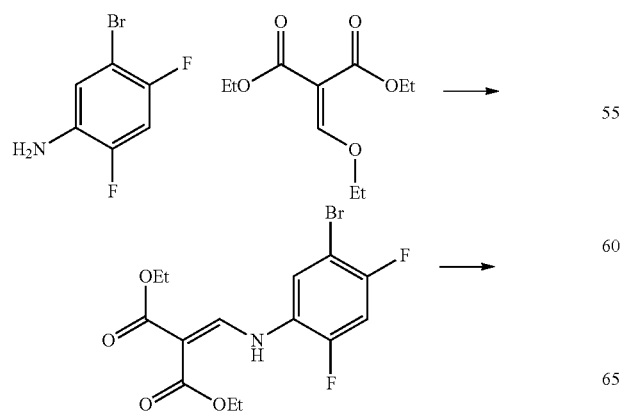

Synthesis Scheme F

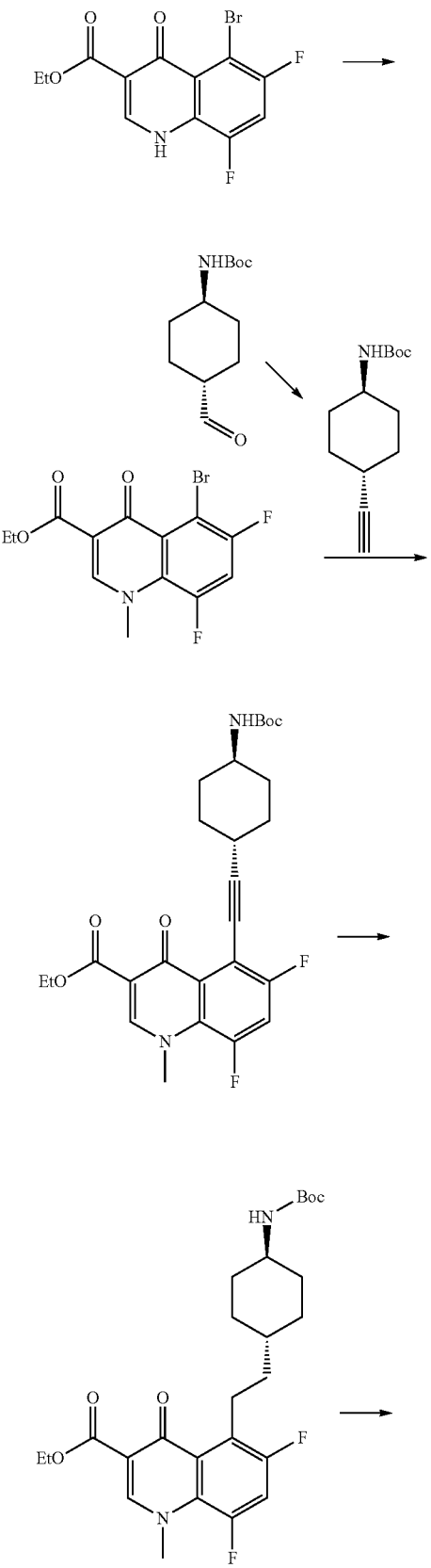

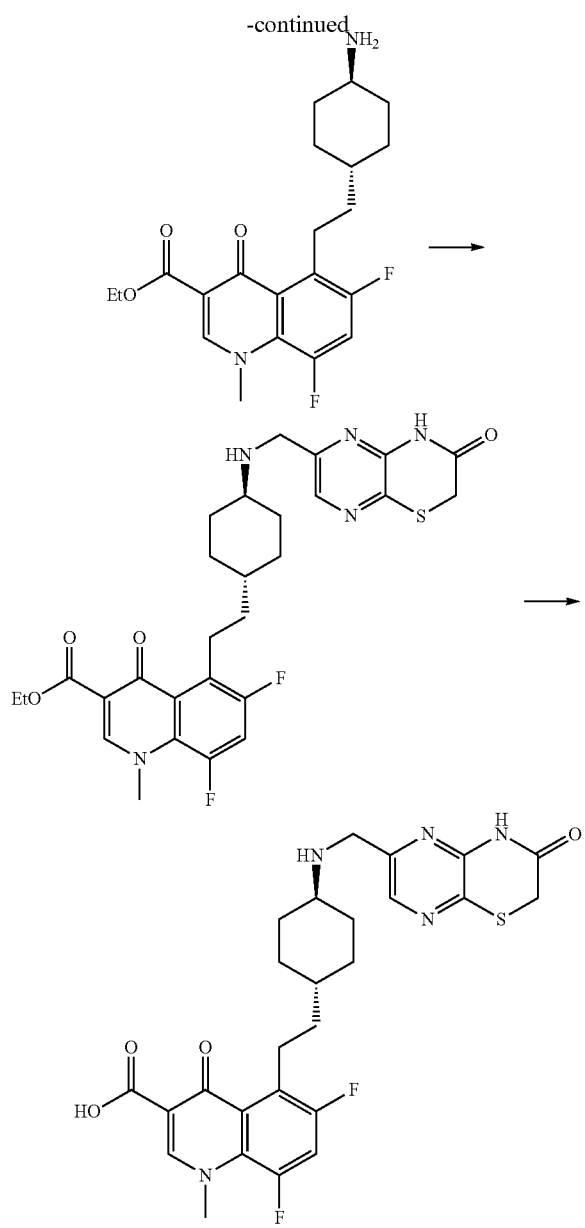

Example 33 a) Diethyl 2-(((5-bromo-2,4-difluorophenyl)amino)methylene)malonate

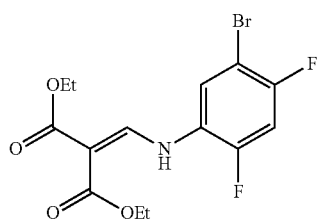 [SMILES: CCOC(=O)C(=CNc1cc(Br)c(F)cc1F)C(=O)OCC]

To a solution of (5-bromo-2,4-difluorophenyl)amine (20 g, 96 mmol) in i-PrOH (192 mL) was added diethyl [(eth- yloxy)methylidene]propanedioate (19.27 mL, 96 mmol) at room temperature. The resulting solution was heated to 80° C. overnight. The resulting homogeneous solution was cooled to room temperature and then placed in an ice bath, at which point the product began to precipitate out as a white cottony solid. Hexane was added, and the mixture was stirred for 10 min to break up the clumps. The precipitate was collected by filtration through a Buchner funnel to afford diethyl 2-(((5-bromo-2,4-difluorophenyl)amino) methylene)malonate (29 g, 77 mmol, 80% yield) as a white cottony solid. LCMS: m/z 378.1 (M+), 380.1 (M+2+). $^1$H NMR (DMSO-$d_6$) ☐: 10.82 (d, J=11.9 Hz, 1H), 8.45 (d, J=12.4 Hz, 1H), 8.16 (dd, J=8.3, 7.3 Hz, 1H), 7.70 (dd, J=11.1, 8.6 Hz, 1H), 4.22 (q, J=6.8 Hz, 2H), 4.15 (q, J=7.0 Hz, 2H), 1.26 (t, 6H)

b) ethyl 5-bromo-6,8-difluoro-4-oxo-1,4-dihydro-quinoline-3-carboxylate

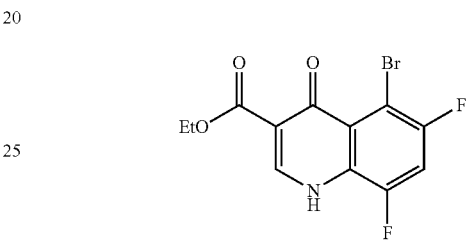

Diphenyl ether (135 mL) was heated to a boil in a flask placed directly in a heating mantle. Diethyl 2-(((5-bromo-2,4-difluorophenyl)amino)methylene)malonate (5.00 g, 13.2 mmol) was added portionwise, and the resulting solution was heated for 2 h. The mixture was cooled to ambient temperature and diluted with hexanes. The precipitate was collected by filtration through a Buchner funnel to afford ethyl 5-bromo-6,8-difluoro-4-oxo-1,4-dihydro-3-quinolinecarboxylate (3.42 g, 10.3 mmol, 78% yield) as a beige solid.

LCMS: m/z 332.0 (M+), 334.0 (M+2+). $^1$H NMR (DMSO-$d_6$) ☐: 12.47 (br. s., 1H), 8.30 (br. s., 1H), 8.02 (dd, J=10.6, 8.8 Hz, 11H), 4.22 (q, J=7.1 Hz, 2H), 1.28 (t, J=7.1 Hz, 3H).

c) ethyl 5-bromo-6,8-difluoro-1-methyl-4-oxo-1,4-dihydroquinoline-3-carboxylate

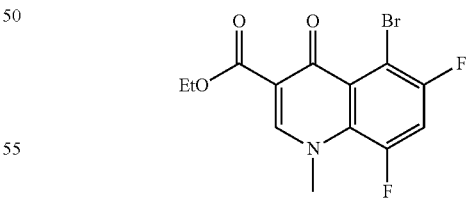

To a solution of ethyl 5-bromo-6,8-difluoro-4-oxo-1,4-dihydro-3-quinolinecarboxylate (3.42 g, 10.3 mmol) in DMF (101 mL) was added potassium carbonate (4.27 g, 30.9 mmol) and methyl iodide (1.93 mL, 30.9 mmol). The reaction mixture was heated at 100° C. for 3 h and then filtered after cooling to room temperature. The filtrate was concentrated under vacuum and the residue was diluted with ethyl acetate and washed with water two times. The aqueous layers were combined and extracted with ethyl acetate. The organic layers were combined and dried over Na₂SO₄, filtered, and then concentrated to afford ethyl 6,8-difluoro-5-formyl-1-methyl-4-oxo-1,4-dihydroquinoline-3-carboxylate (3.46 g, 10.0 mmol, 97% yield). LCMS: m/z 346.1 (M⁺), 348.1 (M+2⁺). ¹H NMR (DMSO-d₆) □: 8.52 (s, 1H), 8.01 (dd, J=14.0, 8.7 Hz, 1H), 4.23 (q, J=7.2 Hz, 2H), 4.04 (d, J=10.1 Hz, 3H), 1.29 (t, 3H).

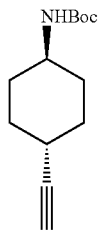 [SMILES: C#C[C@H]1CC[C@H](NC(=O)OC(C)(C)C)CC1]

d) tert-butyl ((1r,4r)-4-ethynylcyclohexyl)carbamate

To a solution of tert-butyl ((1r,4r)-4-formylcyclohexyl)carbamate (909 mg, 4.00 mmol) in MeOH (10 mL) was added potassium carbonate (1.11 g, 8.00 mmol), followed by a solution of dimethyl (1-diazo-2-oxopropyl)phosphonate (845 mg, 4.40 mmol) in MeOH (10 mL) at 0° C. The mixture was warmed to room temperature and stirred overnight. Then, the mixture was filtered, and the filtrate was concentrated. The resulting residue was dissolved in ethyl acetate (50 mL), and the solution was washed with brine three times. The organic layer was dried with sodium sulfate, filtered and concentrated to afford tert-butyl ((1r,4r)-4-ethynylcyclohexyl)carbamate (843 mg, 94% yield) as white solid. ¹H NMR (400 MHz, DMSO-d₆) δ: 1.01-1.20 (m, 2H), 1.23-1.34 (m, 2H), 1.36 (s, 9H), 1.68-1.79 (m, 2H), 1.81-1.93 (m, 2H), 2.07-2.23 (m, 1H), 2.84 (d, J=2.27 Hz, 1H), 3.08-3.27 (m, 1H), 6.74 (d, J=7.83 Hz, 1H).

e) ethyl 5-(((1r,4r)-4-((tert-butoxycarbonyl)amino)cyclohexyl)ethynyl)-6,8-difluoro-1-methyl-4-oxo-1,4-dihydroquinoline-3-carboxylate

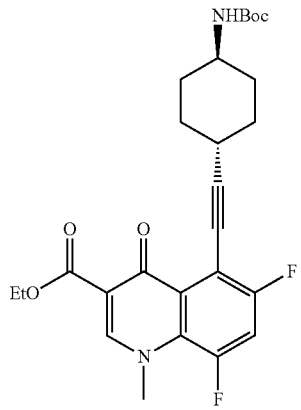 [SMILES: CCOC(=O)c1cn(C)c2c(F)cc(F)c(C#C[C@H]3CC[C@H](NC(=O)OC(C)(C)C)CC3)c2c1=O]

To a mixture of ethyl 5-bromo-6,8-difluoro-1-methyl-4-oxo-1,4-dihydroquinoline-3-carboxylate (800 mg, 2.31 mmol), tert-butyl ((1r,4r)-4-ethynylcyclohexyl)carbamate (516 mg, 2.31 mmol), cesium carbonate (904 mg, 2.77 mmol), and tri-t-butylphosphine tetrafluoroboric acid salt (53.6 mg, 0.185 mmol) was added DMF (9.10 mL) followed by bis(triphenylphosphine)palladium(II) chloride (65 mg, 0.092 mmol) and DBU (0.070 mL, 0.46 mmol). The flask was placed under an atmosphere of N₂ and heated in the microwave at 150° C. for 13 min. The mixture was filtered and rinsed with plenty of DCM and ethyl acetate. The filtrate was concentrated, and the resulting residue was purified using silica gel chromatography (0-100% EA/Hex, 35 min, 80 g column) to afford ethyl 5-(((1r,4r)-4-((tert-butoxycarbonyl)amino)cyclohexyl)ethynyl)-6,8-difluoro-1-methyl-4-oxo-1,4-dihydroquinoline-3-carboxylate (755 mg, 1.14 mmol, 50% yield). LCMS: m/z 489.3 (MH⁺).

f) ethyl 5-(2-((1r,4s)-4-((tert-butoxycarbonyl)amino)cyclohexyl)ethyl)-6,8-difluoro-1-methyl-4-oxo-1,4-dihydroquinoline-3-carboxylate

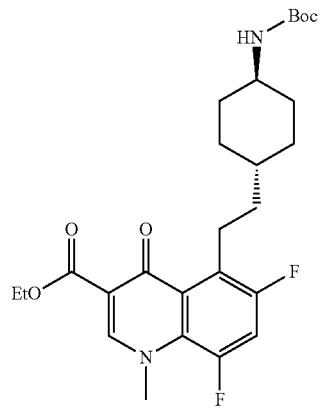 [SMILES: CCOC(=O)c1cn(C)c2c(F)cc(F)c(CC[C@H]3CC[C@H](NC(=O)OC(C)(C)C)CC3)c2c1=O]

To a solution of ethyl 5-(((1r,4r)-4-((tert-butoxycarbonyl)amino)cyclohexyl)ethynyl)-6,8-difluoro-1-methyl-4-oxo-1,4-dihydroquinoline-3-carboxylate (400 mg, 0.614 mmol) in EtOH (8.19 mL) was added several spatula tips of wet Raney Ni. The mixture was placed under an atmosphere of H₂ (30 psi) overnight. The resulting mixture was filtered through celite and rinsed with EtOH and MeOH. The filtrate was concentrated onto silica gel and purified by silica gel chromatography eluting with 0-100% EA/Hex to afford ethyl 5-(2-((1r,4s)-4-((tert-butoxycarbonyl)amino)cyclohexyl)ethyl)-6,8-difluoro-1-methyl-4-oxo-1,4-dihydroquinoline-3-carboxylate (205 mg, 0.416 mmol, 68% yield) as an off white solid.

LCMS: m/z 493.4 (MH⁺).

g) ethyl 5-(2-((1r,4s)-4-aminocyclohexyl)ethyl)-6,8-difluoro-1-methyl-4-oxo-1,4-dihydroquinoline-3-carboxylate

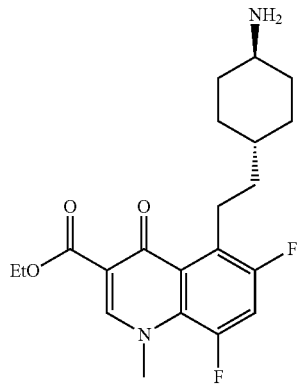 [SMILES: CCOC(=O)c1cn(C)c2c(F)cc(F)c(CC[C@H]3CC[C@H](N)CC3)c2c1=O]

To a solution of ethyl 5-(2-((1r,4s)-4-((tert-butoxycarbonyl) amino)cyclohexyl)ethyl)-6,8-difluoro-1-methyl-4-oxo-1,4-dihydroquinoline-3-carboxylate (200 mg, 0.406 mmol) in DCM (2.00 mL) and EtOH (2.00 mL) was added 4 M HCl in dioxane (2.0 mL, 8.0 mmol). The reaction mixture was stirred for 2 h, and then the volatiles were removed in vacuo. This material was used in the next step without purification. LCMS: m/z 393.3 (MH+).

h) ethyl 6,8-difluoro-1-methyl-4-oxo-5-(2-((1r,4s)-4-(((3-oxo-3,4-dihydro-2H-pyrazino[2,3-b][1,4]thiazin-6-yl)methyl)amino)cyclohexyl)ethyl)-1,4-dihydroquinoline-3-carboxylate

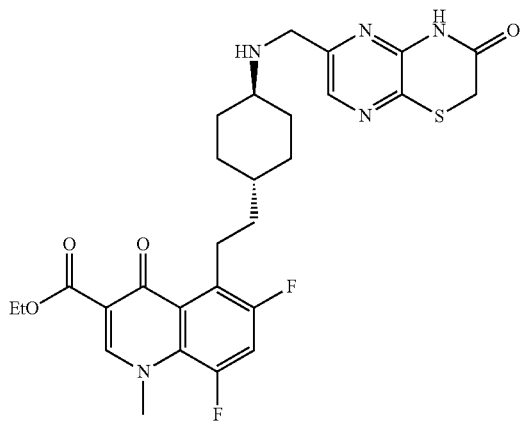 [SMILES: Cn1cc(C(=O)O)c(=O)c2c(CC[C@H]3CC[C@H](NCc4cnc5c(n4)NC(=O)CS5)CC3)c(F)cc(F)c21]

To a solution of ethyl 5-(2-((1r,4s)-4-aminocyclohexyl)ethyl)-6,8-difluoro-1-methyl-4-oxo-1,4-dihydroquinoline-3-carboxylate (174 mg, 0.406 mmol) and 3-oxo-3,4-dihydro-2H-pyrazino[2,3-b][1,4]thiazine-6-carbaldehyde (79 mg, 0.41 mmol) in DCM (2.00 mL) and EtOH (2.00 mL) was added triethylamine (0.113 mL, 0.811 mmol). The mixture was stirred for 1 h and then sodium triacetoxyborohydride (215 mg, 1.014 mmol) was added. The resulting mixture was stirred for 1 h. The volatiles were removed in vacuo and the residue was purified by reverse phase automated chromatography (5-50% MeCN/H$_2$O, 0.1% TFA, 15 min, 100 g) to afford ethyl 6,8-difluoro-1-methyl-4-oxo-5-(2-((1r,4s)-4-(((3-oxo-3,4-dihydro-2H-pyrazino[2,3-b][1,4]thiazin-6-yl)methyl)amino)cyclohexyl)ethyl)-1,4-dihydroquinoline-3-carboxylate (220 mg, 0.321 mmol, 79% yield) as a TFA salt. LCMS: m/z 544.2 (MH+). $^1$H NMR (DMSO-d$_6$) □: 11.43 (s, 1H), 8.85-8.99 (m, 2H), 8.48 (s, 1H), 8.23-8.31 (m, 2H), 7.78 (dd, J=14.3, 9.7 Hz, 1H), 4.25-4.31 (m, 2H), 4.22 (q, J=7.1 Hz, 2H), 4.03 (d, J=10.1 Hz, 3H), 3.20-3.30 (m, 2H), 2.44-2.57 (m, 3H), 2.11-2.19 (m, 2H), 1.90 (d, J=1.5 Hz, 2H), 1.31-1.47 (m, 5H), 1.28 (t, J=7.1 Hz, 3H), 0.97-1.13 (m, 2H).

i) 6,8-difluoro-1-methyl-4-oxo-5-(2-((1r,4s)-4-(((3-oxo-3,4-dihydro-2H-pyrazino[2,3-b][1,4]thiazin-6-yl)methyl)amino)cyclohexyl)ethyl)-1,4-dihydroquinoline-3-carboxylic Acid

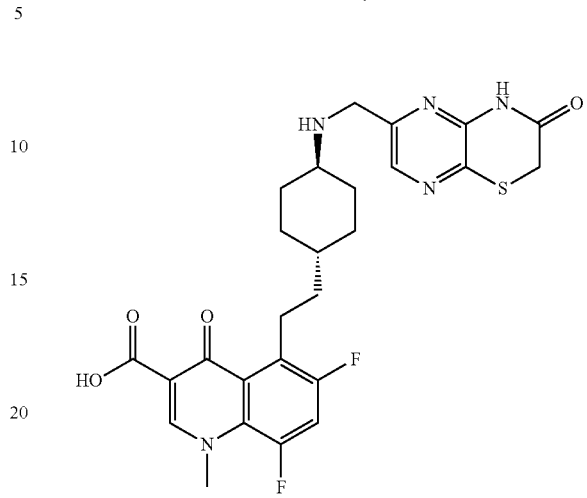

To a slurry of ethyl 6,8-difluoro-1-methyl-4-oxo-5-(2-((1r,4s)-4-(((3-oxo-3,4-dihydro-2H-pyrazino[2,3-b][1,4]thiazin-6-yl)methyl)amino)cyclohexyl)ethyl)-1,4-dihydroquinoline-3-carboxylate (147 mg, 0.214 mmol) in THF (2.14 mL) was added 0.5 M LiOH in water (2.14 mL, 1.07 mmol). The resulting solution was stirred for 5 h. Analysis of the reaction progress by LCMS showed that the starting material was consumed, and desired product as well as hydrolyzed product (thiazinone amide ring-opening) were observed. The reaction mixture was concentrated, and the residue was diluted with 3 mL of AcOH and heated to 70° C. for 3 h. The volatiles were removed in vacuo and the residue was purified by reverse phase chromatography (5-50% MeCN/H$_2$O, 0.1% TFA, 20 min, 100 g column) to afford 6,8-difluoro-1-methyl-4-oxo-5-(2-((1r,4s)-4-(((3-oxo-3,4-dihydro-2H-pyrazino[2,3-b][1,4]thiazin-6-yl)methyl)amino)cyclohexyl)ethyl)-1,4-dihydroquinoline-3-carboxylic acid (104 mg, 0.147 mmol, 69% yield) as a white solid. LCMS: m/z 544.2 (MH+). $^1$H NMR (MeOH-d4) □: 8.81 (s, 1H), 8.22 (s, 1H), 7.67 (dd, J=14.1, 9.6 Hz, 1H), 4.38 (s, 2H), 4.26 (d, J=10.1 Hz, 3H), 3.82 (s, 2H), 3.42-3.53 (m, 2H), 3.18-3.27 (m, 1H), 2.23-2.33 (m, 2H), 2.05-2.17 (m, 2H), 1.46-1.63 (m, 5H), 1.15-1.29 (m, 2H).

Preparation A: 3-Oxo-3,4-dihydro-2H-pyrazino[2,3-b][1,4]thiazine-6-carbaldehyde

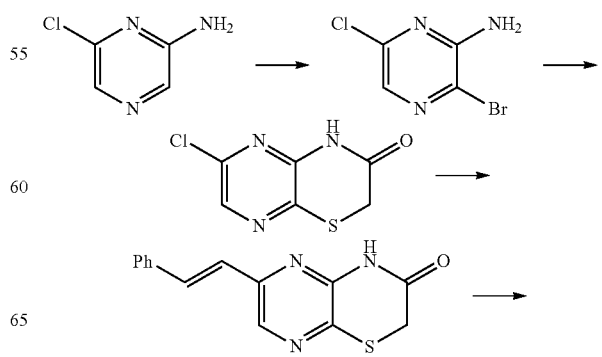

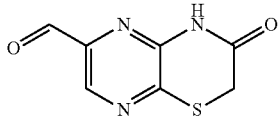

(a) 3-Bromo-6-chloro-2-pyrazinamine

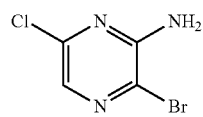

A mixture of 6-chloropyrazin-2-amine (120 g, 0.93 mmol) in CHCl₃(1 L) was stirred at r.t. for 0.5 h. Then NBS (247 g, 1.39 mmol) was added in portions. The reaction mixture was stirred at rt for 2 h and heated to reflux for 3 h. The reaction mixture was cooled to rt and treated with water (1 L). The mixture was extracted with CH₂Cl₂ (5×300 mL). The combined organic layers were washed with brine (200 mL), dried over Na₂SO₄ and evaporated in vacuo. The resulting residue was purified by column chromatography on silica gel (PE:DCM=5:1) to afford the crude product, which was recrystallized in DCM:PE (1:5) to afford the product (21.7 g, 11%), as a yellowish solid.

1H NMR (400 MHz, CDCl₃): δ 7.68 (s, 1H), 5.32 (s, 2H).

(b) 6-Chloro-2H-pyrazino[2,3-b][1,4]thiazin-3(4H)-one

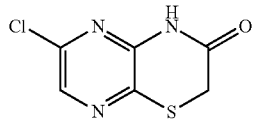

The mixture of NaH (28.8 mg, 60%, 0.72 mmol) in DMF (5 mL) was stirred at 0° C. for 15 min, and then ethyl mercaptoacetate (86.5 mg, 0.72 mmol) was added dropwise at 0° C. The reaction mixture was stirred at 0° C. for 1 h. 3-Bromo-6-chloro-2-pyrazinamine (100 mg, 0.48 mmol) was added in portions. The reaction mixture was stirred at rt overnight. The reaction mixture was poured into ice-water (100 mL). The mixture was extracted with EtOAc (3×10 mL). The combined organic layers were dried over Na₂SO₄ and purified by pre-TLC (PE:EA 3:1) to afford the product (30 mg, 31%), as a white solid.

1H NMR (400 MHz, DMSO): δ 11.51 (s, 1H), 8.23 (s, 1H), 3.81 (s, 2H).

(c) 6-[(E)-2-phenylethenyl]-2H-pyrazino[2,3-b][1,4]thiazin-3(4H)-one

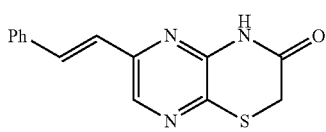 [SMILES: O=C1CSc2ncc(/C=C/c3ccccc3)nc2N1]

A mixture of 6-chloro-2H-pyrazino[2,3-b][1,4]thiazin-3(4H)-one (500 mg, 2.48 mmol), [(E)-2-phenylethenyl]boronic acid (733 mg, 4.96 mmol), Pd(dppf)C₁₂(181 mg, 0.25 mg) and K₂CO₃ (1.7 g, 12.40 mmol) in 1,4-dioxane (6 mL) containing 2 mL of water was stirred at 110° C. overnight under N₂. 50 mL of water was added. The reaction mixture was extracted with EtOAc (5×5 mL). The combined organic layers were dried over Na₂SO₄ and purified by column chromatography on silica gel (PE:EA=20:1-7:1) to afford the product (180 mg, 27%) as a yellow solid.

¹H NMR (400 MHz, CDCl₃): δ 8.17 (s, 1H), 8.10 (s, 1H), 7.64 (d, J=16, 1H), 7.55 (d, J=18, 2H), 7.41-7.31 (m, 3H), 7.03 d, J=16, 1H), 3.71 (s, 2H).

(d) 3-Oxo-3,4-dihydro-2H-pyrazino[2,3-b][1,4]thiazine-6-carbaldehyde Note Book

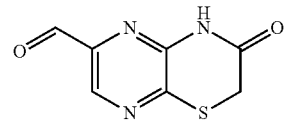 [SMILES: O=Cc1cnc2c(n1)NC(=O)CS2]

A mixture of 6-[(E)-2-phenylethenyl]-2H-pyrazino[2,3-b][1,4]thiazin-3(4H)-one (20 mg, 0.074 mmol), OsO₄ (1.3 mg, 0.005 mmol) and NaIO₄ (24 mg, 0.11 mmol) in 1,4-dioxane (2 mL) containing 0.1 mL of water was stirred at rt overnight. The solvent was removed in vacuo. The resulting residue was poured to 20 mL of EtOAc. The mixture was stirred at rt for 1 h and filtered. The filtrate was concentrated in vacuo to afford the product (7 mg, 49%), as a grey solid.

1H NMR (400 MHz, DMSO): δ 11.60 (s, 1H), 9.89 (s, 1H), 8.56 (s, 1H), 3.90 (s, 2H).

Alternative Preparation A

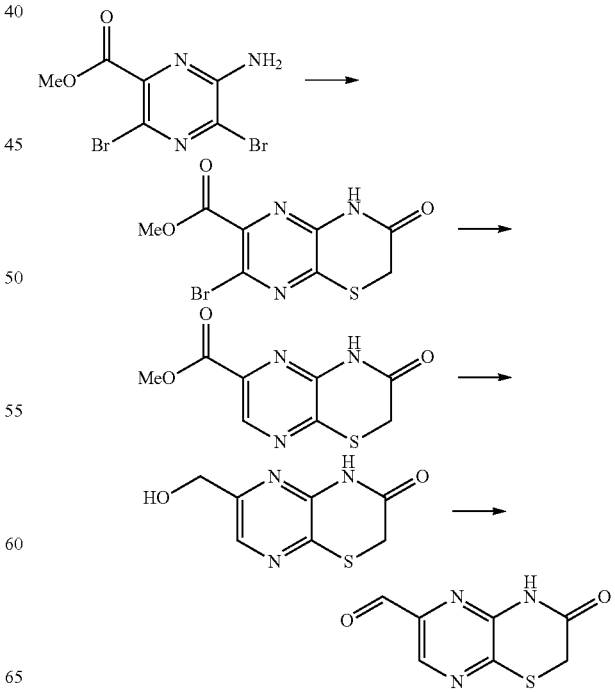

(a) Methyl 7-bromo-3-oxo-3,4-dihydro-2H-pyrazino[2,3-b][1,4]thiazine-6-carboxylate

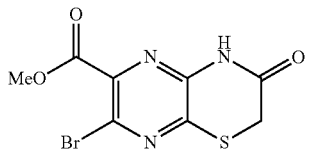

A solution of methyl 6-amino-3,5-dibromo-2-pyrazinecarboxylate (see alternative preparation B (c)) (1000 g, 3.24 mol, 1 equiv), K₂CO₃ (893 g, 6.47 mol, 2.0 equiv) in DMF (10 L) was placed in a 20 L 4-necked round-bottom flask. Ethyl 2-mercaptoacetate (349 g, 2.91 mol, 0.9 equiv) was added dropwise to above the solution while maintaining the temperature at −10-0° C. (about 1 hours added completion). The resulting solution was allowed to react for 2 h while maintaining the temperature at 70° C. The reaction progress was monitored by LCMS until the starting material was consumed completely. The reaction mixture was cooled to room temperature. The reaction was then quenched by 20 L water. The pH value of the solution was adjusted to 3-4 with 6M hydrogen chloride. The resulting solution was extracted with ethyl acetate (3×10 L) and the organic layers were combined. The organic phase was dried over anhydrous sodium sulfate. The organic phase was concentrated under vacuum. The residue product was purified by chromatogram on silica gel with DCM/EA (1:1) to give the desired product (350 g, 95% purity, 35% yield) as a light yellow solid 1H-NMR (300 MHz, DMSO-d6) δ: 12.03 (1H, s), 5.76 (2H, s), 3.86 (3H, s).

(b) Methyl 3-oxo-3,4-dihydro-2H-pyrazino[2,3-b][1,4]thiazine-6-carboxylate

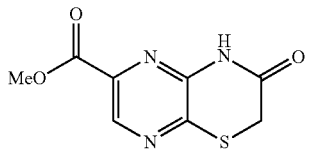

A solution of NaOAc (870 g, 10.6 mol, 2.0 equiv), Pd/C (10%, 800 g), methyl 7-bromo-3-oxo-3,4-dihydro-2H-pyrazino[2,3-b][1,4]thiazine-6-carboxylate (1.6 kg, 5.28 mol, 1 equiv) in MeOH (32 L) and THF (32 L) was placed in a 100 L pressure tank reactor (30 atm). The resulting solution was stirred for 24 h at 50° C. The reaction progress was monitored by LCMS until the starting material was consumed completely. The reaction mixture was hot to 60° C. for 1 h. A filtration was performed to remove Pd/C. The resulting mixture was washed with THF (20 L×2). The resulting mixture was concentrated (to 1 L) under vacuum. The solids were collected by filtration and added in 2 L water. The pH value of the solution was adjusted to 3-4 with 3M hydrogen chloride. The solids were collected by filtration and dried to give the product (0.95 kg, 98% purity, 80% yield) as a yellow solid.

1H-NMR (300 MHz, DMSO-d6) δ: 11.61 (1H, s), 8.64 (1H, s), 3.90 (2H, s), 3.89 (3H, s)

(c) 6-(Hydroxymethyl)-2H-pyrazino[2,3-b][1,4]thiazin-3 (4H)-one

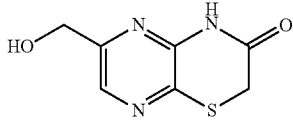

A solution of methyl 3-oxo-3,4-dihydro-2H-pyrazino[2,3-b][1,4]thiazine-6-carboxylate (400 g, 1.78 mol, 1 equiv) in THF (8 L) was placed in a 20 L 4-necked round-bottom flask under N₂. LiBHEt₃ (1M) (5.7 L, 3.2 equiv) was added dropwise to above the solution while maintaining the temperature at −10-0° C. (about 1 hours added completion). The resulting solution was allowed to react for 1 h while maintaining the temperature at −10-0° C. The reaction progress was monitored by LCMS until the starting material was consumed completely. The pH value of the solution was adjusted to 3-4 with 6M hydrogen chloride (about 500 ml). The resulting solution was extracted with THF (2×5 L) and the organic layers were combined. The organic phase was dried over anhydrous sodium sulfate. The organic phase was concentrated (to 1 L) under vacuum. The solids were collected by filtration and dried to give the product (189 g, 98% purity, 54% yield) as a yellow solid.

1H-NMR (300 MHz, DMSO-d6) δ: 11.21 (1H, s), 8.17 (1H, s), 5.59 (1H, b), 4.51 (2H, s), 3.78 (2H, s)

(d) 3-Oxo-3,4-dihydro-2H-pyrazino[2,3-b][1,4]thiazine-6-carbaldehyde

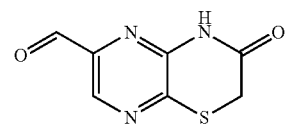 [SMILES: O=Cc1cnc2c(n1)NC(=O)CS2]

A solution of 6-(hydroxymethyl)-2H-pyrazino[2,3-b][1,4]thiazin-3(4H)-one (200 g, 1.02 mol, 1 equiv) in THF (4 L) and DCE (4 L) was placed in a 20 L 4-necked round-bottom flask. MnO₂ (2.2 kg, 25.4 mol, 25 equiv) was added in several portions to above the solution while maintaining the temperature at 75-80° C. The reaction progress was monitored by LCMS until the starting material was consumed completely. A filtration was performed to remove MnO₂. The filtrate was concentrated (to 1 L) under vacuum. The solids were collected by filtration and dried. The product (60 g g, 98% purity, 30% yield) was obtained as a yellow solid. The mother liquid was purified by chromatogram on silica gel with EA/DCM (1:1) to give the desired product (20 g) in a light yellow solid. In all, the product (79 g, 95% purity, 40% yield) was obtained as a yellow solid.

1H-NMR (300 MHz, DMSO-d6) δ: 11.65 (1H, s), 9.93 (1H, s), 8.62 (1H, s), 3.92 (2H, s).

Preparation B: 3-Oxo-3,4-dihydro-2H-pyrazino[2,3-b][1,4]oxazine-6-carbaldehyde

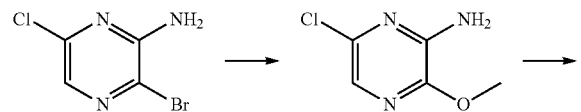

-continued

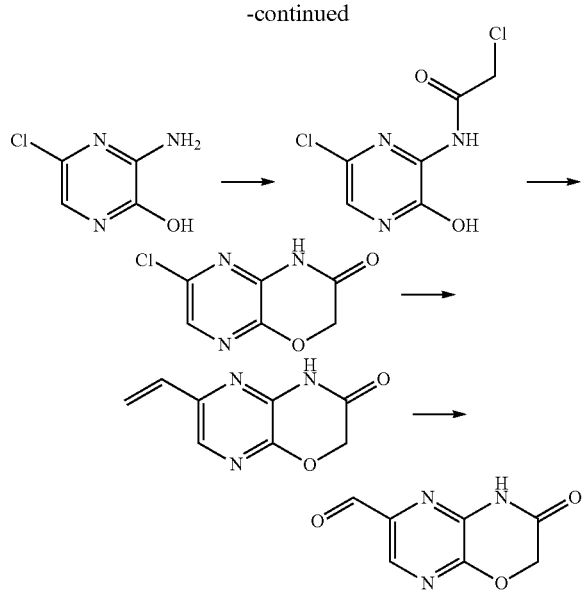

(a) 6-Chloro-3-(methyloxy)-2-pyrazinamine

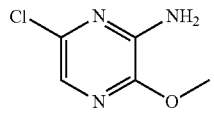

A mixture of 3-bromo-6-chloro-2-pyrazinamine (15 g, 72 mmol) in MeOH (200 mL) was stirred at rt for 10 min. Then, sodium methoxide (3.9 g, 72 mmol) was added at rt. The reaction mixture was stirred at 80dec overnight. MeONa (3.9 g, 72 mmol) was added. The mixture was stirred at 80° C. for 24 h. The reaction mixture was poured into ice-water (500 mL) and extracted with DCM (5×50 mL). The combined organic layers were dried over $Na_2SO_4$ and filtered. The solvent was removed in vacuo. The resulting residue was purified by column chromatography on silica gel (PE: DCM 5:1) to afford the product (7.5 g, 65%), as a yellow solid.

1H NMR (400 MHz, $CDCl_3$): δ 7.37 (s, 1H), 5.00 (brs, 1H), 3.97 (s, 3H).

(b) 3-Amino-5-chloro-2(1H)-pyrazinone

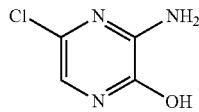

A mixture of 6-chloro-3-(methyloxy)-2-pyrazinamine (7.5 g, 47 mmol) in DCE (400 mL) was stirred at rt for 1 h. $BBr_3$ (22 mL, 23.5 mmol) was added dropwise at rt. The reaction mixture was stirred at 60° C. overnight. The mixture was quenched with the addition of $CH_3OH$ (50 mL) at 0° C. The mixture was allowed to warmed to rt and stirred for 1 h at rt. The solid was collected by filtration and washed with DCM (5×10 mL). The solid was then dried in vacuo to afford the product (8 g).

(c) 2-Chloro-N-(6-chloro-3-oxo-3,4-dihydro-2-pyrazinyl)acetamide

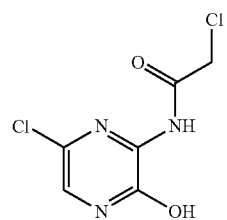 [SMILES: O=C(CCl)Nc1nc(Cl)cnc1O]

The mixture of 3-amino-5-chloro-2(1H)-pyrazinone (6 g, 28.8 mmol) and chloroacetic anhydride (19.7 g, 115 mmol) in $CH_3CN$ (80 mL) was stirred at 80dec overnight. The solvent was removed in vacuo. The resulting residue was washed with PE:EA (3:1) to afford the product (3 g, 56%), as black solid.

1H NMR (400 MHz, DMSO): δ 12.61 (brs, 1H), 10.32 (s, 1H), 7.40 (s, 1H), 4.49 (s, 2H).

(d) 6-Chloro-2H-pyrazino[2,3-b][1,4]oxazin-3(4H)-one

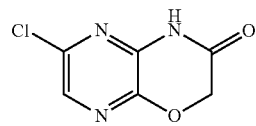 [SMILES: O=C1COc2ncc(Cl)nc2N1]

The mixture of 2-chloro-N-(6-chloro-3-oxo-3,4-dihydro-2-pyrazinyl)acetamide (3 g, 13.5 mmol) and KOH (2.3 g, 40.5 mmol) in Ethanol (50 mL) was stirred at rt overnight. The solvent was removed in vacuo and the resulting residue was purified by prep-HPLC to afford the product (1 g, 39%), as white solid.

1H NMR (400 MHz, DMSO): δ 11.85 (s, 1H), 7.86 (s, 1H), 4.90 (s, 2H).

(e) 6-Ethenyl-2H-pyrazino[2,3-b][1,4]oxazin-3(4H)-one

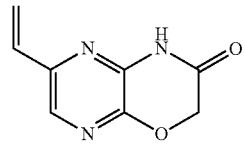

The mixture of 6-chloro-2H-pyrazino[2,3-b][1,4]oxazin-3(4H)-one (300 mg, 1.6 mmol), tributyl(vinyl)tin (1.52 g, 4.8 mmol) and $Pd(PPh_3)_4$ (184 mg, 0.16 mmol) in 1,4-dioxane (6 mL) and Toluene (6 mL) was stirred at 100° C. for 3 days under $N_2$. The mixture was filtered and the filtrate was concentrated in vacuo. The resulting residue was purified by prep-TLC (PE:EA 3:1) to afford the product (40 mg, 14%), as white solid.

1H NMR (400 MHz, $CDCl_3$): δ 8.51 (s, 1H), 7.83 (s, 1H), 6.70 (dd, J=10.8 and 17.2 Hz, 1H), 6.15 (dd, J=1.2 and 17.2 Hz, 1H), 5.47 (dd, J=0.8 and 10.8 Hz, 1H), 4.92 (s, 2H)

(f) 3-Oxo-3,4-dihydro-2H-pyrazino[2,3-b][1,4]oxazine-6-carbaldehyde

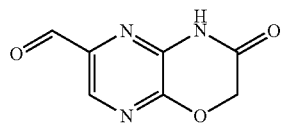 [SMILES: O=Cc1cnc2c(n1)NC(=O)CO2]

6-Ethenyl-2H-pyrazino[2,3-b][1,4]oxazin-3(4H)-one (40 mg, 0.22 mmol) was dissolved in THF (3 mL) and $H_2O$ (0.6 mL). Then, $NaIO_4$ (141 mg, 0.66 mmol) and $OsO_4$ (1.1 mg, 0.0045 mmol) was added. The reaction mixture was stirred at r.t. for 5 h. 100 mL of water was added. The mixture was extracted with EtOAc (5×20 mL). The combined organic layers were dried over $Na_2SO_4$ and the solid was filtered off. The filtrate was purified by prep-TLC (PE:EA 1:1) to afford the product (20 mg, 49%).

1H NMR (400 MHz, DMSO): δ 11.95 (s, 1H), 9.86 (s, 1H), 8.36 (s, 1H), 4.99 (s, 2H).

Alternative Preparation B

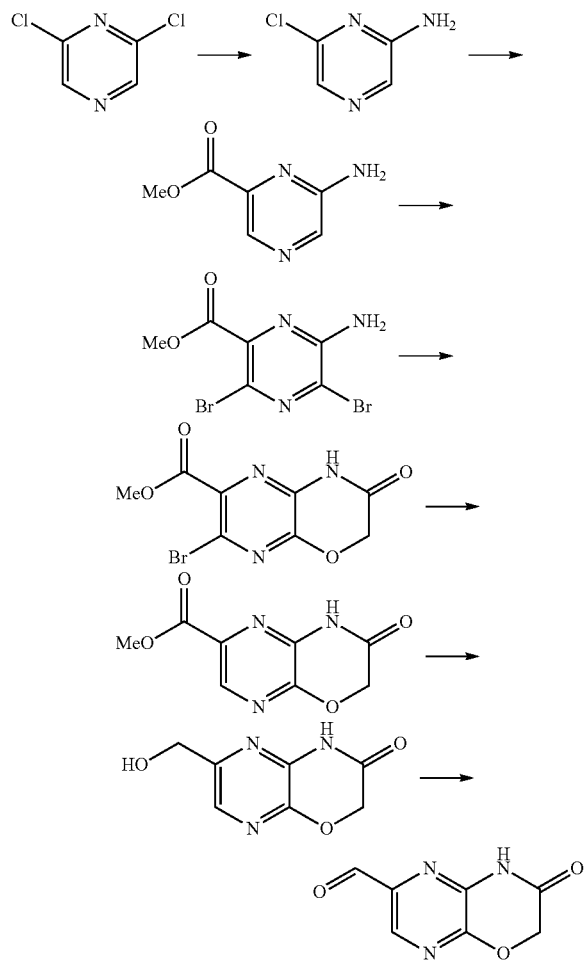

(a) 6-Chloro-2-pyrazinamine

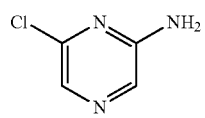

A solution of 2,6-dichloropyrazine (15 kg, 101.4 mol, 1.00 equiv) in water (20 L), ammonia water (25 L, 25%) was placed in a 100 L pressure tank reactor. The resulting solution was stirred for 6 h at 120° C. The reaction progress was monitored by TLC (EA:PE=1:1) until the starting material was consumed, and cooled to room temperature. The solids were collected by filtration. The solid was washed with water and dried. The solid was washed with petroleum ether to remove the unreacted starting materials. The product (7.8 kg, purity=95%, 60% yield) was obtained as a white solid.

(b) Methyl 6-amino-2-pyrazinecarboxylate

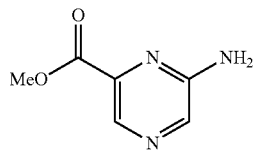 [SMILES: COC(=O)c1cncc(N)n1]

A solution of 6-chloro-2-pyrazinamine (4 kg, 31 mol, 1.00 equiv), $Et_3N$ (4.7 kg, 46.5 mol, 1.50 equiv), $Pd(OAc)_2$ (139 g, 0.62 mol, 0.02 equiv), dppf (343 g, 0.62 mol, 0.02 equiv) in methanol (60 L) was placed in a 100 L pressure tank reactor (10 atm).

The resulting solution was allowed to react for 5 h while maintaining the temperature at 85° C. The reaction progress was monitored by TLC (DCM:MeOH=20:1) until the starting material was consumed completely, and cooled to room temperature. The resulting mixture was concentrated under vacuum. The residue was washed with water 50 L. The filter was collected and dried. The product (3.8 kg, purity=95%, 80% yield) was obtained as a pale brown solid.

1H-NMR (300 MHz, DMSO-d6) δ: 8.27 (1H, s), 8.06 (1H, s), 6.87 (2H, b), 3.84 (3H, s).

LC-MS: m/z=154(M+H)+.

(c) Methyl 6-amino-3,5-dibromo-2-pyrazinecarboxylate

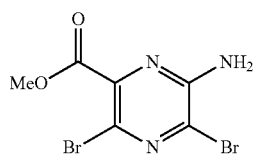 [SMILES: COC(=O)c1nc(N)c(Br)nc1Br]

A solution of methyl 6-amino-2-pyrazinecarboxylate (17 kg, 111 mmol, 1.00 equiv) in N,N-dimethylformamide (100 L) was placed in a 200 L reactor. N-Bromosuccinimide (56 kg, 333 mol, 3.3 equiv) was added in several portions to above the solution while maintaining the temperature at 0°

C. The reaction progress was monitored by TLC (EA:PE=1:1) until the starting material was consumed completely. The reaction was quenched with 300 L water/ice. The solids were collected by filtration and dried. The crude product was re-crystallized in a solvent of MeOH (5 vol: 1 g). The product (17 kg, purity=98%, 54%) was obtained as a yellow solid.

1H-NMR (300 MHz, DMSO-d6) δ: 7.36 (2H, b), 3.87 (3H, s).

(d) Methyl 7-bromo-3-oxo-3,4-dihydro-2H-pyrazino[2,3-b][1,4]oxazine-6-carboxylate

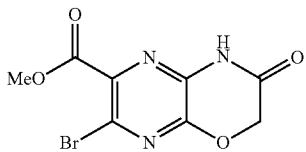

A solution of ethyl 6-amino-3,5-dibromo-2-pyrazinecarboxylate (2.5 kg, 8.1 mol, 1 equiv in methyl 2-hydroxyacetate (8.7 kg, 97.1 mol, 12 equiv) was placed in a 20 L 4-necked round-bottom flask under $N_2$. t-BuOK (2.71 kg, 24.3 mol, 3 equiv) was added in several portions to above the solution while maintaining the temperature at 50-60° C. (about 1 hours added completion). The resulting solution was allowed to react for 1 h while maintaining the temperature at 50-60° C. The reaction progress was monitored by LCMS until the starting material was consumed completely. The reaction mixture was cooled to room temperature. The reaction was then quenched by 20 L water. The pH value of the solution was adjusted to 3-4 with 6M hydrogen chloride. The solids were collected by filtration and dried. The crude product was purified by chromatogram on silica gel with DCM:EA (1:1) to give the desired product (1.3 kg, 95% purity, 56% yield) as a light yellow solid 1H-NMR (300 MHz, DMSO-d6) δ: 11.97 (1H, b), 4.98 (2H, s), 3.88 (3H, s).

(e) Methyl 3-oxo-3,4-dihydro-2H-pyrazino[2,3-b][1,4]oxazine-6-carboxylate

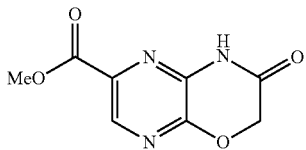

A solution of NaOAc (1000 g, 12.2 mol, 2.06 equiv), Pd/C (10%, 340 g), methyl 7-bromo-3-oxo-3,4-dihydro-2H-pyrazino[2,3-b][1,4]oxazine-6-carboxylate in MeOH (34 L) and THF (34 L) was placed in a 100 L pressure tank reactor (3 atm). The resulting solution was stirred for 3 h at 30° C. The reaction progress was monitored by LCMS until the starting material was consumed completely. The reaction mixture was hot to 60° C. for 1 h. A filtration was performed to remove Pd/C. The resulting mixture was washed with THF (20 L×2). The resulting mixture was concentrated (to 1 L) under vacuum. The solids were collected by filtration and added in 2 L water. The pH value of the mixture was adjusted to 3-4 with 3M hydrogen chloride. The solids were collected by filtration and dried. The product (0.9 kg, 98% purity, 80% yield) was obtained as a yellow solid.

1H-NMR (300 MHz, DMSO-d6) δ: 11.94 (1H, s), 8.39 (1H, S), 4.98 (2H, s), 3.86 (3H, s).

(f) 6-(hydroxymethyl)-2H-pyrazino[2,3-b][1,4]oxazin-3 (4H)-one

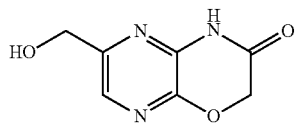 [SMILES: O=C1COc2ncc(CO)nc2N1]

A solution of methyl 3-oxo-3,4-dihydro-2H-pyrazino[2,3-b][1,4]oxazine-6-carboxylate (400 g, 2.22 mol, 1 equiv) in THF (8 L) was placed in a 20 L 4-necked round-bottom flask under $N_2$. $LiBHEt_3$ (1M) (6.1 L, 3.2 equiv) was added dropwise to the solution, while maintaining the temperature at −10-0° C. (about 1 hours added completion). The resulting solution was allowed to react for 1 h while maintaining the temperature at −10-0° C. The reaction progress was monitored by LCMS until the starting material was consumed completely. The pH value of the solution was adjusted to 3-4 with 6M hydrogen chloride (about 500 ml). The resulting solution was extracted with THF (2×5 L) and the organic layers were combined. The organic phase was dried over anhydrous sodium sulfate. The organic phase was concentrated (to 2 L) under vacuum. The solids were collected by filtration and dried. The product (173 g, 98% purity, 50% yield) was obtained as a yellow solid.

1H-NMR (300 MHz, DMSO-d6) δ: 11.57 (1H, s), 7.79 (1H, s), 5.47 (1H, b), 4.86 (2H, s), 4.46 (2H, s).

(g) 3-Oxo-3,4-dihydro-2H-pyrazino[2,3-b][1,4]oxazine-6-carbaldehyde

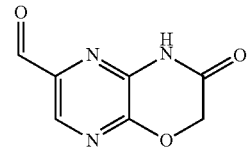 [SMILES: O=Cc1cnc2c(n1)NC(=O)CO2]

A solution of 6-(hydroxymethyl)-2H-pyrazino[2,3-b][1,4]oxazin-3(4H)-one (200 g, 1.1 mol, 1 equiv) in THF (8 L) and DCE (4 L) was placed in a 20 L 4-necked round-bottom flask. $MnO_2$ (1150 g, 13.3 mol, 12 equiv) was added in several portions to above the solution while maintaining the temperature at 75-80° C. (about 24 hours added completion). The reaction progress was monitored by LCMS until the starting material was consumed completely. A filtration was performed to remove $MnO_2$. The filtrate was concentrated (to 2 L) under vacuum. The solids were collected by filtration and dried. The product (110 g, 98% purity, 60% yield) was obtained as a off-white solid.

1H-NMR (300 MHz, DMSO-d6) δ: 11.98 (1H, s), 9.88 (1H, s), 8.38 (1H, s), 5.01 (2H, s).

Example 34: 6-((((1R,4R)-4-(((6-fluoro-3-methoxy-quinoxalin-5-yl)methyl)amino) cyclohexyl)amino)methyl)-2H-pyrazino[2,3-b][1,4]oxazin-3(4H)-one, HCl A11=*Mycobacterium tuberculosis*

Compound W=6-({[(1S,3R,4S)-4-{[(6-fluoro-3-methoxy-quinoxalin-5-yl)methyl]amino}-3-hydroxycyclohexyl]amino}methyl)-2H,3H,4H-pyrazino[2,3-b][1,4]oxazin-3-one Compound Y=1-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-7-methoxy-1,2-dihydro-1,8-naphthyridin-2-one

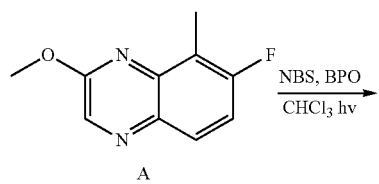

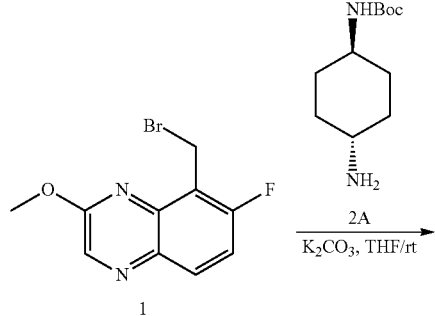

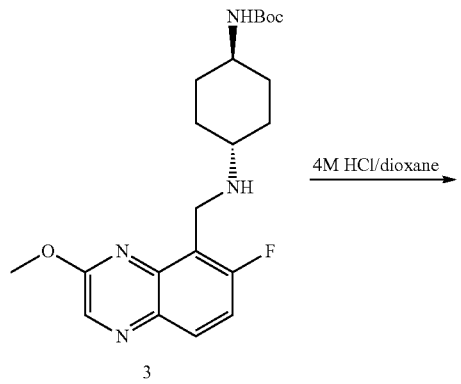

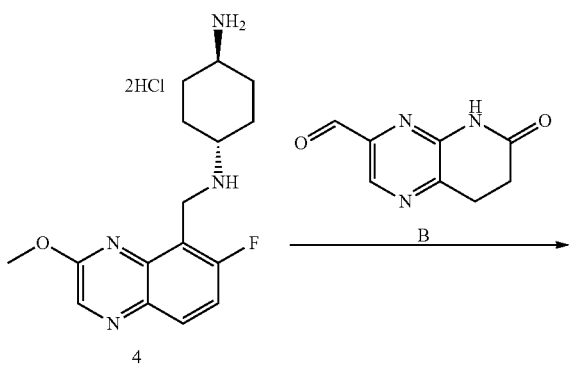

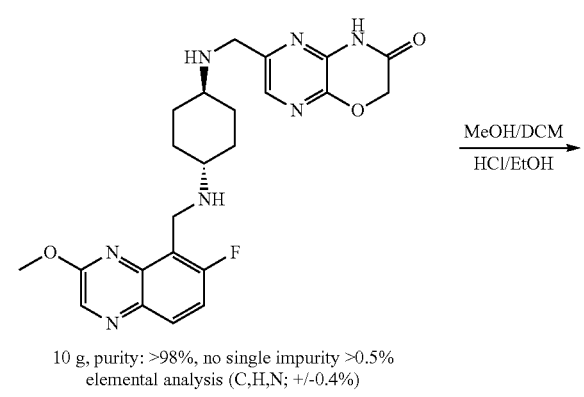

10 g, purity: >98%, no single impurity >0.5%
elemental analysis (C,H,N; +/-0.4%)

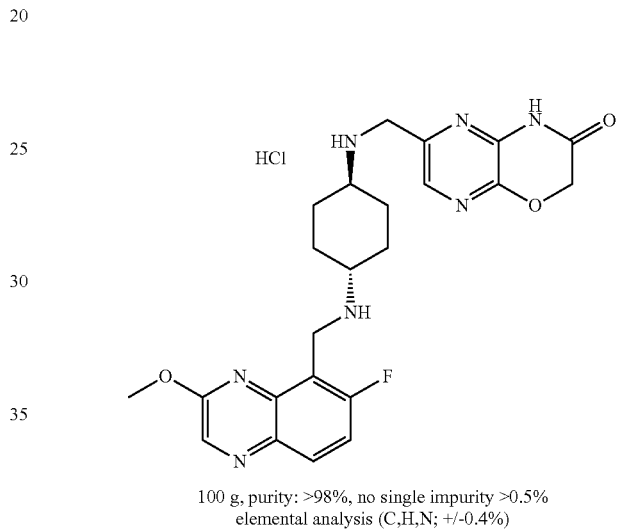

100 g, purity: >98%, no single impurity >0.5%
elemental analysis (C,H,N; +/-0.4%)

To a solution of compound A (84 g, 437 mmol) in CHCl$_3$ (1.5 L) was added NBS (86 g, 481 mmol) in portions at 0° C. over 20 min, followed by BPO (5.29 g, 21.85 mmol) portionwise over 10 min. The ice-bath was removed from the reaction, a reflux condenser was added and the reaction was heated to 60° C. A 120 W lamp was placed to shine on the reaction inside an aluminium foil tent. The reaction was stirred at 60° C. under the light for 5.5 h. The reaction was detected and showed there was one peak and was the desired MS of the product. TLC (Petroleum ether:Ethyl acetate=50:1, Rf=0.4), showed the starting material was consumed completely and has a new spot. The reaction mixture was cooled to room temperature (25° C.) and H$_2$O (1.5 L) was added, the separated aqueous was extracted with CH$_2$C$_{12}$ (1 L×3). The combined organic was washed with Sat. Na$_2$SO$_3$ solution (600 mL), dried over Na$_2$SO$_4$ and concentrated under reduced pressure. Compound 1 (118 g, 99% yield) was present as a light yellow solid.

$^1$H NMR: (CDCl$_3$, 400 MHz) δ 8.46 (s, 1H), 8.01~7.97 (dd, J$_1$=6.0 Hz, J$_2$=9.2 Hz, 1H), 7.33 (t, J=9.2 Hz, 1H), 5.07 (d, J=1.2 Hz, 2H), 4.16 (s, 3H).

Example 35: 6-((((1R,4R)-4-(((6-fluoro-3-methoxy-quinoxalin-5-yl)methyl)amino) cyclohexyl)amino) methyl)-2H-pyrazino[2,3-b][1,4]oxazin-3(4H)-one, HCl

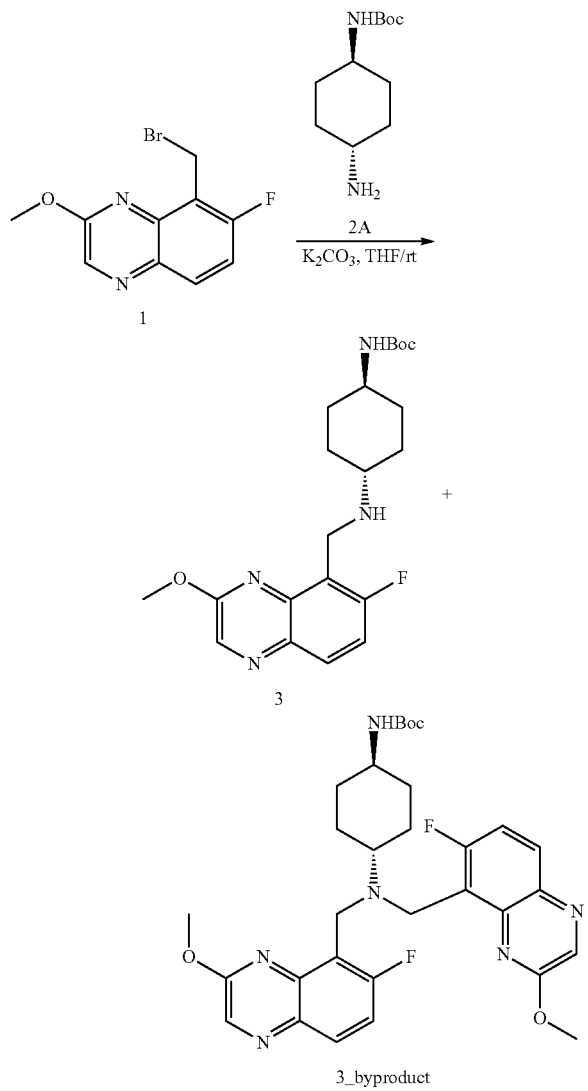

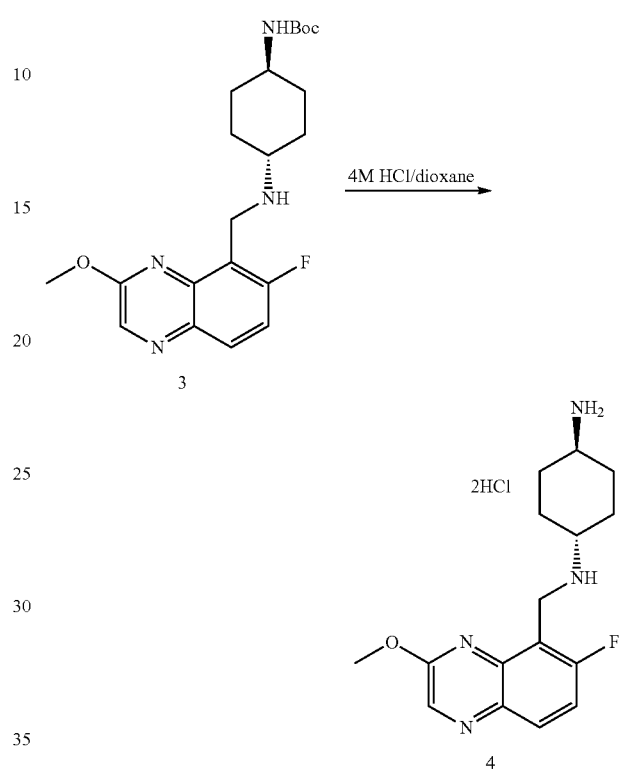

Step A

To a mixture of compound 1 (110 g, 428 mmol) and compound 2A (128 g, 599 mmol) in THF (2 L) was added $K_2CO_3$ (83 g, 599 mmol) at 25° C. The reaction mixture was stirred at 25° C. for 16 h. The mixture was detected by LCMS showed the starting material was consumed completely. It showed about 62% of the desired MS peak and about 29% of 3_byproduct. The mixture was concentrated under reduced pressure to remove THF, $H_2O$ (2.5 L) was added, then the mixture was extracted with $CH_2Cl_2$ (2 L×3), the combined organic was concentrated under reduced pressure to afford crude product. The crude was purified by silica gel chromatography column ($CH_2Cl_2$/MeOH=100:1~8:1). Compound 3 (88 g, 51% yield) was present as a yellow solid.

$^1$H NMR: (CDCl$_3$, 400 MHz) δ 8.44 (s, 1H), 7.94~7.90 (dd, J$_1$=6.0 Hz, J$_2$=9.2 Hz, 1H), 7.32 (t, J=8.8 Hz, 1H), 4.32 (d, J=1.2 Hz, 3H), 4.09 (s, 3H), 3.41 (br, s, 1H), 2.40-2.35 (m, 1H), 2.01-1.99 (d, J=11.2 Hz, 4H), 1.43 (s, 9H), 1.30-1.22 (dd, J$_1$=12.0 Hz, J$_2$=22.8 Hz, 2H), 1.13-1.04 (dd, J$_1$=11.6 Hz, J$_2$=22.0 Hz, 2H).

Step B

To a solution of compound 3 (100 g, 247 mmol) in $CH_2Cl_2$ (1.2 L) and MeOH (1.2 L) was added HCl/dioxane (4 M, 921 mL) dropwise at ice-bath, maintaining the temperature below 25° C. The solution became to slurry and then was allowed to stir at 25° C. for 20 h. The mixture was detected by LCMS showed the starting material was almost consumed completely, and the desired MS peak has been detected. The mixture was concentrated under reduced pressure to remove solvent. The residue was reconcentrated under vacuum with MeOH (100 mL×3). Compound 4 (93.27 g, crude) was present as a white solid.

Step C

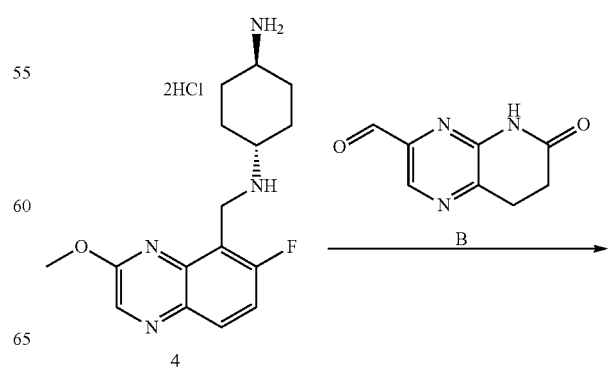

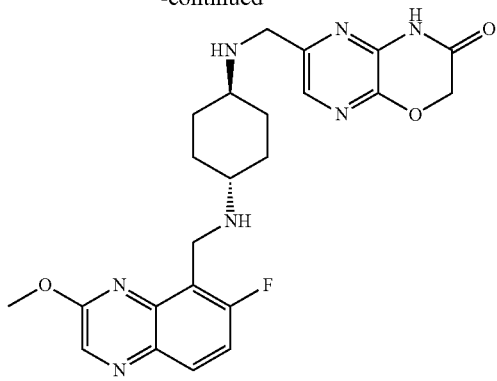

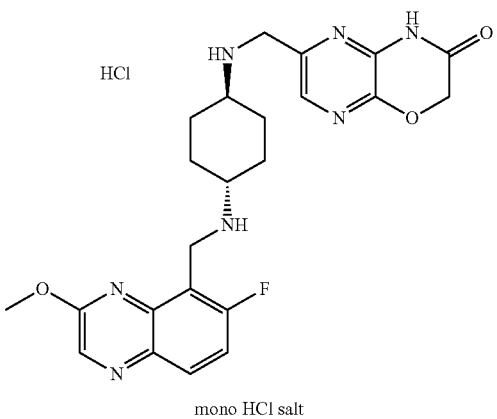

mono HCl salt

To a mixture of compound 4 (62 g, 164 mmol) and compound B (26.5 g, 148 mmol) in isopropanol (600 mL) and CHCl₃ (3.50 L) was added Et₃N (56 g, 553 mmol, 77 mL) at 25° C. The mixture was stirred at 25° C. for 16 h. Solid had dissolved, NaBH(OAc)₃ (87 g, 411 mmol) was added portionwise to the reaction over 5 min. The reaction mixture was stirred at 25° C. for 4 h. The mixture was detected by LCMS showed the desired MS peak had been detected, but the starting material was not consumed completely. The mixture was continue stirred at 25° C. for 2 h, detected by LCMS showed the starting material was still not consumed completely. Additional NaBH(OAc)₃ (20 g) was added and stirred at 25° C. for 16 h. The mixture was detected by LCMS showed the starting material was still not consumed completely. The mixture was poured into saturated NaHCO₃solution (12 L), the separated aqueous was extracted with CH₂Cl₂/MeOH=10:1 (5 L×3), the combined organic was dried over Na₂SO₄ and concentrated under reduced pressure to afford crude product. The crude was purified by silica gel chromatography column (CH₂Cl₂/MeOH=100:1-8:1). The product was present (60 g, 78% yield) as a yellow solid.

¹H NMR: (CDCl₃, 400 MHz) δ 8.45 (s, 1H), 7.95~7.91 (dd, J₁=6.0 Hz, J₂=9.2 Hz, 1H), 7.79 (s, 1H), 7.32 (t, J=8.8 Hz, 1H), 4.85 (s, 2H), 4.35 (d, J=1.2 Hz, 2H), 4.09 (s, 3H), 3.82 (s, 2H), 3.47 (s, 5H), 2.52-2.42 (m, 6H), 1.99 (t, J=14.8 Hz, 4H), 1.28~1.11 (m, 4H).

Example 36: 6-((((1R,4R)-4-(((6-fluoro-3-methoxy-quinoxalin-5-yl)methyl)amino) cyclohexyl)amino) methyl)-2H-pyrazino[2,3-b][1,4]oxazin-3(4H)-one, HCl To a solution of the free base (200 g, 427 mmol) in CH₂Cl₂ (1.08 L) and MeOH (1.08 L) was added HCl/EtOH (1.14 M, 375 mL) dropwise at 0° C. Solid was precipitated out. The slurry was stirred at 0° C. for 1 h. The mixture was filtered and collected the solid. The solid was washed with EtOH (50 mL) and hexane (100 mL). The solid was collected and dried under vacuum to afford 130 g of product. HNMR showed it contained MeOH. The filtrate was concentrated under reduced pressure to yield the mono HCl salt (80 g, 37.11% yield) as a yellow solid.

The 130 g product was re-slurry in isopropanol (500 mL) and stirred at 80° C. for 3 h. The mixture was cooled down and filtered. The operation was repeated one more time to remove most of MeOH. The solid was dried to yield the mono HCl salt (118 g, 55% yield) as a white solid.

¹H NMR: (D₂O, 400 MHz) δ 8.41 (s, 1H), 8.04~8.00 (dd, J₁=5.6 Hz, J₂=9.2 Hz, 1H), 7.75 (s, 1H), 7.45 (t, J=9.2 Hz, 1H), 4.92 (s, 2H), 4.85 (s, 2H), 4.17 (s, 2H), 4.05 (s, 3H), 3.33 (br, m, 1H), 3.14 (br, s, 1H), 2.39~2.37 (d, J=14.4 Hz, 2H), 2.27~2.24 (d, J=14.4 Hz, 2H), 1.59~1.44 (m, 4H).

Example 37: 6-((((1R,4R)-4-(((6-fluoro-3-methoxy-quinoxalin-5-yl)methyl)amino) cyclohexyl)amino) methyl)-2H-pyrazino[2,3-b][1,4]oxazin-3(4H)-one

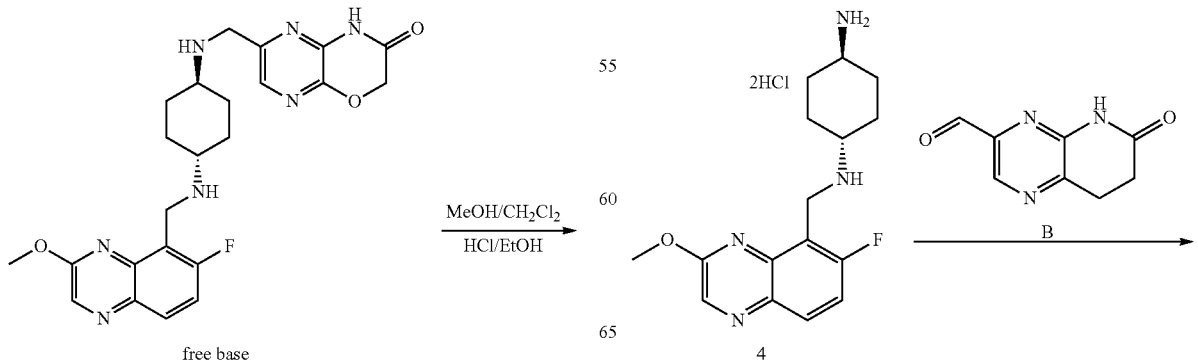

119

-continued

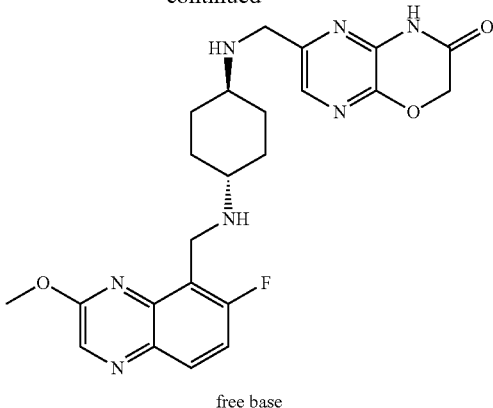

free base

To a mixture of compound 4 (35 g, 93 mmol) and compound B (15 g, 85 mmol) in isopropanol (350 mL) and CHCl₃ (2.00 L) was added Et₃N (31.64 g, 312 mmol, 43.34 mL) at 25° C. The mixture was stirred at 25° C. for 16 h. Solid had dissolved, NaBH(OAc)₃ (49 g, 232 mmol) was added portionwise to the reaction over 5 min. The reaction mixture was stirred at 25° C. for 18 h. The mixture was detected by LCMS and showed the starting material MS peak as 10% and the desired MS peak as about 73%. The mixture was poured into saturated NaHCO₃ solution (4 L), the separated aqueous was extracted with CH₂Cl₂/MeOH=10:1 (2 L×3), the combined organic was dried over Na₂SO₄ and concentrated under reduced pressure to afford crude product. The crude was purified by silica gel chromatography column. The free base was present (11 g, 25% yield, 99% purity) as a yellow solid and 45% yield, 97% purity) as a yellow solid.

¹H NMR: (CDCl₃, 400 MHz) δ 8.45 (s, 1H), 7.95~7.91 (dd, J₁=6.0 Hz, J₂=9.2 Hz, 1H), 7.80 (s, 1H), 7.32 (t, J=8.8 Hz, 1H), 4.85 (s, 2H), 4.35 (d, J=1.2 Hz, 2H), 4.09 (s, 3H), 3.82 (s, 2H), 2.53~1.96 (m, 14H), 1.28~1.14 (m, 4H).

(DMSO, 400 MHz) δ 8.58 (s, 1H), 7.99~7.95 (dd, J₁=6.0 Hz, J₂=8.8 Hz, 1H), 7.76 (s, 1H), 7.32 (t, J=9.2 Hz, 1H), 4.83 (s, 2H), 4.20 (s, 2H), 4.05 (s, 3H), 3.69 (s, 2H), 2.3 (br, s, 2H), 1.94~1.85 (dd, J₁=14.4 Hz, J₂=24.8 Hz, 4H), 1.06~0.96 (m, 4H).

Example 38: 6-((((1R,4R)-4-(((6-fluoro-3-methoxyquinoxalin-5-yl)methyl)amino) cyclohexyl)amino)methyl)-2H-pyrazino[2,3-b][1,4]oxazin-3(4H)-one

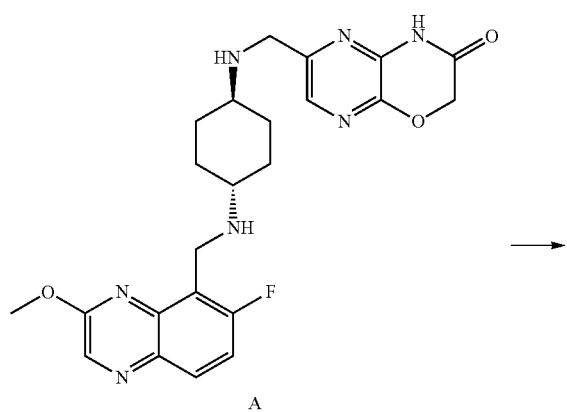

A

120

-continued

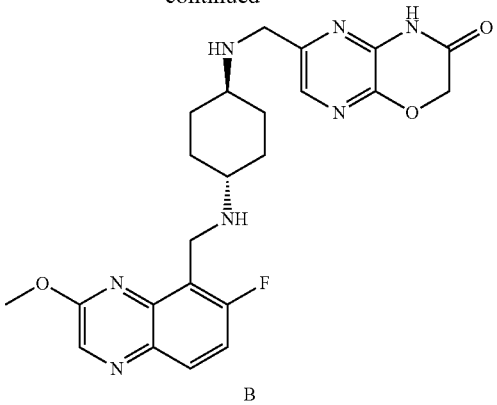

B

Compound A (3.00 g, 6.42 mmol) (99% purity) was purified by a silica gel chromatography column (Dichloromethane:Methanol=50:1~10:1) to yield Compound B (600 mg, 1.28 mmol, 20% yield, 99.5% purity) as a yellow solid.

¹H NMR: (CDCl₃, 400 MHz) δ 8.45 (s, 1H), 7.95~7.91 (dd, J₁=6.0 Hz, J₂=9.2 Hz, 1H), 7.80 (s, 1H), 7.32 (t, J=9.2 Hz, 1H), 4.86 (s, 2H), 4.35 (d, J=1.2 Hz, 2H), 4.10 (s, 3H), 3.83 (s, 2H), 2.51~2.45 (m, 7H), 2.03~1.96 (m, 4H), 1.28~1.14 (m, 4H).

(DMSO, 400 MHz) δ 8.58 (s, 1H), 7.97~7.93 (dd, J₁=6.0 Hz, J₂=8.8 Hz, 1H), 7.75 (s, 1H), 7.51 (t, J=9.6 Hz, 1H), 4.83 (s, 2H), 4.17 (s, 2H), 4.04 (s, 3H), 3.67 (s, 2H), 2.3 (br, s, 2H), 1.94~1.85 (dd, J₁=14.4 Hz, J₂=24.8 Hz, 4H), 1.06~0.96 (m, 4H).

Liposomal Composition Preparation

The compound of formula (V) was loaded into liposomes as set forth below by an active loading method. Lipid solutions were prepared by dissolving lipids (DSPC:Cholesterol:DSPG (55:25:20 molar ratio)) at a total lipid concentration of 120 mg/mL into a heated (65° C.) ethanol:water mixture (80/20 vol/vol). The lipids were hydrated with a 350 mM ammonium sulfate solution also at 65° C. to achieve a lipid concentration of 18 mg/mL. The resulting MLVs were extruded at 65° C. to create LUVs. Extrusion was stopped when LUVs reached a mean particle size of less than 100 nm as measured by dynamic light scattering (Z-average, 90°). The liposomes were ultrafiltered by tangential flow filtration to concentrate the liposomes to 55 mg/mL lipid concentration and then diafiltered to buffer exchange into 150 mM Histidine, pH 7. The compound of formula (V) remote loading was achieved by dissolving this compound in 20 mM sodium acetate pH 3 and incubating with the liposome solution for 1 hour at 50-55° C. The loaded liposome solution was equilibrated to room temperature and then buffer exchanged into 10 mM histidine, 9.2% sucrose pH 6.5 via diafiltration, which removed unencapsulated API. Drug encapsulation efficiency was measured after the liposome fraction was eluted from a size exclusion column. The liposomes were lysed with 5% SDS and 10% ethanol at 50° C. to liberate the compound of formula (V) into solution. Drug content was measured by absorbance at 310 nm against a standard curve.

Biological Activity

Antimicrobial Activity Assay:

Whole-cell antimicrobial activity was determined by broth microdilution using the Clinical and Laboratory Standards Institute (CLSI) recommended procedure, Document M7-A7, "Methods for Dilution Susceptibility Tests for Bacteria that Grow Aerobically" and M11-A8, "Methods for Antimicrobial Susceptibility Testing of Anaerobic Bacteria" The compounds were tested in serial two-fold dilutions ranging from 0.016 to 16 mcg/mL, as well as 0.008 to 32 µg/mL.

Compounds were evaluated against Gram-negative organisms, selected from *Acinetobacter baumannii, Pseudomonas aeruginosa, Klebsiella pneumoniae* and *Escherichia coli*, as well as others.

Compounds were also evaluated against various Gram-positive organisms, various anaerobic organisms, and against various biothreat organisms.

The minimum inhibitory concentration (MIC) was determined as the lowest concentration of compound that inhibited visible growth. A mirror reader was used to assist in determining the MIC endpoint.

Compounds numbered 1-177, as identified above in the present application, were tested in at least one exemplified salt form. Each of compounds 1-177 had an MIC90≤8 µg/ml against at least one of the species listed above.

Tables 1-4 describe results. In all tables, and as each term is mentioned, HCl salt refers to the hydrochloride salt and TFA salt refers to the trifluoroacetate salt. The compound of formulae (V), (VI) and (VII) refers to those compounds set forth hereinabove.

I=*Enterobacter aerogenes*
J=*Klebsiella pneumonia*
K=*stenotrophomonas maltophilla*
L=*citrobacter* spp
M=*Burkholderia cepacia*
N=*Serratia marcescens*
O=*Providencia rettgeri*

TABLE 2

| | Gram Positive MIC90 Data (µg/ml) | | | | | | |
|---|---|---|---|---|---|---|---|
| Compound | A1 | B1 | C1 | D1 | E1 | F1 | G1 |
| Formula (V) free base | ≤0.125 | ≤0.25 | ≤0.25 | | | ≤0.5 | ≤0.5 |
| Formula (V) HCl salt | ≤0.063 | ≤0.125 | ≤0.25 | ≤2 | ≤2 | | |
| Formula (VII) free base | ≤0.125 | ≤0.25 | ≤0.125 | | | ≤0.25 | ≤0.125 |
| Formula (VII) HCl salt | ≤0.125 | ≤0.5 | ≤0.25 | | | ≤0.5 | ≤0.5 |
| Formula (VI) HCl salt | ≤0.125 | ≤0.25 | ≤0.063 | | | | |
| Compound W | ≤0.125 | ≤0.5 | ≤0.125 | | | | |
| Compound Y | ≤0.125 | ≤0.032 | | | | | |
| Compound Z, TFA salt | ≤0.063 | >32 | | | | | |

TABLE 1

| | Gram Negative MIC90 Data | | | | | | | | | | | | | | |
|---|---|---|---|---|---|---|---|---|---|---|---|---|---|---|---|
| Compound | A | B | C | D | E | F | G | H | I | J | K | L | M | N | O |
| Formula (V) free base | ≤0.25 | <0.016 | ≤2 | | ≤2 | ≤2 | | ≤4 | ≤8 | ≤2 | ≤8 | | | | |
| Formula (V) HCl salt | ≤0.063 | | ≤2 | ≤0.25 | | ≤4 | | ≤1 | | | | ≤0.25 | ≤8 | ≤4 | ≤0.5 |
| Formula (VII) free base | ≤1 | <0.016 | ≤2 | ≤0.125 | ≤4 | ≤2 | | ≤1 | ≤4 | ≤4 | ≤2 | | ≤8 | | |
| Formula (VII) HCl salt | ≤1 | <0.016 | ≤2 | ≤0.25 | ≤8 | ≤4 | ≤0.06 | ≤2 | ≤2 | ≤4 | ≤4 | ≤0.5 | ≤16 | ≤2 | ≤1 |
| Formula (VI) HCl salt | ≤0.125 | | ≤16 | ≤0.25 | ≤1 | ≤8 | | ≤1 | ≤4 | ≤4 | ≤4 | | ≤8 | | |
| Compound W | ≤0.25 | | ≤8 | ≤0.125 | ≤2 | 32 | | ≤2 | ≤8 | ≤8 | ≤4 | | ≤16 | | |
| Compound Y | ≤0.032 | | ≤8 | ≤1 | ≤4 | ≤8 | | ≤4 | ≤8 | ≤8 | ≤16 | | | | |
| Compound Z, TFA salt | ≤0.5 | | | | | >32 | | >32 | >32 | | >32 | | | | |

Compound W=6-({[(1S,3R,4S)-4-{[(6-fluoro-3-methoxy-quinoxalin-5-yl)methyl]amino}-3-hydroxycyclohexyl]amino}methyl)-2H,3H,4H-pyrazino[2,3-b][1,4]oxazin-3-one
Compound Y=1-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-7-methoxy-1,2-dihydro-1,8-naphthyridin-2-one
Compound Z=6,8-difluoro-1-methyl-4-oxo-5-(2-((1r,4s)-4-(((3-oxo-3,4-dihydro-2H-pyrazino [2,3-b][1,4]thiazin-6-yl)methyl)amino)cyclohexyl)ethyl)-1,4-dihydroquinoline-3-carboxylic acid
A=*Haemophilus influenza*
B=*Moraxella catarrhalis*
C=*Acinetobacter baumannii*
D=*Escherichia coli*
E=*Pseudomonas aeruginosa*
F=*Proteus mirabilis*
G=*Legionella pneumophila*
H=*Enterobacter cloacae*

Compound W=6-({[(1S,3R,4S)-4-{[(6-fluoro-3-methoxy-quinoxalin-5-yl)methyl]amino}-3-hydroxycyclohexyl]amino}methyl)-2H,3H,4H-pyrazino[2,3-b][1,4]oxazin-3-one
Compound Y=1-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-7-methoxy-1,2-dihydro-1,8-naphthyridin-2-one,
Compound Z=6,8-difluoro-1-methyl-4-oxo-5-(2-((1r,4s)-4-(((3-oxo-3,4-dihydro-2H-pyrazino [2,3-b][1,4]thiazin-6-yl)methyl)amino)cyclohexyl)ethyl)-1,4-dihydroquinoline-3-carboxylic acid
A1=*Staphylococcus aureus*
B1=*Streptococcus pneumonia*
C1=*Streptococcus pyogenes*
D1=*Streptococcus agalactiae*
E1=*viridans* group *Streptococcus*
F1=*Enterococcus faecalis*
G1=*E. faecium*

TABLE 3

| Biothreat MIC90 Data (μg/ml) | | | | | |
|---|---|---|---|---|---|
| Compound | A4 | B4 | C4 | D4 | E4 |
| Formula (V) free base | | | | | |
| Formula (V) HCl salt | ≤0.12 | ≤0.25 | ≤0.5 | ≤4 | ≤4 |
| Formula (VII) free base | | | | | |
| Formula (VII) HCl salt | ≤0.12 | ≤0.12 | ≤0.03 | | |
| Formula (VI) HCl salt | ≤0.125 | ≤0.25 | ≤0.063 | | |
| Compound W | ≤0.125 | ≤0.5 | ≤0.125 | | |
| Compound Y | | | | | |
| Compound Z, TFA salt | | | | | |

A4=*Yersinia pestis*
B4=*Bacillus anthracis*
C4=*Francisella tularensis*
D4=*Burkholderia mallei*
E4=*Burkholderia pseudomallei*
Compound W=6-({[(1S,3R,4S)-4-{[(6-fluoro-3-methoxy-quinoxalin-5-yl)methyl]amino}-3-hydroxycyclohexyl]amino}methyl)-2H,3H,4H-pyrazino[2,3-b][1,4]oxazin-3-one
Compound Y=1-{2-[(3S,4S)-3-hydroxy-4-{[({3-oxo-2H,3H,4H-pyrazino[2,3-b][1,4]thiazin-6-yl}methy)amino]methyl}pyrrolidin-1-yl]ethyl}-7-methoxy-1,2-dihydro-1,8-naphthyridin-2-one
Compound Z=6,8-difluoro-1-methyl-4-oxo-5-(2-((1r,4s)-4-(((3-oxo-3,4-dihydro-2H-pyrazino [2,3-b][1,4]thiazin-6-yl)methyl)amino)cyclohexyl)ethyl)-1,4-dihydroquinoline-3-carboxylic acid

TABLE 4

| Anaerobic MIC Data (μg/ml) | | | | |
|---|---|---|---|---|
| Compound | A111 | B111 | C111 | D111 |
| Formula (V) HCl salt | ≤0.5 | ≤4 | ≤2 | ≤1 |

A111=*Bacteroides fragilis*
B111=*Bacteroides caccae*
C111=*Bacteroides ovatus*
D111=*Bacteroides thetaiotamicron*

*Mycobacterium Tuberculosis* H37Rv Inhibition Assay

The measurement of the minimum inhibitory concentration (MIC) for each tested compound was performed in 96 wells flat-bottom, polystyrene microtiter plates. Ten two-fold drug dilutions in neat DMSO starting at 400 M were performed. Five μl of these drug solutions were added to 95 μl of Middlebrook 7H9 medium. (Lines A-H, rows 1-10 of the plate layout). Isoniazid was used as a positive control, 8 two-fold dilution of Isoniazid starting at 160 μgml$^{-1}$ was prepared and 5 μl of this control curve was added to 95 μl of Middlebrook 7H9 (Difco catalogue Ref. 271310)+ADC medium (Becton Dickinson Catalogue Ref. 211887). (Row 11, lines A-H). Five μl of neat DMSO were added to row 12 (growth and Blank controls).

The inoculum was standardised to approximately $1\times10^7$ cfu/ml and diluted 1 in 100 in Middlebrook 7H9+ADC medium and 0.025% Tween 80 (Sigma P4780), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 hours to determine the MIC value.

Examples were tested in the *Mycobacterium tuberculosis* H37Rv inhibition assay. and showed an MIC value of lower than 2.0 μg/ml. Table 5 describes the results for various compounds.

TABLE 5

| H37Rv MIC Data (μg/ml) | |
|---|---|
| Compound | A11 |
| Formula (V) free base | ≤0.02 |
| Formula (V) HCl salt | ≤0.3 |
| Formula (VII) free base | ≤0.16 |
| Formula (VII) HCl salt | ≤0.3 |
| Formula (VI) HCl salt | ≤0.02 |
| Compound W, HCl salt | ≤0.02 |
| Compound Y, HCl salt | ≤0.02 |
| Compound Z, TFA salt | ≤0.1 |

A11=*Mycobacterium tuberculosis*
Compound W=6-({[(1S,3R,4S)-4-{[(6-fluoro-3-methoxy-quinoxalin-5-yl)methyl]amino}-3-hydroxycyclohexyl]amino}methyl)-2H,3H,4H-pyrazino[2,3-b][1,4]oxazin-3-one
Compound Y=1-{2-[(3S,4S)-3-hydroxy-4-{[({3-oxo-2H,3H,4H-pyrazino[2,3-b][1,4]thiazin-6-yl}methyl)amino]methyl}pyrrolidin-1-yl]ethyl}-7-methoxy-1,2-dihydro-1,8-naphthyridin-2-one
Compound Z=6,8-difluoro-1-methyl-4-oxo-5-(2-((1r,4s)-4-(((3-oxo-3,4-dihydro-2H-pyrazino [2,3-b][1,4]thiazin-6-yl)methyl)amino)cyclohexyl)ethyl)-1,4-dihydroquinoline-3-carboxylic acid
Compound Z=6,8-difluoro-1-methyl-4-oxo-5-(2-((1r,4s)-4-(((3-oxo-3,4-dihydro-2H-pyrazino [2,3-b][1,4]thiazin-6-yl)methyl)amino)cyclohexyl)ethyl)-1,4-dihydroquinoline-3-carboxylic acid As illustrated above, the compound of formula (V) (e.g., the HCl salt) is believed to be particularly useful in treating bacterial infections across a wide range of organisms associated with gram negative, gram positive, anaerobics, biothreat, and tuberculosis, and in a preferred embodiment against *Acinetobacter baumannii, Pseudomonas aeruginosa, Klebsiella pneumoniae* and *Escherichia coli*.

It is to be understood that the invention is not limited to the embodiments illustrated hereinabove and the right is reserved to the illustrated embodiments and all modifications coming within the scope of the following claims.

What is claimed is:
1. A compound, or a pharmaceutically acceptable salt thereof, of formula:

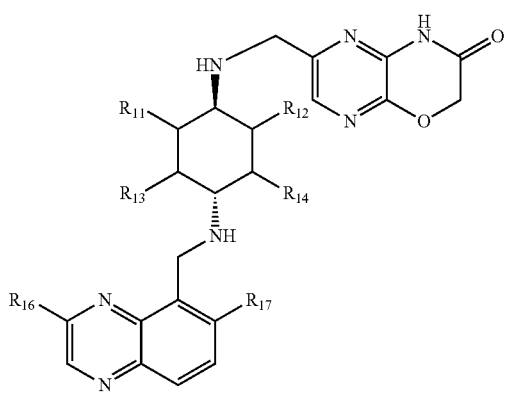

wherein
$R_{11}$, $R_{12}$, $R_{13}$, $R_{14}$, $R_{16}$, and $R_{17}$ are each independently selected from H, ($C_1$-$C_6$) alkyl, OH, ($C_1$-$C_6$) alkoxy, and halogen.

2. The compound or pharmaceutically acceptable salt according to claim 1, wherein $R_{11}$, $R_{12}$, $R_{13}$, $R_{14}$, $R_{16}$, and $R_{17}$ are each independently selected from H, $C_1$alkyl, OH, $C_1$alkoxy, Cl, and F.

3. A compound selected from the group consisting of:
6-((((1R,3S,4R)-4-(((6-fluoro-3-methoxyquinoxalin-5-yl)methyl)amino)-3-hydroxycyclohexyl)amino) methyl)-2H-pyrazino[2,3-b][1,4]oxazin-3(4H)-one;
6-({[(1R,4R)-4-{[(3-methoxyquinoxalin-5-yl)methyl] amino}cyclohexyl]amino}methyl)-2H,3H,4H-pyrazino[2,3-b][1,4]thiazin-3-one;
6-({[(1R,4R)-4-{[(6-fluoro-3-methoxyquinoxalin-5-yl) methyl]amino}cyclohexyl]amino}methyl)-2H,3H,4H-pyrazino[2,3-b][1,4]thiazin-3-one;
6-({[(1R,4R)-4-[({6-fluoro-3-[(1E)-(hydroxyimino) methyl]quinoxalin-5-yl}methyl)amino]cyclohexyl] amino}methyl)-2H,3H,4H-pyrazino[2,3-b][1,4]thiazin-3-one;
6-({[(1R,4R)-4-{[(6-chloro-3-methoxyquinoxalin-5-yl) methyl]amino}cyclohexyl]amino}methyl)-2H,3H,4H-pyrazino[2,3-b][1,4]thiazin-3-one;
6-({[(1R,3S,4R)-4-{[(6-fluoro-3-methoxyquinoxalin-5-yl)methyl]amino}-3-hydroxycyclohexyl] amino}methyl)-2H,3H,4H-pyrazino[2,3-b][1,4]thiazin-3-one;
6-({[(1R,4R)-4-({[3-(2-aminoethoxy)-6-fluoroquinoxalin-5-yl]amino}methyl)cyclohexyl]amino}methyl)-2H,3H,4H-pyrazino[2,3-b][1,4]thiazin-3-one;
6-({[(1R,2S,4R)-4-{[(6-fluoro-3-methoxyquinoxalin-5-yl)methyl]amino}-2-hydroxycyclohexyl] amino}methyl)-2H,3H,4H-pyrazino[2,3-b][1,4]thiazin-3-one;
7-fluoro-8-({[(1S,2R,4S)-2-hydroxy-44({3-oxo-2H,3H,4H-pyrazino[2,3-b][1,4]thiazin-6-yl}methyl)amino] cyclohexyl]amino}methyl)-1-methyl-1,2-dihydroquinoxalin-2-one;
6-({[(1R,4R)-4-{[(6-fluoroquinoxalin-5-yl)methyl] amino}cyclohexyl]amino}methyl)-2H,3H,4H-pyrazino[2,3-b][1,4]thiazin-3-one;
6-({[(1R,4R)-4-[({7-chloro-2-methoxypyrido[2,3-b] pyrazin-8-yl}methyl)amino]cyclohexyl] amino}methyl)-2H,3H,4H-pyrazino[2,3-b][1,4]thiazin-3-one;
6-({[(1R,2S,4R)-4-{[(3-fluoro-6-methoxy-1,5-naphthyridin-4-yl)methyl]amino}-2-hydroxycyclohexyl] amino}methyl)-2H,3H,4H-pyrazino[2,3-b][1,4]thiazin-3-one;
6-({[(1S,3R,4S)-4-{[(6-chloro-3-methoxyquinoxalin-5-yl)methyl]amino}-3-hydroxycyclohexyl] amino}methyl)-2H,3H,4H-pyrazino[2,3-b][1,4]oxazin-3-one;
6-({[(1S,3R,4S)-4-{[(7-chloro-5-fluoro-2-methoxyquinolin-8-yl)methyl]amino}-3-hydroxycyclohexyl] amino}methyl)-2H,3H,4H-pyrazino[2,3-b][1,4]oxazin-3-one;
6-({[(1R,4R)-4-{[(7-fluoro-2-methoxyquinolin-8-yl) methyl]amino}cyclohexyl]amino}methyl)-2H,3H,4H-pyrazino[2,3-b][1,4]oxazin-3-one;
6-({[(1R,4R)-4-{[(6,8-difluoro-3-methoxyquinoxalin-5-yl)methyl]amino}cyclohexyl]amino}methyl)-2H,3H,4H-pyrazino[2,3-b][1,4]oxazin-3-one; and
6-({[(1R,4R)-4-{[(6-chloro-3-methoxyquinoxalin-5-yl) methyl]amino}cyclohexyl]amino}methyl)-2H,3H,4H-pyrazino[2,3-b][1,4]oxazin-3-one;
or a pharmaceutically acceptable salt thereof.

4. A pharmaceutical formulation comprising the compound or pharmaceutically acceptable salt according to claim 1, and a pharmaceutically acceptable carrier.

5. The pharmaceutical formulation according to claim 4, present as a liposomal formulation.

6. A method of treating a bacterial infection comprising administering the compound or pharmaceutically acceptable salt according to claim 1 to a human in need thereof.

7. The method of claim 6, wherein the bacterial infection is caused by one or more organisms selected from the group consisting of *Haemophilus influenza, Moraxella catarrhalis, Acinetobacter baumannii, Escherichia coli, Pseudomonas aeruginosa, Proteus mirabilis, Legionella pneumonia, Stenotrophomonas maltophilla*, the *Citrobacter* genus, *Burkholderia cepacian, Serratia marcescens, Providencia rettgeri, Staphylcoccus aureus, Streptococcus pneumoniae, Streptococcus pyrogenes, Streptococcus agalactiae, Enterococcus faecalis, Enterococcus faecium*, methicillin resistant *Staphylococcus aureus* (MRSA), and anaerobic bacteria of the genus *Bacteroides*.

* * * * *